US010329355B2

(12) United States Patent
June et al.

(10) Patent No.: US 10,329,355 B2
(45) Date of Patent: Jun. 25, 2019

(54) COMPOSITIONS AND METHODS FOR TARGETING STROMAL CELLS FOR THE TREATMENT OF CANCER

(71) Applicants: The Trustees of the University of Pennsylvania, Philadelphia, PA (US); The Wistar Institute of Anatomy and Biology, Philadelphia, PA (US)

(72) Inventors: Carl H. June, Merion Station, PA (US); Ellen Pure, Bryn Mawr, PA (US); Liang-Chuan Wang, Philadelphia, PA (US); Steven Albelda, Philadelphia, PA (US); John Scholler, Penn Valley, PA (US)

(73) Assignees: The Trustees of the University of Pennsylvania, Philadelphia, PA (US); The Wistar Institute of Anatomy and Biology, Philadelphia, PA (US)

( * ) Notice: Subject to any disclaimer, the term of this patent is extended or adjusted under 35 U.S.C. 154(b) by 338 days.

(21) Appl. No.: 15/158,727

(22) Filed: May 19, 2016

(65) Prior Publication Data
US 2016/0326265 A1 Nov. 10, 2016

Related U.S. Application Data

(62) Division of application No. 14/042,306, filed on Sep. 30, 2013, now Pat. No. 9,365,641.

(60) Provisional application No. 61/708,336, filed on Oct. 1, 2012.

(51) Int. Cl.
| C07K 16/28 | (2006.01) |
| C07K 16/40 | (2006.01) |
| C07K 16/18 | (2006.01) |
| A61K 39/00 | (2006.01) |
| A61K 35/17 | (2015.01) |
| C07K 14/725 | (2006.01) |
| C07K 14/705 | (2006.01) |
| C07K 16/30 | (2006.01) |

(52) U.S. Cl.
CPC .............. *C07K 16/40* (2013.01); *A61K 35/17* (2013.01); *A61K 39/0011* (2013.01); *C07K 14/7051* (2013.01); *C07K 14/70517* (2013.01); *C07K 14/70521* (2013.01); *C07K 14/70578* (2013.01); *C07K 16/18* (2013.01); *C07K 16/30* (2013.01); *C07K 2317/24* (2013.01); *C07K 2317/51* (2013.01); *C07K 2317/515* (2013.01); *C07K 2317/622* (2013.01); *C07K 2317/73* (2013.01); *C07K 2319/02* (2013.01); *C07K 2319/03* (2013.01); *C07K 2319/30* (2013.01); *C07K 2319/70* (2013.01); *C12N 2710/10343* (2013.01)

(58) Field of Classification Search
None
See application file for complete search history.

(56) References Cited

U.S. PATENT DOCUMENTS

| 4,444,887 A | 4/1984 | Hoffman |
| 4,716,111 A | 12/1987 | Osband et al. |
| 4,816,567 A | 3/1989 | Cabilly et al. |
| 5,223,409 A | 6/1993 | Ladner et al. |
| 5,225,539 A | 7/1993 | Winter |
| 5,229,275 A | 7/1993 | Goroff |
| 5,350,674 A | 9/1994 | Boenisch et al. |
| 5,403,484 A | 4/1995 | Ladner et al. |
| 5,427,908 A | 6/1995 | Dower et al. |
| 5,516,637 A | 5/1996 | Huang et al. |
| 5,530,101 A | 6/1996 | Queen et al. |
| 5,565,332 A | 10/1996 | Hoogenboom et al. |
| 5,567,610 A | 10/1996 | Borrebaeck et al. |
| 5,571,698 A | 11/1996 | Ladner et al. |
| 5,580,717 A | 12/1996 | Dower |
| 5,585,089 A | 12/1996 | Queen et al. |
| 5,585,362 A | 12/1996 | Wilson et al. |
| 5,658,727 A | 8/1997 | Barbas et al. |
| 5,693,780 A | 12/1997 | Newmann et al. |
| 5,733,743 A | 3/1998 | Johnson et al. |
| 5,750,753 A | 5/1998 | Kimae et al. |
| 5,766,886 A | 6/1998 | Studnicka et al. |
| 5,780,225 A | 7/1998 | Wigler et al. |
| 5,821,047 A | 10/1998 | Garrand et al. |
| 5,858,358 A | 1/1999 | June et al. |
| 5,883,223 A | 3/1999 | Gray |

(Continued)

FOREIGN PATENT DOCUMENTS

| EP | 0239400 | 9/1987 |
| EP | 0519596 | 12/1992 |

(Continued)

OTHER PUBLICATIONS

Ames et al., "Conversion of murine Fabs isolated from a combinatorial phage display library to full length immunoglobulins." J. Immunol. Methods, 184:177-186; (1995) (Abstract).

(Continued)

*Primary Examiner* — Michael D Pak
(74) *Attorney, Agent, or Firm* — Saul Ewing Arnstein & Lehr LLP; Kathryn Doyle

(57) ABSTRACT

The present invention provides compositions and methods for treating cancer in a human. The invention relates to targeting the stromal cell population in a tumor microenvironment. For example, in one embodiment, the invention provides a composition that is targeted to fibroblast activation protein (FAP). The invention includes a chimeric antigen receptor (CAR) which comprises an anti-FAP domain, a transmembrane domain, and a CD3zeta signaling domain.

9 Claims, 43 Drawing Sheets

Specification includes a Sequence Listing.

(56) References Cited

U.S. PATENT DOCUMENTS

| | | | |
|---|---|---|---|
| 5,969,108 | A | 10/1999 | McCafferty et al. |
| 5,993,434 | A | 11/1999 | Dev et al. |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,181,964 | B1 | 1/2001 | Hofmann et al. |
| 6,233,482 | B1 | 5/2001 | Hofmann et al. |
| 6,241,701 | B1 | 6/2001 | Hofmann |
| 6,326,193 | B1 | 12/2001 | Liu et al. |
| 6,331,415 | B1 | 12/2001 | Cabilly et al. |
| 6,352,694 | B1 | 3/2002 | June et al. |
| 6,407,213 | B1 | 6/2002 | Carter et al. |
| 6,516,223 | B2 | 2/2003 | Hofmann |
| 6,534,055 | B1 | 3/2003 | June et al. |
| 6,548,640 | B1 | 4/2003 | Winter |
| 6,567,694 | B2 | 5/2003 | Hayakawa |
| 6,657,103 | B1 | 12/2003 | Kucherlapati et al. |
| 6,678,556 | B1 | 1/2004 | Nolan et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,171,264 | B1 | 1/2007 | Hofmann et al. |
| 7,172,869 | B2 | 2/2007 | June et al. |
| 7,173,116 | B2 | 2/2007 | Fewell et al. |
| 7,175,843 | B2 | 2/2007 | June et al. |
| 7,232,566 | B2 | 6/2007 | June et al. |
| 2004/0014645 | A1 | 1/2004 | Draghia-Akli et al. |
| 2004/0059285 | A1 | 3/2004 | Mathiesen et al. |
| 2004/0092907 | A1 | 5/2004 | Mathiesen et al. |
| 2004/0101519 | A1 | 5/2004 | June et al. |
| 2005/0042664 | A1 | 2/2005 | Wu et al. |
| 2005/0048617 | A1 | 3/2005 | Wu et al. |
| 2005/0052630 | A1 | 3/2005 | Smith et al. |
| 2005/0070841 | A1 | 3/2005 | Mathiesen et al. |
| 2006/0034810 | A1 | 2/2006 | Riley et al. |
| 2006/0121005 | A1 | 6/2006 | Berenson et al. |
| 2007/0128708 | A1 | 6/2007 | Gamelin |
| 2014/0134720 | A1 | 5/2014 | Stauss et al. |
| 2014/0234348 | A1 | 8/2014 | Scholler et al. |

FOREIGN PATENT DOCUMENTS

| | | |
|---|---|---|
| EP | 0592106 | 11/2004 |
| WO | WO 90/002809 | 3/1990 |
| WO | WO 91/09967 | 7/1991 |
| WO | WO 91/10737 | 7/1991 |
| WO | WO 91/10741 | 7/1991 |
| WO | WO92/001047 | 1/1992 |
| WO | WO 92/01047 | 1/1992 |
| WO | WO 92/18619 | 10/1992 |
| WO | WO 92/22324 | 12/1992 |
| WO | WO 93/11236 | 6/1993 |
| WO | WO 93/017105 | 9/1993 |
| WO | WO 95/15982 | 6/1995 |
| WO | WO 95/20401 | 8/1995 |
| WO | WO 96/33735 | 10/1996 |
| WO | WO 96/34096 | 10/1996 |
| WO | WO 98/016654 | 4/1998 |
| WO | WO 98/24893 | 6/1998 |
| WO | WO 98/46645 | 10/1998 |
| WO | WO 98/50433 | 11/1998 |
| WO | WO 01/029058 | 4/2001 |
| WO | WO 01/096584 | 12/2001 |
| WO | WO97/13844 | 2/2007 |
| WO | WO 2012/099973 | 7/2012 |
| WO | WO 2014/039513 | 3/2014 |

OTHER PUBLICATIONS

Baca et al., "Antibody humanization using monovalent phage display." J. Biol. Chem., 272(16):10678-84 (1997).

Batzer et al., "Enhanced evolutionary PCR using oligonucleotides with inosine at the 3'-terminus." Nucleic Acid Res. 19:5081 (1991).

Berg et al. "Selective Expansion of a Peripheral Blood CD81 Memory T Cell Subset Expressing Both Granzyme B and L-Selectin During Primary Viral Infection in Renal Allograft Recipients," Transplant Proc. 30(8):3975-3977, 1998 (2011).

Better et al., "*Escherichia coli* secretion of an active chimeric antibody fragment." Science, 240:1041-1043 (1988) (Abstract).

Bierer et al., "Cyclosporin A and FK506: molecular mechanisms of immunosuppression and probes for transplantation biology." Curr. Opin. Immun. 5:763-773, (1993) (Abstract).

Bird et al., "Single-chain antigen-binding proteins." Science 242:423-426 (1988) (Abstract).

Brennan et al., "Preparation of bispecific antibodies by chemical recombination of monoclonal immunoglobulin G1 fragments." Science, 229:81 (1985) (Abstract).

Brinkman et al., "Phage display of disulfide-stabilized Fv fragments." J. Immunol. Methods, 182:41-50 (1995) (Abstract).

Burton et al., "Human antibodies from combinatorial libraries." Advances in Immunology, 57:191-280 (1994).

Caldas et al., "Design and synthesis of germline-based hemi-humanized single-chain Fv against the CD18 surface antigen." Protein Eng., 13(5):353-60 (2000).

Carter et al., "High level *Escherichia coli* expression and production of a bivalent humanized antibody fragment." Bio/Technology, 10:163-167 (1992) (Abstract).

Clackson et al., Making antibody fragments using phage display libraries. Nature, 352:624-628 (1991) (Abstract).

Cougot, et al., "'Cap-tabolism'" Trends in Biochem. Sci., 29:436-444 (2001) (Abstract).

Couto et al., "Designing human consensus antibodies with minimal positional templates." Cancer Res., 55 (23 Supp):5973s-5977s (1995).

Couto et al., "Anti-BA46 monoclonal antibody Mc3: humanization using a novel positional consensus and in vivo and in vitro characterization." Cancer Res., 55(8):1717-22 (1995).

Elango, et al., "Optimized transfection of mRNA transcribed from a d(A/T)100 tail-containing vector." Biochim. Biophys. Res. Commun., 330:958-966 (2005) (Abstract).

Ertl et al, "Considerations for the clinical application of chimeric antigen receptor T cells: observations from a recombinant DNA Advisory Committee Symposium held Jun. 15, 2010." Cancer Res, 71:3175-81 (2011).

Garland et al., "The use of Teflon cell culture bags to expand functionally active CD8+ cytotoxic T lymphocytes." J. Immunol Meth. 227(1-2):53-63, (1999) (Abstract).

Ghosh et al. (Mumtaz), "Design of liposomes for circumventing the reticuloendothelial cells." Glycobiology 5: 505-10 (1991).

Haanen et al., "Selective expansion of cross-reactive CD8(+) memory T cells by viral variants." J. Exp. Med. 190(9):13191328, (1999).

Henderson et al., "Comparison of the effects of FK-506, cyclosporin A and rapamycin on IL-2 production." Immun. 73:316-321, (1991).

Hoogenboom et al., By-passing immunization. Human antibodies from synthetic repertoires of germline VH gene segments rearrangemed in vitro.: J. Mol. Biol., 227:381 (1991) (Abstract).

Huston et al., "Protein engineering of antibody binding sites: recovery of specific activity in an anti-digoxin single-chain Fv analogue produced in *Escherichia coli*." Proc. Natl. Acad. Sci. USA 85:5879-5883 (1988).

Jackaman et al., "IL-2 intratumoral immunotherapy enhances CD8+ T cells that mediate destruction of tumor cells and tumor-associated vasculature: a novel mechanism for IL-2." J. Immunol. 171:5051-63 (2003).

Jones et al., "Replacing the complementarity-determining regions in a human antibody with those from a mouse." Nature, 321:522-525 (1986) (abstract).

Junghans, "Strategy escalation: an emerging paradigm for safe clinical development of T cell gene therapies." Journal of Translational Medicine, 8:55 (2010).

(56) References Cited

OTHER PUBLICATIONS

Kettleborough et al., "Isolation of tumor cell-specific single-chain Fv from immunized mice using phage-antibody libraries and the re-construction of whole antibodies from these antibody fragments." Eur. J. Immunol., 24:952-958; (1994) (Abstract).
Kohler et al., "Continuous cultures of fused cells secreting antibody of predefined specificity." Nature, 256:495-7 (1975).
Lee et al., "Retroviral transduction of murine primary T lymphocytes." Methods Mol Biol, 506: 83-96; (2009) (Abstract).
Liu et al., "Calcineurin is a common target of cyclophilin-cyclosporin A and FKBP-FK506 complexes." Cell 66:807-815, (1991) (Abstract).
Marks et al., "By-passing immunization. Human antibodies from V-gene libraries displayed on phage." J. Mol. Biol., 222:581-597 (1991) (Abstract).
McCafferty et al., "Phage antibodies: filamentous phage displaying antibody variable domains." Nature, 348:552-554 (1990) (Abstract).
Milone et al., "Chimeric receptors containing CD137 signal transduction domains mediate enhanced survival of T cells and increased antileukemic efficacy in vivo." Mol. Ther. 17(8): 1453-1464 (2009).
Moon et al., "Expression of a Functional CCR2 Receptor Enhances Tumor Localization and Tumor Eradication by Retargeted Human T Cells Expressing a Mesothelin—Specific Chimeric Antibody Receptor." Clin. Cancer Res. 17:4719-30 (2011).
Morea et al., "Antibody modeling: implications for engineering and design." Methods, 20(3):267-79 (2000) (Abstract).
Morgan et al., "Recognition of glioma stem cells by genetically modified T cells targeting EGFRvIII and development of adoptive cell therapy for glioma." Hum Gen Ther 23:1043-53 (2012).
Morimoto et al., "Single-step purification of F(ab')2 fragments of mouse monoclonal antibodies (immunoglobulins G1) by hydrophobic interaction high performance liquid chromatography using TSKgel Phenyl-5PW." Journal of Biochemical and Biophysical Methods, 24:107-117 (1992).
Morrison et al., "Chimeric human antibody molecules: mouse antigen-binding domains with human constant region domains." Proc. Natl. Acad. Sci. USA, 81:6851 (1984).
Mullinax et al., "Expression of a heterodimeric Fab antibody protein in one cloning step." BioTechniques, 12(6):864-869 (1992).
Nacheva and Berzal-Herranz, "Preventing nondesired RNA-primed RNA extension catalyzed by T7 RNA polymerase." Eur. J. Biochem., 270:1485-65 (2003).
Niedermeyer et al., "Targeted disruption of mouse fibroblast activation protein." Mol Cell Biol 2000;20:1089-94 (2000).
Nishikawa, et al. "Nonviral vectors in the new millennium: delivery barriers in gene transfer." Hum Gene Ther., 12(8):861-70 (2001) (Abstract).
Ohtsuka et al., "An alternative approach to deoxyoligonucleotides as hybridization probes by insertion of deoxyinosine at ambiguous codon positions." J. Biol. Chem. 260:2605-2608 (1985).
Padlan, "A possible procedure for reducing the immunogenicity of antibody variable domains while preserving their ligand-binding properties." Molecular Immunology, 28(4/5):489-498 (1991) (Abstract).
Pear et al., "Efficient and rapid induction of a chronic myelogenous leukemia-like myeloproliferative disease in mice receiving P210 bcr/abl-transduced bone marrow." Blood 92(10):3780-92 (1998).
Pedersen et al., "Comparison of surface accessible residues in human and murine immunoglobulin Fv domains. Implication for humanization of murine antibodies." J. Mol. Biol., 235(3):959-73 (1994) (Abstract).
Persic et al., "An integrated vector system for the eukaryotic expression of antibodies or their fragments after selection from phage display libraries." Gene, 187:9-18 (1997) (Abstract).

Riechmann et al., "Reshaping human antibodies for therapy." Nature, 332:323-327 (1988) (Abstract).
Riese et al., "Enhanced effector responses in activated CD8+ T cells deficient in diacylglycerol kinases." Cancer Res 73:3566-77 (2013).
Roder et al., "The EBV-hybridoma tech." Methods Enzymol., 121:140-167 (1986).
Roguska et al., "Humanization of murine monoclonal antibodies through variable domain resurfacing." PNAS, 91:969-973 (1994).
Roguska et al., "A comparison of two murine monoclonal antibodies humanized by CDR-grafting and variable domain resurfacing." Protein Eng., 9(10):895-904 (1996).
Rosenberg et al., "Use of tumor-infiltrating lymphocytes and interleukin-2 in the immunotherapy of patients with metastatic melanoma. A preliminary report." New Engl. J. Med. 319:1676, (1988) (Abstract).
Rossolini et al., "Use of deoxyinosine-containing primers vs degenerate primers for polymerase chain reaction based on ambiguous sequence information." Mol. Cell. Probes 8:91-98 (1994) (Abstract).
Sandhu J S, "A rapid procedure for the humanization of monoclonal antibodies." Gene, 150(2):409-10 (1994) (Abstract).
Sawai et al., "Direct production of the Fab fragment derived from the sperm immobilizing antibody using polymerase chain reaction and cDNA expression vectors." AJRI 34:26-34 (1995) (Abstract).
Schenborn and Mierendorf, "A novel transcription property of SP6 and T7 RNA polymerases: dependence on template structure." Nuc Acids Res., 13:6223-36 (1985).
Stepinski, et al., "Synthesis and properties of mRNAs containing the novel "anti-reverse" cap analogs 7-methyl(39-O-methyl)GpppG and 7-methyl(39-deoxy)GpppG." RNA, 7:1468-95 (2001).
Studnicka et al., "Human-engineered monoclonal antibodies retain full specific binding activity by preserving non-CDR complementarity-modulating residues." Protein Engineering, 7(6):805-814 (1994) (Abstract).
Tan et al., ""Superhumanized" antibodies: reduction of immunogenic potential by complementarity-determining region grafting with human germline sequences: application to an anti-CD28." J. Immunol., 169:1119-25 (2002).
Ui-Tei et al., "Sensitive assay of RNA interference in *Drosophila* and Chinese hamster cultured cells using firefly luciferase gene as target." FEBS Letters 479: 79-82 (2000) (Abstract).
Vaughan et al., "Human antibodies with sub-nanomolar affinities isolated from a large non-immunized phage display library." Nature Biotech., 14:309 (1996) (Abstract).
Verhoeyen et al., "Reshaping human antibodies: grafting an antilysozyme activity." Science, 239:1534-1536 (1988) (Abstract).
Waterhouse et al., "Combinatorial infection and in vivo recombination: a strategy for making large phage antibody repertoires." Nuc. Acids. Res., 21:2265-2266 (1993).
Wooldridge et al., "Immunostimulatory oligodeoxynucleotides containing CpG motifs enhance the efficacy of monoclonal antibody therapy of lymphoma." Blood, 89(8): 2994-2998 (1997).
Wu et al., "Humanization of a murine monoclonal antibody by simultaneous optimization of framework and CDR residues." J. Mol. Biol., 294:151 (1999) (Abstract).
Zhao et al., "Multiple injections of electroporated autologous T cells expressing a chimeric antigen receptor mediate regression of human disseminated tumor." Cancer Res. 70:9053-61 (2010).
Zhong et al., "Retroviral transduction of T-cell receptors in mouse T-cells." J Vis Exp, 44: 2307 (2010).
European Patent Application No. 13843099.6—European Search Report dated Apr. 11, 2016.
Kakarla et al., "Improving T-cell Immunotherapies for Solid Tumors by Targeting the Tumor Stroma." 2011, Biology of Blood and Marrow Transplantation 17(2): S270.
Petrausch et al., "Re-directed T Cells for the treatment of fibroblast activation protein (FAP)—positive malignant pleural mesothelioma." 2012, BMC Cancer 12:615 (7 pages).

Table 1 Depletion of FAP+ cells in flank tumors post FAP-CAR treatment.

|  | AE17.ova | | | TC1 | | | LKR | | |
|---|---|---|---|---|---|---|---|---|---|
|  | Untreated | FAP-CAR | P value | Untreated | FAP-CAR | P value | Untreated | FAP-CAR | P value |
| CD45-CD90+ | 1.86 | 1.15 | 0.001* | 1.72 | 0.60 | 0.04* | 2.68 | 1.84 | 0.009* |
| CD45+ | 0.12 | 0.08 | 0.157 | 0.10 | 0.04 | 0.066 | 0.28 | 0.15 | 0.035* |
| Average tumor volume (mm³) | 627 | 324 | 0.03* | 379 | 140 | 0.002* | 410 | 260 | 0.02* |

The values above indicate the averages of percent FAP+ cells per total tumor population. Tumors were harvest 7-9 days after T cell infusion, and there were 5 mice in each group. Student paired t test was performed to evaluate FAP+ cell depletion, as well as change in tumor volume, after adoptive T cell therapy. * Denotes statistical significance between untreated and FAP-CAR-treated samples, p value < 0.05.

FIGURE 20

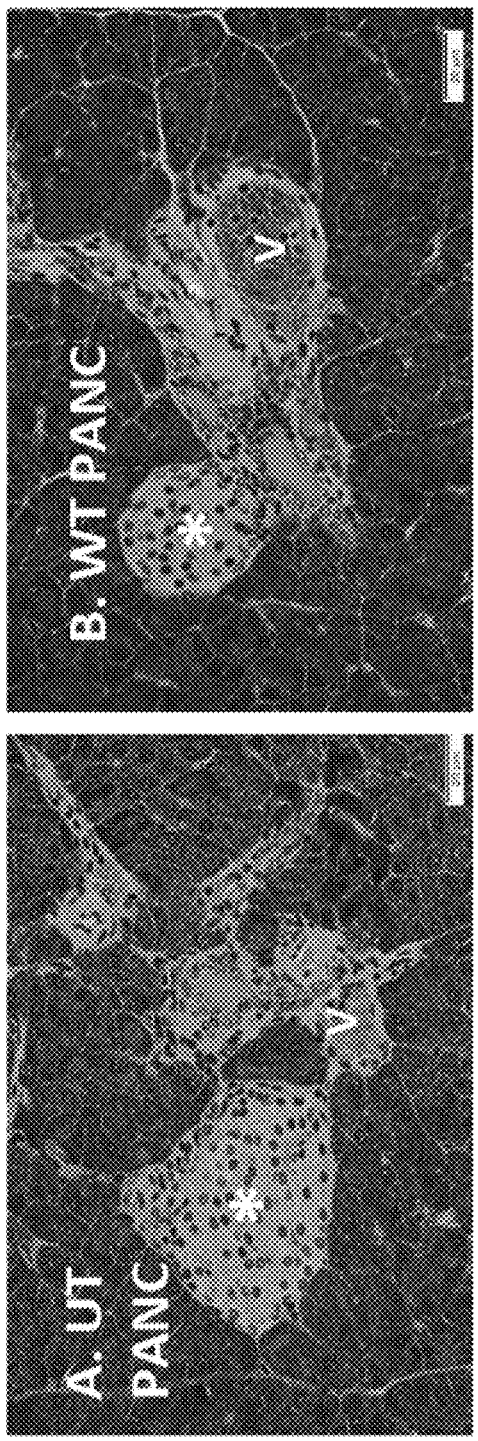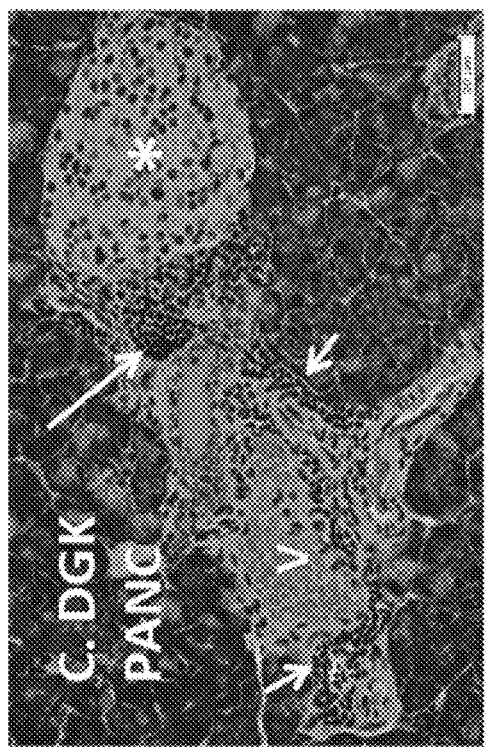
FIGURES 29A-29C

SEQUENCE LISTING

<160> NUMBER OF SEQ ID NOS: 9

<210> SEQ ID NO 1
<211> LENGTH: 1482
<212> TYPE: DNA
<213> ORGANISM: Homo sapiens
<220> FEATURE:
<221> NAME/KEY: misc_feature
<223> OTHER INFORMATION: mFAP-CAR

<400> SEQUENCE: 1

```
atggccctgc ctgtgacagc cctgctgctg cctctggctc tgctgctgca tgccgctaga      60
cctggatccc aggtgcagct gaaagagtcc ggcggaggac tggtgcagcc tggcggatct     120
ctgaagctga gctgtgctgc cagcggcttc accttcagca gctacggcat gagctgggtg     180
cgacagaccg ccgacaagag actggaactg gtggctacca ccaacaacaa cggcggcgtg     240
acctactacc ccgacagcgt gaagggcaga ttcaccatct ccagagacaa cgccaagaac     300
accctgtacc tgcagatgag cagcctgcag agcgaggaca ccgccatgta ctactgcgcc     360
agatacggct actacgccat ggattactgg ggccagggca tcagcgtgac cgtgtctagc     420
ggaggcggcg gatctggcgg agggggatct agtggcggag gctctgacgt gctgatgacc     480
cagacacctc tgagcctgcc agtgtccctg ggcgaccagg ccagcatcag ctgtagaagc     540
agccagagca tcgtgcacag caacggcaac acctacctgg aatggtatct gcagaagccc     600
ggccagagcc ccaagctgct gatctacaag gtgtccaaca gattcagcgg cgtgcccgac     660
agattctccg gcagcggctc tggcaccgac ttcaccgtga agatctccag ggtggaagcc     720
gaggacctgg gcgtgtacta ctgttttcaa ggcagccacg tgcccacac cttcggcgga     780
ggcaccaagc tggaaatcaa ggctagctcc ggaaccacga cgccagcgcc gcgaccacca     840
acaccggcgc ccaccatcgc gtcgcagccc tgtccctgc cccagaggc gtgccggcca     900
gcggcggggg gcgcagtgca cacgaggggg ctggacttcg cctgtgatat ctacatctgg     960
gcgcccttgg ccgggacttg tggggtcctt ctcctgtcac tggttatcac cctttactgc    1020
aaacggggca gaaagaaact cctgtatata ttcaaacaac catttatgag accagtacaa    1080
actactcaag aggaagatgg ctgtagctgc cgatttccag aagaagaaga aggaggatgt    1140
gaactgagag tgaagttcag caggagcgca gacgccccg cgtacaagca gggccagaac    1200
cagctctata acgagctcaa tctaggacga agagaggagt acgatgtttt ggacaagaga    1260
cgtggccggg accctgagat gggggaaag ccgagaagga gaaccctca ggaaggcctg     1320
tacaatgaac tgcagaaaga taagatggcg gaggcctaca gtgagattgg gatgaaaggc    1380
gagcgccgga ggggcaaggg gcacgatggc ctttaccagg gtctcagtac agccaccaag    1440
gacacctacg acgcccttca catgcaggcc ctgccccctc gc                       1482
```

<210> SEQ ID NO 2
<211> LENGTH: 63
<212> TYPE: DNA
<213> ORGANISM: Homo sapiens
<220> FEATURE:
<221> NAME/KEY: misc_feature
<223> OTHER INFORMATION: CD8 leader sequence

<400> SEQUENCE: 2

```
atggccctgc ctgtgacagc cctgctgctg cctctggctc tgctgctgca tgccgctaga      60
``` cct                                                              63

<210> SEQ ID NO 3
<211> LENGTH: 732
<212> TYPE: DNA
<213> ORGANISM: Homo sapiens
<220> FEATURE:
<221> NAME/KEY: misc_feature
<223> OTHER INFORMATION: Anti-mFAP scFv

<400> SEQUENCE: 3
caggtgcagc tgaaagagtc cggcggagga ctggtgcagc ctggcggatc tctgaagctg    60
agctgtgctg ccagcggctt caccttcagc agctacggca tgagctgggt gcgacagacc   120
gccgacaaga gactggaact ggtggctacc accaacaaca cggcggcgt gacctactac    180
cccgacagcg tgaagggcag attcaccatc tccagagaca cgccaagaa caccctgtac    240
ctgcagatga gcagcctgca gagcgaggac accgccatgt actactgcgc cagatacggc   300
tactacgcca tggattactg gggccagggc atcagcgtga ccgtgtctag cggaggcggc   360
ggatctggcg aggggggatc tagtggcgga ggctctgacg tgctgatgac ccagacacct   420
ctgagcctgc cagtgtccct gggcgaccag gccagcatca gctgtagaag cagccagagc   480
atcgtgcaca gcaacggcaa cacctacctg aatggtatc tgcagaagcc cggccagagc   540
cccaagctgc tgatctacaa ggtgtccaac agattcagcg gcgtgcccga cagattctcc   600
ggcagcggct ctggcaccga cttcaccgtg aagatctcca gggtggaagc cgaggacctg   660
ggcgtgtact actgttttca aggcagccac gtgccctaca ccttcggcgg aggcaccaag   720
ctggaaatca ag                                                       732

<210> SEQ ID NO 4
<211> LENGTH: 135
<212> TYPE: DNA
<213> ORGANISM: Homo sapiens
<220> FEATURE:
<221> NAME/KEY: misc_feature
<223> OTHER INFORMATION: CD8a hinge

<400> SEQUENCE: 4
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135

<210> SEQ ID NO 5
<211> LENGTH: 72
<212> TYPE: DNA
<213> ORGANISM: Homo sapiens
<220> FEATURE:
<221> NAME/KEY: misc_feature
<223> OTHER INFORMATION: CD8a transmembrane domain

<400> SEQUENCE: 5
atctacatct gggcgcccct tggccgggact tgtggggtcc ttctcctgtc actggttatc    60
acccttact gc                                                        72

<210> SEQ ID NO 6
<211> LENGTH: 126
<212> TYPE: DNA
<213> ORGANISM: Homo sapiens
<220> FEATURE:
<221> NAME/KEY: misc_feature
<223> OTHER INFORMATION: 4-1BB intracellular domain

<400> SEQUENCE: 6

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 7
<211> LENGTH: 336
<212> TYPE: DNA
<213> ORGANISM: Homo sapiens
<220> FEATURE:
<221> NAME/KEY: misc_feature
<223> OTHER INFORMATION: CD3-zeta signaling domain

<400> SEQUENCE: 7

```
agagtgaagt tcagcaggag cgcagacgcc cccgcgtaca gcagggccga gaaccagctc    60
tataacgagc tcaatctagg acgaagagag gagtacgatg ttttggacaa gagacgtggc   120
cgggaccctg agatggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

<210> SEQ ID NO 8
<211> LENGTH: 116
<212> TYPE: PRT
<213> ORGANISM: Homo sapiens
<220> FEATURE:
<221> NAME/KEY: misc_feature
<223> OTHER INFORMATION: variable domain of IgG heavy chain

<400> SEQUENCE: 8

```
Gln Val Gln Leu Lys Glu Ser Gly Gly Leu Val Gln Pro Gly Gly Ser
1               5                   10                  15

Leu Lys Leu Ser Cys Ala Ala Ser Gly Phe Thr Phe Ser Ser Tyr Gly
            20                  25                  30

Met Ser Trp Val Arg Gln Thr Ala Asp Lys Arg Leu Glu Leu Val Ala
        35                  40                  45

Thr Thr Asn Asn Asn Gly Gly Val Thr Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Gln Ser Glu Asp Thr Ala Met Tyr Tyr Cys Ala
                85                  90                  95

Arg Tyr Gly Tyr Tyr Ala Met Asp Tyr Trp Gly Gln Gly Ile Ser Val
            100                 105                 110

Thr Val Ser Ser
        115
```

<210> SEQ ID NO 9
<211> LENGTH: 112
<212> TYPE: PRT
<213> ORGANISM: Homo sapiens
<220> FEATURE:
<221> NAME/KEY: misc_feature
<223> OTHER INFORMATION: variable domain of IgG light chain

<400> SEQUENCE: 9

```
Asp Val Leu Met Thr Gln Thr Pro Leu Trp Leu Pro Val Ser Leu Gly
```

```
1               5                   10                  15
Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
            35              40              45

Pro Lys Leu Leu Ile Tyr Lys Val Ser Asn Arg Phe Ser Gly Val Pro
    50              55              60

Asp Arg Phe Ser Gly Ser Gly Ser Gly Thr Asp Phe Thr Val Lys Ile
65              70              75              80

Ser Arg Val Glu Ala Glu Asp Leu Gly Val Tyr Tyr Cys Phe Gly Gly
                85              90              95

Ser His Val Pro Tyr Thr Phe Gly Gly Gly Thr Lys Leu Glu Ile Lys
                100             105             110
```

COMPOSITIONS AND METHODS FOR TARGETING STROMAL CELLS FOR THE TREATMENT OF CANCER

CROSS-REFERENCE TO RELATED APPLICATIONS

The present application is a divisional of U.S. patent application Ser. No. 14/042,306, filed Sep. 30, 2013, allowed, which is entitled to priority under 35 U.S.C. § 119(e) to U.S. Provisional Patent Application No. 61/708,336, filed Oct. 1, 2012, which is hereby incorporated by reference in its entirety herein.

STATEMENT REGARDING FEDERALLY SPONSORED RESEARCH OR DEVELOPMENT

This invention was made with government support under CA141144, RO1 CA 172921, and P01 CA66726 awarded by the National Institutes of Health (NIH). The government has certain rights in the invention.

BACKGROUND OF THE INVENTION

Adoptive transfer of T cells directed against antigens expressed by neoplastic cells is an immunotherapeutic approach that has proven effective in some patients. A recent advance in adoptive T cell therapy (ATCT) involves the use of T cells transduced with chimeric antigen receptors (CARs) directed against tumor cell associated antigens.

CARs are typically engineered to contain three regions. The N-terminal extracellular region dictates the antigen specificity of CARs and is encoded by a single chain fragment variable region (scFv) derived from the linked $V_H$ and $V_L$ domains of the antigen binding region of a monoclonal antibody (mAb) specific for the intended targeted antigen. This ligand binding component is followed by a flexible hinge sequence, derived from a CD8α or immunoglobulin sequence and one or more intracellular signaling domains, which may be derived from the cytoplasmic domains of TCR CD3-ε, CD3-γ, or CD3-ζ chains or high-affinity receptor for IgE (FcεRI). The main advantage of CAR technology is that it combines the effector functions of T lymph ocytes with the ability of antibodies to specifically bind antigens with high affinity in a non-MHC restricted fashion. Furthermore, patient-derived blood lymphocytes can be readily expanded and transduced with the desired CAR.

A key need for ATCT is target molecules that will be specific to tumors and effectively reduce tumor size when targeted. While most efforts have focused on targeting tumor antigens, it is evident that other components of the tumor microenvironment, including stromal cells, infiltrating immune cells, vasculature, and extracellular matrix, promote tumor growth and metastasis. These components therefore may represent additional therapeutic targets in order to minimize or eliminate cancerous tumors.

Thus, there is an urgent need in the art for compositions and methods to target stromal cells for the treatment of cancer. The present invention addresses this need.

BRIEF SUMMARY OF THE INVENTION

The invention includes an isolated nucleic acid sequence encoding a chimeric antigen receptor (CAR), wherein the CAR comprises an antigen binding domain, a transmembrane domain, a costimulatory signaling region, and a CD3 zeta signaling domain, wherein the antigen binding domain binds to a stromal cell antigen.

The invention further includes an isolated chimeric antigen receptor (CAR) comprising an antigen binding domain, a transmembrane domain, a costimulatory signaling region, and a CD3 zeta signaling domain, wherein the antigen binding domain binds to a stromal cell antigen.

Also included in the invention is a cell comprising a nucleic acid sequence encoding a chimeric antigen receptor (CAR), the CAR comprising an antigen binding domain, a transmembrane domain, a costimulatory signaling region, and a CD3 zeta signaling domain, wherein the antigen binding domain binds to a stromal cell antigen.

Further included is a vector comprising a nucleic acid sequence encoding a chimeric antigen receptor (CAR), wherein the CAR comprises an antigen binding domain, a transmembrane domain, a costimulatory signaling region, and a CD3 zeta signaling domain, wherein the antigen binding domain binds to a stromal cell antigen.

In these an other embodiments, the antigen binding domain is an antibody or an antigen-binding fragment thereof. In another embodiment, the antigen-binding fragment is a Fab or a scFv. In yet a further embodiment, the stromal cell antigen is expressed on a stromal cell present in a tumor microenvironment. In another embodiment, the tumor is a carcinoma. In an additional embodiment, the stromal cell antigen is fibroblast activation protein (FAP). In yet other embodiments, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof. In another embodiment, the nucleic acid sequence comprises SEQ ID NO: 1 in and yet another embodiment, the CAR is encoded by a nucleic acid sequence comprising SEQ ID NO: 1.

The invention also includes a method for stimulating a T cell-mediated immune response to a stromal cell population in a mammal. The method comprises administering to a mammal an effective amount of a cell genetically modified to express a CAR, wherein the CAR comprises an antigen binding domain, a transmembrane domain, a costimulatory signaling region, and a CD3 zeta signaling domain, and wherein the antigen binding domain is selected to specifically recognize the stromal cell population.

In these and other embodiments, the antigen binding domain is an antibody or an antigen-binding fragment thereof. In another embodiment, the antigen-binding fragment is a Fab or a scFv. In yet a further embodiment, the stromal cell antigen is expressed on a stromal cell present in a tumor microenvironment. In another embodiment, the tumor is a carcinoma. In an additional embodiment, the stromal cell antigen is fibroblast activation protein (FAP). In yet other embodiments, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof. In another embodiment, the nucleic acid sequence comprises SEQ ID NO: 1 in and yet another embodiment, the CAR is encoded by a nucleic acid sequence comprising SEQ ID NO: 1.

The invention also includes a composition comprising an anti-FAP binding domain. In one embodiment, the composition is an antibody, or fragment thereof. In another embodiment, the composition is encoded by a nucleic acid sequence comprising SEQ ID NO: 3.

The invention further includes a composition comprising a cell comprising a nucleic acid sequence encoding a chimeric antigen receptor (CAR), the CAR comprising an antigen binding domain, a transmembrane domain, a costimulatory signaling region, and a CD3 zeta signaling domain, wherein the antigen binding domain binds to a stromal cell antigen, in combination with an antitumor vaccine.

The invention additionally includes a method of treating cancer in a mammal comprising administering to the mammal a cell comprising a nucleic acid sequence encoding a chimeric antigen receptor (CAR), the CAR comprising an antigen binding domain, a transmembrane domain, a costimulatory signaling region, and a CD3 zeta signaling domain, wherein the antigen binding domain binds to a stromal cell antigen, and an antitumor vaccine.

One embodiment, the cell and the antitumor vaccine are co-administered to the mammal. In another embodiment, the cell and the antitumor vaccine are administered to the mammal separately.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 20 is a Table (Table 1) depicting depletion of FAP+ cells in flank tumors post FAP-CAR treatment.

FIG. 21C shows FAP-CAR T cells enhance efficacy of cancer vaccine. TC1 tumor cells were inoculated into the right flanks of C57BL/6 mice. When tumors reached 200 mm, one dose of Ad.E7 (10$^9$ pfu) was given to the mice contralaterally to their flank tumors (black arrow). FAP-CAR T cells (10 million cells) were given 4 days later (gray arrow). Tumor measurements were then followed. The values are expressed as the mean±SEM (n=5). * Denotes significant difference between untreated and the combo groups (p<0.05).

FIG. 29A depicts pancreas histology. Representative H&E sections of the pancreas are shown from control untreated tumor-bearing mice.

FIG. 29B shows representative H&E sections of the pancreas from tumor-bearing mice treated with wild-type FAP-CAR T cells. No changes were seen in the organs treated with WT FAP-CAR T cells.

FIG. 29C shows representative H&E sections of the pancreas from tumor-bearing mice treated with DGK knockout FAP-CAR T cells. Organs were harvested one week after T cell infusion. Pancreatic Islets of Langerhans are marked by an asterisk. Blood vessels are labeled with a "V". In mice treated with DGK knockout FAPCAR T cells, however, focal areas of lymphocytes were noted in a peri-islet (white arrows) and peri-vascular (white arrowheads) location.

DETAILED DESCRIPTION

Figure 1:
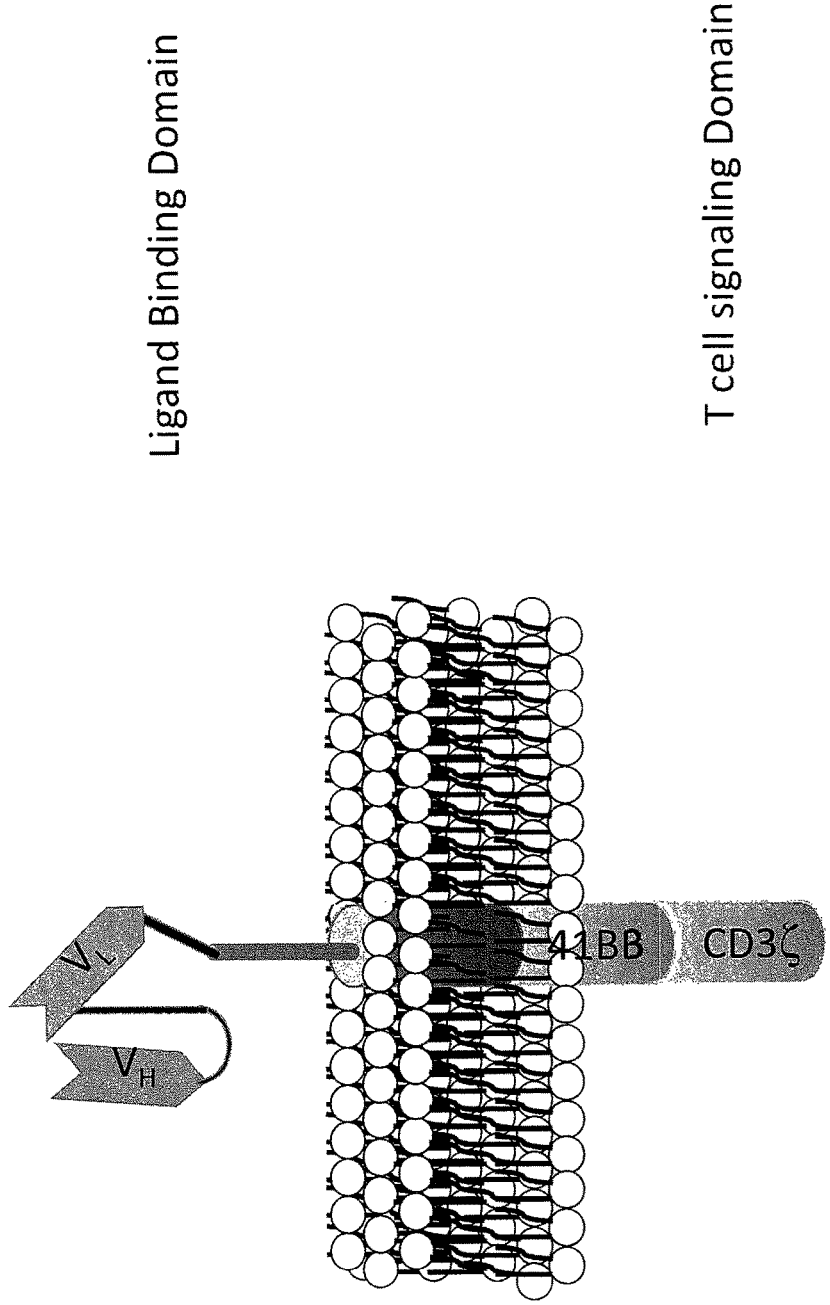
FIG. 1 depicts a schematic of an exemplary CAR.

The invention relates to compositions and methods for targeting stromal cells in the treatment of cancer. Immunotherapy for cancer, whether adoptive T cell therapy, antibody- or vaccine-based, has to date been focused primarily on targeting antigens expressed by the neoplastic cells. It is now evident that other components including stromal cells, infiltrating inflammatory/immune cells, vasculature and extracellular matrix that comprise the tumor microenvironment, are also required for or promote tumor growth and metastasis and therefore present additional therapeutic targets.

In one embodiment, the present invention comprises compositions that target fibroblast activation protein (FAP). FAP is a cell surface protease that is expressed on the vast majority of stromal cells in virtually all human carcinomas. In one embodiment, the present invention provides an antibody that specifically binds to FAP. In one embodiment, the present invention provides compositions comprising an anti-FAP antibody, or an FAP binding fragment thereof. Non-limiting Examples of compositions targeting FAP encompassed by the present invention include antibodies, immunoconjugates, antibody conjugates, vaccines, and chimeric antigen receptors (CARs) that target FAP.

The present invention has certain advantages over prior art cancer treatments in that antibody conjugates can have limited tumor penetration and often induce an immune response in the host, and vaccination may lead to long lasting endogenous immunity to FAP. The present compositions, i.e., using an anti-FAP CAR T cell is designed to circumvent these limitations.

In one embodiment, the present invention comprises a method to treat cancer comprising administering to a subject a composition targeting a stromal cell in a tumor microenvironment. In one embodiment, the composition comprises an anti-FAP antibody, or a FAP binding fragment thereof. In one embodiment, administration of the composition reduces and/or eliminates the stromal cell population. In one embodiment, administration of the composition reduces and/or eliminates the cancer.

In one embodiment, the present invention provides a CAR comprising an anti-FAP antibody, or an FAP binding fragment thereof. CARs are molecules that combine antibody-based specificity for a desired antigen with a T cell receptor-activating intracellular domain to generate a chimeric protein that exhibits a specific anti-antigen cellular immune activity. In some embodiments, a CAR targeting FAP is preferred. A CAR targeting FAP is referred to herein as an FAP-CAR.

The present invention provides for the incorporation of an anti-FAP binding domain into a CAR in order to treat and eliminate tumors. As discussed elsewhere herein, FAP-CAR displays specificity in recognizing FAP expressing cells. Further, T cells transduced with FAP-CAR are able to reduce tumor size.

The present invention provides for the targeting of stromal cells in the treatment of cancer, whether or not the stromal cells themselves are cancer cells. A potential limitation of CARs targeted to tumor cells is that antigen expression on tumors is heterogeneous and subject to antigen loss. Therefore, in some embodiments, the present invention is directed towards the targeting of the more genetically stable stromal cells and thereby avoids the problems associated with targeting tumor antigens directly. In some embodiments, the more genetically stable stromal cells are not a cancer cell.

The present invention relates generally to the use of T cells genetically modified to stably express a desired CAR. T cells expressing a CAR are referred to herein as CAR T cells or CAR modified T cells. Preferably, the cell can be genetically modified to stably express an antibody binding domain (e.g., anti-FAP) on its surface, conferring novel antigen specificity that is MHC independent. In some instances, the T cell is genetically modified to stably express a CAR that combines an antigen recognition domain of a specific antibody with an intracellular domain of the CD3-zeta chain or FcγRI protein into a single chimeric protein.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In some embodiments, the extracellular domain also comprises a hinge domain.

With respect to the cytoplasmic domain, the CAR of the invention can be designed to comprise a signaling domain of a costimulatory molecule. For example, the CAR of the invention can be designed to comprise the CD28 and/or 4-1BB signaling domain by itself or be combined with any other desired cytoplasmic domain(s) useful in the context of the CAR of the invention. In one embodiment, the cytoplasmic domain of the CAR can be designed to further comprise the signaling domain of CD3-zeta. For example, the cytoplasmic domain of the CAR can include, but is not limited to, CD3-zeta, 4-1BB and CD28 signaling modules, and combinations thereof (FIG. 1). Accordingly, the invention provides CAR T cells and methods of their use for adoptive therapy.

In one embodiment, the CAR T cells of the invention can be generated by introducing a lentiviral vector comprising the desired CAR, for example a CAR comprising anti-FAP, a transmembrane domain, and CD3zeta signaling domains, into the cells. In one embodiment, the CAR T cells of the invention are able to replicate in vivo resulting in long-term persistence that can lead to sustained tumor control.

In another embodiment, the CAR T cells of the invention can be generated by transfecting an RNA encoding the desired CAR, for example a CAR comprising anti-FAP, a transmembrane domain, and CD3-zeta signaling domains, into the cells. In one embodiment, the CAR is transiently expressed in the genetically modified CAR T cells.

In one embodiment the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

In one embodiment, the invention relates to genetically modified T cells expressing a CAR for the treatment of a patient with cancer. The present invention is based upon the finding that the inclusion of the anti-FAP antigen binding domain in a CAR allows specific recognition of FAP expressing cells and tumor reduction.

In yet another embodiment, the invention relates generally to the treatment of a patient at risk of developing cancer. The invention also includes treating a malignancy or an autoimmune disease in which chemotherapy and/or immunotherapy in a patient results in significant immunosuppression in the patient, thereby increasing the risk of the patient of developing cancer.

The invention includes using T cells expressing an FAP-CAR, including the CD3-zeta intracellular domain (also referred to as FAP-CAR T cells). In one embodiment, the FAP-CAR T cells of the invention can undergo robust in vivo T cell expansion and can establish FAP-specific memory cells that persist at high levels for an extended amount of time in blood and bone marrow. In some instances, the FAP-CAR T cells of the invention infused into a patient can eliminate tumor cells in vivo in patients with cancer. The invention includes any anti-FAP binding domain fused with one or more intracellular domains selected from the group of a CD137 (4-1BB) signaling domain, a CD28 signaling domain, a CD3zeta signal domain, and any combination thereof.

Definitions

Unless defined otherwise, all technical and scientific terms used herein have the same meaning as commonly understood by one of ordinary skill in the art to which the invention pertains.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or in some instances ±10%, or in some instances ±5%, in some instances ±1%, and in some instances ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, the term "Chimeric Antigen Receptor" or alternatively a "CAR" refers to a recombinant polypeptide construct comprising at least an extracellular antigen binding domain, a transmembrane domain and a cytoplasmic signaling domain comprising a functional signaling domain derived from a stimulatory molecule as defined below. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from 4 1BB (i.e., CD137) and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the scFv domain during cellular processing and localization of the CAR to the cellular membrane.

As used herein, a "signaling domain" is the functional portion of a protein which acts by transmitting information within the cell to regulate cellular activity via defined signaling pathways by generating second messengers or functioning as effectors by responding to such messengers.

As used herein, "a stromal cell antigen" refers to an antigen expressed on or by a stromal cell.

As used herein, 'FAP" refers to fibroblast activation protein. The term should be construed to include not only fibroblast activation protein, but variants, homologs, fragments and portions thereof to the extent that such variants, homologs, fragments and portions thereof retain the activity of FAP as disclosed herein.

The term "antibody," as used herein, refers to an immunoglobulin molecule which specifically binds with an antigen. Antibodies can be polyconal or monoclonal, multiple or single chain, or intact immunoglobulins, and may be derived from natural sources or from recombinant sources. Antibodies such as IgG are typically tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR composition of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

An "antibody heavy chain," as used herein, refers to the larger of the two types of polypeptide chains present in antibody molecules in their naturally occurring conformations, and which normally determines the class to which the antibody belongs An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "recombinant antibody" as used herein, is meant an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" as used herein is defined as a molecule that can provoke an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or can be macromolecules besides a polypeptide. Such a biological sample can include, but is not limited to a tissue sample, a tumor sample, a cell or fluid with other biological components.

The term "anti-tumor effect" as used herein, refers to a biological effect which can be manifested by various means, including but not limited to, a decrease in tumor volume, a decrease in the number of tumor cells, a decrease in the number of metastases, an increase in life expectancy, a decrease in tumor cell proliferation, a decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to whom it is later to be re-introduced into the individual.

"Allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, the term "conservative sequence modifications" is intended to refer to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody or antibody fragment of the invention can be replaced with other amino acid residues from the same side chain family and the altered antibody or antibody fragment can be tested for the ability to bind CD19 using the functional assays described herein.

By the term "stimulation," used in the context of CART, is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," used in the context of CART, means a molecule expressed by a T cell that provide the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MEW molecule loaded with peptide, and which leads to mediation of a T cell response, including, but not limited to, proliferation, activation, differentiation, and the like. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, CD278 (also known as "ICOS") and CD66d. In a specific CAR of the invention, the cytoplasmic signaling molecule in any one or more CARS of the invention, including CARs comprises a cytoplasmic signaling sequence derived from CD3-zeta. In a specific CAR of the invention, the cytoplasmic signaling sequence derived from CD3-zeta is the sequence provided as SEQ ID NO:7 or the equivalent residues from a non-human species, e.g., mouse, rodent, monkey, ape and the like.

An "antigen presenting cell," as used herein, means an immune system cell such as an accessory cell (e.g., a B-cell, a dendritic cell, and the like) that displays foreign antigens complexed with major histocompatibility complexes (MHC's) on their surfaces. T-cells may recognize these complexes using their T-cell receptors (TCRs). APCs process antigens and present them to T-cells.

As used herein "zeta" or alternatively "zeta chain", "CD3-zeta" or "TCR-zeta" is defined as the protein provided as GenBan accno. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank accno. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO7.

A "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MEW class I molecule, BTLA and a Toll ligand receptor, as well as OX40, CD27, CD28, CDS, ICAM-1, LFA-1 (CD11a/CD18) and 4-1BB (CD137).

As used herein "4-1BB" is defined as member of the TNFR superfamily with an amino acid sequence provided as GenBank accno. AAA62478.2, or the equivalent residues from a non-human species, e.g., mouse, rodent, monkey, ape and the like; and a "4-1BB costimulatory domain" are defined amino acid residues 214-255 of GenBank accno. AAA62478.2, or the equivalent residues from a non-human species, e.g., mouse, rodent, monkey, ape and the like. In one aspect, the "4-1BB costimulatory domain" is the sequence provided as SEQ ID NO:6 or the equivalent residues from a non-human species, e.g., mouse, rodent, monkey, ape and the like.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

A "transfer vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, polylysine compounds, liposomes, and the like. Examples of viral transfer vectors include, but are not limited to, adenoviral vectors, adeno-associated virus vectors, retroviral vectors, lentiviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

A "lentiviral vector" is a vector derived from at least a portion of a lentivirus genome, including especially a self-inactivating lentiviral vector as provided in Milone et al., Mol. Ther. 17(8): 1453-1464 (2009). Other Examples or lentivirus vectors that may be used in the clinic as an alternative to the pELPS vector, include but not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994))

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" antigen or "overexpression" of the antigen is intended to indicate an abnormal level of expression of the antigen in a cell from a disease area like a solid tumor within a specific tissue or organ of the patient relative to the level of expression in a normal cell from that tissue or organ. Patients having solid tumors or a hematological malignancy characterized by overexpression of the antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody or antibody fragment which recognizes and binds with a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating cancer. The cancer may be a hematological malignancy, a solid tumor, a primary or a metastasizing tumor.

In one embodiment, the invention provides a composition targeting the stromal cell population in a tumor microenvironment. The advantages of targeting stromal cells are: i) that compared to neoplastic cells, the rate of mutation in stromal cells is dramatically lower and therefore stromal cells are less prone to developing resistance to therapy; ii) the tumor promoting effects of stromal cells are common to multiple tumor types and therefore the same stromal cell targeted therapies can be indicated in multiple tumor types; iii) combining therapies directed against neoplastic cells with therapies directed against stromal cells can have synergistic tumoricidal activity; iv) pro-tumorigenic changes in stromal cells occur and in at least some cases are required to establish the so-called pre-metastatic niche. Therefore, in various embodiments, targeting stromal cells markedly reduces the development of distal metastases which are the cause of the vast majority of cancer-related deaths. The effective targeting of stromal cells requires a stromal cell specific antigen. The stromal cell antigen to target using a targeted therapy should be one expressed on the cell surface of a majority of stromal cells in desmoplastic tumors in which stromal cells support tumor initiation, progression and metastasis.

In one embodiment, the present invention provides a composition comprising a FAP binding domain. In one embodiment, the composition comprises an anti-FAP antibody, or a FAP binding fragment thereof. Non-limiting examples of compositions which comprise a FAP binding domain include an antibody, an immunoconjugate, an antibody conjugate, and a chimeric antigen receptor (CAR). The present invention is partly based on the generation of an anti-FAP antibody.

In one embodiment, the invention provides a cell (e.g., T cell) engineered to express a CAR comprising an FAP binding domain, wherein the CAR T cell exhibits an antitumor property. The CAR of the invention can be engineered to comprise an extracellular domain having an FAP binding domain fused to an intracellular signaling domain of the T cell antigen receptor complex zeta chain (e.g., CD3-zeta). The CAR of the invention when expressed in a T cell is able to redirect antigen recognition based on the FAP antigen binding specificity.

The present invention provides targeting to stromal cells, rather than tumor cells directly, as it was seen that stromal cells existing in the tumor microenvironment have tumorigenic activity. For example, stromal cells in tumor microenvironments promote tumor growth and metastasis. Therefore, targeting of FAP expressing stromal cells affects a tumor cell so that the tumor cell fails to grow, is prompted to die, or otherwise is affected so that the tumor burden in a patient is diminished or eliminated. The FAP binding domain is preferably fused with an intracellular domain from one or more of a costimulatory molecule and a zeta chain. Preferably, the antigen binding domain is fused with one or more intracellular domains selected from the group of a CD137 (4-1BB) signaling domain, a CD28 signaling domain, a CD3zeta signal domain, and any combination thereof.

In some embodiments, the present invention is directed to a retroviral or lentiviral vector encoding a CAR that is stably integrated into a T cell and stably expressed therein. In other embodiments, the present invention is directed to an RNA encoding CAR that is transfected into a T cell and transiently expressed therein. Transient, non-integrating expression of CAR in a cell mitigates concerns associated with permanent and integrated expression of CAR in a cell.

Anti-FAP Antibodies

The present invention provides an anti-FAP antibody and compositions comprising an anti-FAP antibody, or fragment thereof. The compositions of the invention are used to target FAP-expressing stromal cells present in the tumor microenvironment, in the treatment of cancer.

Polyclonal antibodies are preferably raised in animals by multiple subcutaneous (s.c.) or intraperitoneal (i.p.) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobertzoyl sulfosuccinimide ester (conjugation through cysteine residues), N-hydroxysuccinimide (through lysine residues), glutaraldehyde, succunic anhydride, $SOCl_2$.

Monoclonal anti-FAP antibodies of the invention can be generated using a wide variety of techniques known in the art including the use of hybridoma, recombinant, and phage display technologies, or a combination thereof. Antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the FAP antigen. For example, the monoclonal antibodies to be used in accordance with the present invention may be made by the hybridoma method first described by Kohler et al., Nature, 256:495 (1975), which can be used to generate murine antibodies (or antibodies derived from other nonhuman mammals, e.g., rat, goat, sheep, cows, camels, etc.), or human antibodies derived from transgenic animals (see, U.S. Pat. Nos. 6,075,181, 6,114,598, 6,150,584 and 6,657,103). Alternatively, the monoclonal antibodies can be made by recombinant DNA methods (see, e.g., U.S. Pat. No. 4,816,567) and include chimeric and humanized antibodies. The "monoclonal antibodies" may also be isolated from phage antibody libraries using the techniques described in Clackson et al., Nature, 352:624-628 (1991) and Marks et al., J. Mol. Biol., 222:581-597 (1991), for example.

An engineered anti-FAP antibody can be produced by any means known in the art, including, but not limited to those techniques described herein and improvements to those techniques. Large-scale high-yield production typically involves culturing a host cell that produces the engineered anti-FAP antibody and recovering the anti-FAP antibody from the host cell culture.

Monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in Monoclonal Antibodies and T-Cell Hybridomas, 563-681 (Elsevier, N.Y., 1981) (said references incorporated by reference in their entireties). For example, in the hybridoma method, a mouse or other appropriate host animal, such as a hamster or macaque monkey, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RFMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the anti-FAP antibodies of the invention is readily isolated and sequenced using conventional procedures (e.g., by using oligonucleotide probes that are capable of binding specifically to genes encoding the heavy and light chains of the anti-FAP antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of anti-FAP antibodies in the recombinant host cells.

In phage display methods, functional antibody domains are displayed on the surface of phage particles which carry the polynucleotide sequences encoding them. In particular, DNA sequences encoding $V_H$ and $V_L$ domains are amplified from animal cDNA libraries (e.g., human or murine cDNA libraries of affected tissues). The DNA encoding the $V_H$ and $V_L$ domains are recombined together with an scFv linker by PCR and cloned into a phagemid vector. The vector is electroporated in E. coli and the E. coli is infected with helper phage. Phage used in these methods are typically filamentous phage including fd and M13 and the $V_H$ and $V_L$ domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods, 182:41-50; Ames et al., 1995, J. Immunol. Methods, 184:177-186; Kettleborough et al., 1994, Eur. J. Immunol., 24:952-958; Persic et al., 1997, Gene, 187:9-18; Burton et al., 1994, Advances in Immunology, 57:191-280; International Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT Publication No. WO 92/22324; Mullinax et al., 1992, BioTechniques, 12(6):864-869; Sawai et al., 1995, AJRI 34:26-34; and Better et al., 1988, Science, 240:1041-1043 (said references incorporated by reference in their entireties).

In a further embodiment, antibodies may be isolated from antibody phage libraries generated using the techniques described in McCafferty et al., Nature, 348:552-554 (1990). Clackson et al., Nature, 352:624-628 (1991). Marks et al., J. Mol. Biol., 222:581-597 (1991) describe the isolation of murine and human antibodies, respectively, using phage libraries. Chain shuffling can be used in the production of high affinity (nM range) human antibodies (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of anti-FAP antibodies.

To generate whole antibodies, PCR primers including $V_H$ or $V_L$ nucleotide sequences, a restriction site, and a flanking sequence to protect the restriction site can be used to amplify the $V_H$ or $V_L$ sequences in scFv clones.

Utilizing cloning techniques known to those of skill in the art, the PCR amplified $V_H$ domains can be cloned into vectors expressing a $V_H$ constant region, e.g., the human gamma 4 constant region, and the PCR amplified $V_L$ domains can be cloned into vectors expressing a $V_1$ constant region, e.g., human kappa or lamba constant regions. Preferably, the vectors for expressing the $V_H$ or $V_L$ domains comprise an EF-1α promoter, a secretion signal, a cloning site for the variable domain, constant domains, and a selection marker such as neomycin. The $V_H$ and $V_L$ domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also may be modified, for example, by substituting the coding sequence for human heavy- and light-chain constant domains in place of the homologous murine sequences (U.S. Pat. No. 4,816,567; Morrison et al., Proc. Natl. Acad. Sci. USA, 81:6851 (1984)), or by covalently joining to the immunoglobulin coding sequence all or part of the coding sequence for a non-immunoglobulin polypeptide.

The anti-FAP antibodies described herein specifically include chimeric antibodies (immunoglobulins) in which a portion of the heavy and/or light chain is identical with or homologous to corresponding sequences in antibodies derived from a particular species or belonging to a particular antibody class or subclass, while another portion of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences (U.S. Pat. No. 5,693,780).

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., published U.S. patent application US2005/0042664, published U.S. patent application US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized anti-FAP antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting, (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of anti-FAP antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety. Anti-FAP antibodies can be humanized with retention of high affinity for FAP and other favorable biological properties. A "humanized" antibody retains a similar antigenic specificity as the original antibody, i.e., in the present invention, the ability to bind human FAP antigen. However, using certain methods of humanization, the affinity and/or specificity of binding of the antibody for human FAP antigen may be increased using methods of "directed evolution", as described by Wu et al., J. Mol. Biol., 294:151 (1999), the contents of which are incorporated herein by reference herein in their entirety.

For in vivo use of antibodies in humans, it may be preferable to use human antibodies. Completely human antibodies are particularly desirable for therapeutic treatment of human subjects. Human antibodies can be made by a variety of methods known in the art including phage display methods described above using antibody libraries derived from human immunoglobulin sequences, including improvements to these techniques. See also U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human anti-FAP antibodies can also be produced using transgenic mice which are incapable of expressing functional endogenous immunoglobulins, but which can express human immunoglobulin genes. Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. Human antibodies may also be generated by in vitro activated B cells (see, U.S. Pat. Nos. 5,567,610 and 5,229,275, each of which is incorporated herein by reference in its entirety). Human antibodies may also be generated by in vitro using hybridoma techniques such as, but not limited to, that described by Roder et al. (Methods Enzymol., 121:140-167 (1986)).

"Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

Traditionally, these fragments were derived via proteolytic digestion of intact antibodies (see, e.g., Morimoto et al., Journal of Biochemical and Biophysical Methods, 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology, 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See, for example, WO 93/16185. In certain embodiments, the antibody is not a Fab fragment.

Therapeutic Anti-FAP Compositions

The anti-FAP antibody used in the compositions and methods of the invention is preferably an antibody that mediates the specific elimination of FAP expressing cells. The antibody may be a polyclonal antibody, monoclonal antibody, synthetic antibody, humanized antibody, human antibody, or fragments thereof.

The anti-FAP antibodies used in the compositions and methods of the invention can be naked antibodies, immunoconjugates, chimeric antigen receptors, or fusion proteins. Preferably the anti-FAP antibodies described above for use in the compositions and methods of the invention are able to reduce or deplete stromal cells in a human treated therewith. Such depletion may be achieved via various mechanisms such as antibody-dependent cell-mediated cytotoxicity (ADCC) and/or complement dependent cytotoxicity (CDC). By "depletion" of stromal cells it is meant a reduction in stromal cells in particular tissue(s) by at least about 25%, 40%, 50%, 65%, 75%, 80%, 85%, 90%, 95% or more. In particular embodiments, virtually all detectable stromal cells are depleted from the particular tissue(s).

Covalent modifications of the anti-FAP antibody of the invention are included within the scope of this invention. They may be made by chemical synthesis or by enzymatic or chemical cleavage of the antibody, if applicable. Other types of covalent modifications of the anti-FAP antibody are introduced into the molecule by reacting targeted amino acid residues of the antibody with an organic derivatizing agent that is capable of reacting with selected side chains or the N- or C-terminal residues.

An anti-FAP antibody composition may be formulated with a pharmaceutically-acceptable carrier. The term "pharmaceutically acceptable" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, boric, formic, malonic, succinic, and the like. Also, pharmaceutically-acceptable salts can be prepared as alkaline metal or alkaline earth salts, such as sodium, potassium or calcium salts. The term "carrier" denotes an organic or inorganic ingredient, natural or synthetic, with which the active ingredient is combined to facilitate the application. The components of the pharmaceutical compositions also are capable of being co-mingled with the antibodies of the present invention, and with each other, in a manner such that there is no interaction which would substantially impair the desired pharmaceutical efficacy.

The anti-FAP antibody compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The formulations to be used for in vivo administration are typically sterile. This is readily accomplished by filtration through sterile filtration membranes.

Administration of the compositions of the invention to a human patient can be by any route, including but not limited to intravenous, intradermal, transdermal, subcutaneous, intramuscular, inhalation (e.g., via an aerosol), buccal (e.g., sub-lingual), topical (i.e., both skin and mucosal surfaces, including airway surfaces), intrathecal, intraarticular, intrapleural, intracerebral, intra-arterial, intraperitoneal, oral, intralymphatic, intranasal, rectal or vaginal administration, by perfusion through a regional catheter, or by direct intralesional injection. In a preferred embodiment, the compositions of the invention are administered by intravenous push or intravenous infusion given over defined period (e.g., 0.5 to 2 hours). The compositions of the invention can be delivered by peristaltic means or in the form of a depot, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. In particular embodiments, the route of administration is via bolus or continuous infusion over a period of time, once or twice a week. In other particular embodiments, the route of administration is by subcutaneous injection given in one or more sites (e.g. thigh, waist, buttocks, arm), optionally once or twice weekly. In one embodiment, the compositions, and/or methods of the invention are administered on an outpatient basis.

In certain embodiments, the dose of a composition comprising anti-FAP antibody is measured in units of mg/kg of patient body weight. In other embodiments, the dose of a composition comprising anti-FAP antibody is measured in units of mg/kg of patient lean body weight (i.e., body weight minus body fat content). In yet other embodiments, the dose of a composition comprising anti-FAP antibody is measured in units of mg/m$^2$ of patient body surface area. In yet other embodiments, the dose of a composition comprising anti-FAP antibody is measured in units of mg per dose administered to a patient. Any measurement of dose can be used in conjunction with the compositions and methods of the invention and dosage units can be converted by means standard in the art.

Those skilled in the art will appreciate that dosages can be selected based on a number of factors including the age, sex, species and condition of the subject (e.g., activity of autoimmune disease or disorder), the desired degree of cellular or autoimmune antibody depletion, the disease to be treated and/or the particular antibody or antigen-binding fragment being used and can be determined by one of skill in the art. For example, effective amounts of the compositions of the invention may be extrapolated from dose-response curves derived from in vitro test systems or from animal model (e.g. the cotton rat or monkey) test systems. Models and methods for evaluation of the effects of antibodies are known in the art (Wooldridge et al., Blood, 89(8): 2994-2998 (1997), incorporated by reference herein in its entirety). In certain embodiments, for a particular disease or disorder, therapeutic regimens standard in the art for antibody therapy can be used with the compositions and methods of the invention.

Examples of dosing regimens that can be used in the methods of the invention include, but are not limited to, daily, three times weekly (intermittent), weekly, or every 14 days. In certain embodiments, dosing regimens include, but are not limited to, monthly dosing or dosing every 6-8 weeks. Those skilled in the art will appreciate that dosages are generally higher and/or frequency of administration greater for initial treatment as compared with maintenance regimens.

CARs

The present invention provides a chimeric antigen receptor (CAR) comprising an extracellular and intracellular domain. The extracellular domain comprises a target-specific binding element otherwise referred to as an antigen binding domain. In some embodiments, the extracellular domain also comprises a hinge domain. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The present invention includes retroviral and lentiviral vector constructs expressing a CAR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the CAR.

Preferably, the CAR comprises an extracellular domain, a transmembrane domain and a cytoplasmic domain. The extracellular domain and transmembrane domain can be derived from any desired source of such domains. In one embodiment, the CAR comprises a nucleic acid sequence comprising SEQ ID NO: 1. In one embodiment, the CAR comprises an amino acid sequence encoded by a nucleic acid sequence comprising SEQ ID NO: 1.

Antigen Binding Domain

The extracellular domain may be obtained from any of the wide variety of extracellular domains or secreted proteins associated with ligand binding and/or signal transduction. In one embodiment, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

The present invention comprises an antigen binding domain that binds to a stromal cell antigen. As discussed elsewhere herein, the present invention provides that targeting of the stromal cells existing in the in the tumor microenvironment allows for the reduction and/or elimination of the tumor. In one embodiment, the antigen binding domain comprises a domain directed to FAP. FAP is expressed on a vast majority of stromal cells in many types of human carcinomas. In one embodiment, the CAR may be one for which a specific monoclonal antibody currently exists or can be generated in the future. The tumor may be of any type, wherein the tumor microenvironment includes stromal cells. In one embodiment, the tumor is a carcinoma.

In one embodiment, the retroviral or lentiviral vector comprises a CAR designed to be directed to FAP by way of engineering an anti-FAP domain into the CAR. In another embodiment, the template for the RNA CAR is designed to be directed to FAP by way of engineering an anti-FAP domain into the CAR. The CAR of the invention can be engineered to include any anti-FAP moiety that is specific to FAP. The antigen binding domain can be any domain that binds to the antigen including but not limited to monoclonal antibodies, polyclonal antibodies, synthetic antibodies, scFvs, human antibodies, humanized antibodies, and fragments thereof. In one embodiment, the antigen binding domain comprises a nucleic acid sequence comprising SEQ ID NO: 3. In one embodiment, the antigen binding domain comprises an amino acid sequence encoded by a nucleic acid sequence comprising SEQ ID NO: 3.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. In one embodiment, the transmembrane domain comprises a nucleic acid sequence comprising SEQ ID NO: 5. In one embodiment, the transmembrane domain comprises an amino acid sequence encoded by a nucleic acid sequence comprising SEQ ID NO: 5.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In yet another embodiment, the cytoplasmic domain is designed to comprise the signaling domain of CD3-zeta and the signaling domain of CD28 and 4-1BB.

In one embodiment, the cytoplasmic domain comprises a nucleic acid sequence comprising SEQ ID NO: 6. In one embodiment, the cytoplasmic domain comprises a nucleic acid sequence comprising SEQ ID NO: 7. In one embodiment, the cytoplasmic domain comprises a nucleic acid sequence comprising SEQ ID NO: 6 and SEQ ID NO: 7

In one embodiment, the cytoplasmic domain comprises an amino acid sequence encoded by a nucleic acid sequence comprising SEQ ID NO: 6. In one embodiment, the cytoplasmic domain comprises an amino acid sequence encoded by a nucleic acid sequence comprising SEQ ID NO: 7. In one embodiment, the cytoplasmic domain comprises an amino acid sequence encoded by a nucleic acid sequence comprising SEQ ID NO: 6 and SEQ ID NO: 7.

Vectors

The present invention encompasses a DNA construct comprising the sequence of a CAR, wherein the sequence comprises the nucleic acid sequence of an antigen binding domain operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the invention comprises anti-FAP, human CD8 hinge and transmembrane domain, and 4-1BB and CD3zeta signaling domains. In one embodiment, the sequence of the DNA construct comprises SEQ ID NO: 1.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In one embodiment, the genetically modified T cells of the invention are modified through the introduction of RNA. In one embodiment, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. For example, the template for the RNA CAR comprises an extracellular domain comprising a FAP binding domain; a transmembrane domain comprising the hinge and transmembrane domain of CD8α; and a cytoplasmic domain comprises the signaling domain of CD3-zeta and the signaling domain of 4-1BB.

In one embodiment, the DNA to be used for PCR contains an open reading frame. The DNA can be from a naturally occurring DNA sequence from the genome of an organism.

In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, t is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841 A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and U.S. Pat. No. 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2-}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^-$, $CD4^+$, $CD8^-$, $CD45RA^+$, and $CD45RO^-$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^-$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^-$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) modified to express a CAR that combines an FAP binding domain with an intracellular domain of CD3-zeta, CD28, 4-1BB, or any combinations thereof. Therefore, in some instances, the modified T cell can elicit a CAR-mediated T-cell response.

The invention provides the use of a CAR to redirect the specificity of a primary T cell to a stromal cell antigen. Thus, the present invention also provides a method for stimulating a T cell-mediated immune response to a population of stromal cells within a tumor microenvironment in a mammal comprising the step of administering to the mammal a T cell that expresses a CAR, wherein the CAR comprises a binding moiety that specifically interacts with a predetermined stromal cell antigen, a zeta chain portion comprising for example the intracellular domain of human CD3zeta, and a costimulatory signaling region.

In one embodiment, the present invention includes a type of cellular therapy where T cells are genetically modified to express a CAR and the CAR T cell is infused to a recipient in need thereof. The infused cell is able to reduce tumor burden in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, CAR T cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the response elicited by the CAR-modified T cells may be an active or a passive immune response. In addition, the CAR mediated immune response may be part of an adoptive immunotherapy approach in which CAR-modified T cells induce an immune response specific to the antigen binding domain in the CAR. For example, a FAP-CAR T cells elicits an immune response specific against cells expressing FAP.

While the data disclosed herein specifically disclose a CAR comprising an anti-FAP binding domain, along with 4-1BB and CD3zeta signaling domains, the invention should be construed to include any number of variations for each of the components of the construct as described elsewhere herein. That is, the invention includes the use of any stromal cell antigen binding domain in the CAR to generate a CAR-mediated T-cell response specific to the antigen binding domain.

As described elsewhere herein, the present invention provides the targeting of stromal cells which exist in the tumor microenvironment to treat cancers. As such, the present invention includes the treatment of any cancer where stromal cells exist. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the CAR-modified T cells of the invention.

In one embodiment, the T cells modified to express a CAR directed against a stromal cell antigen (e.g. FAP) is administered as monotherapy. However, in another embodiment, the T cells modified to express a CAR directed against a stromal cell antigen are administered in a combination therapy. For example, in one embodiment, the stromal cell directed CAR T cells are administered to a mammal along with T cells modified to express a tumor-directed CAR, wherein the tumor-directed CAR comprises an antigen binding domain that targets any tumor antigen.

In one embodiment, the T cells modified to express a CAR directed against a stromal cell antigen (e.g. FAP) is administered as combination therapy along with an antitumor vaccine as disclosed elsewhere herein.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. Strategies for CAR T cell dosing and scheduling have been discussed (Ertl et al, 2011, Cancer Res, 71:3175-81; Junghans, 2010, Journal of Translational Medicine, 8:55).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Adoptive Transfer of Chimeric Antigen Receptor Expressing T Cells to Diminish Fibroblast Activation Protein Expressing Tumor Stromal Cells Human T Cells Targeting Mouse FAP have been Produced A hybridoma producing an anti-mouse FAP antibody (clone 73.3) was generated. The immunoglobulin heavy and light chains were sequenced and inserted into a set of plasmid cassettes that contained 2 tandem signaling domains: 4-1BB and CD3-zeta.

Figure 2:
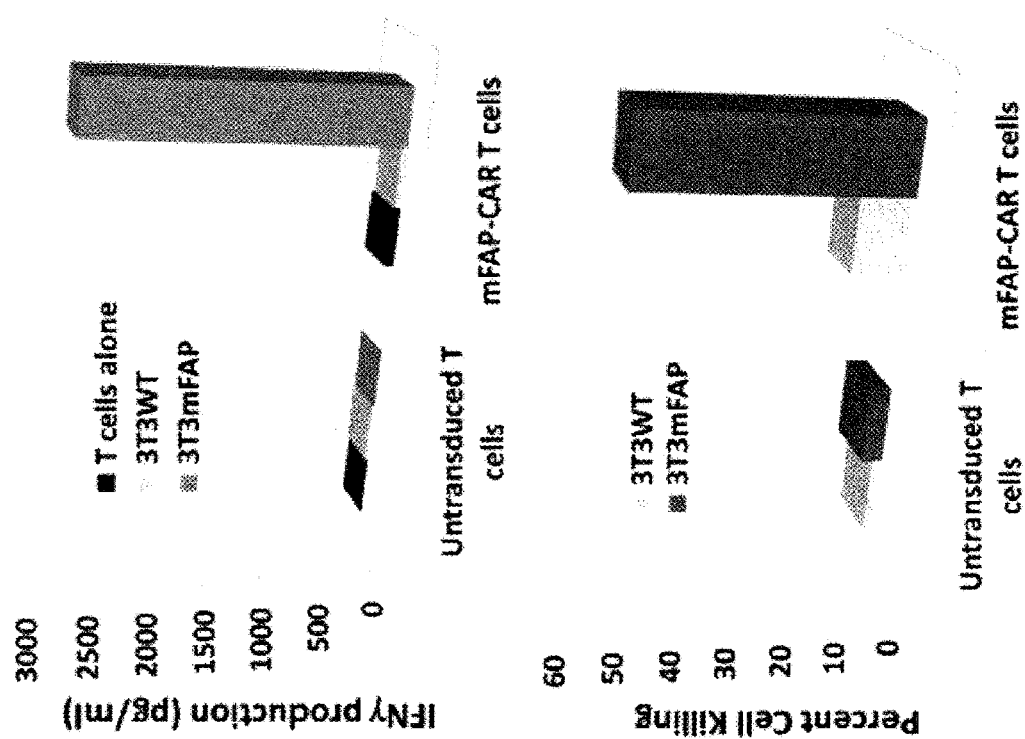
FIG. 2 is a set of graphs depicting the results of experiments demonstrating the specificity of mFAP-CAR T cells. The upper panel depicts the amount of IFN-γ production of untransduced and mFAP-CAR transduced T cells alone and upon exposure to 3T3 wildtype (WT) or 3T3mFAP cells. The lower panel depicts the percent killing of untransduced and mFAP-CAR transduced killing upon co-culture with 3T3WT or 3T3mFAP cells.

A lentiviral vector with the murine (m) mFAP-CAR construct was constructed and transduced into human T cells that were then evaluated for the level of expression of the CAR and the ability to secrete cytokines and specifically kill FAP expressing cells. FIG. 2 compares the response of untransduced T cells and T cells transduced with the FAP construct (mFAP-CAR T cells). The T cells were reacted for 4 hours at an effector (T cell) to target (fibroblasts) ratio of 10:1 with either wild type (WT) 3T3 cells (mouse fibroblasts that do not express FAP) or 3T3 cells transduced to express murine FAP (3T3mFAP). The untransduced T cells alone and mixed with WT 3T3 or 3T3mFAP cells and mFAP-CAR-T cells alone or mixed with WT 3T3 all expressed undetectable or negligible levels of IFN-γ while mFAP-CAR-T cells interacted with 3T3mFAP cells produced high levels of IFN-γ (FIG. 2, upper panel). Similarly, specific cytoxicity by mFAP-CAR T cells of 3T3mFAP cells was induced (FIG. 2, lower panel). These data show that mFAP-CAR human T cells selectively and efficiently released IFN-γ and killed FAP-expressing cells but not FAP-negative 3T3 fibroblasts in vitro.

Mouse T Cells Targeting Mouse FAP have been Produced

Figure 3:
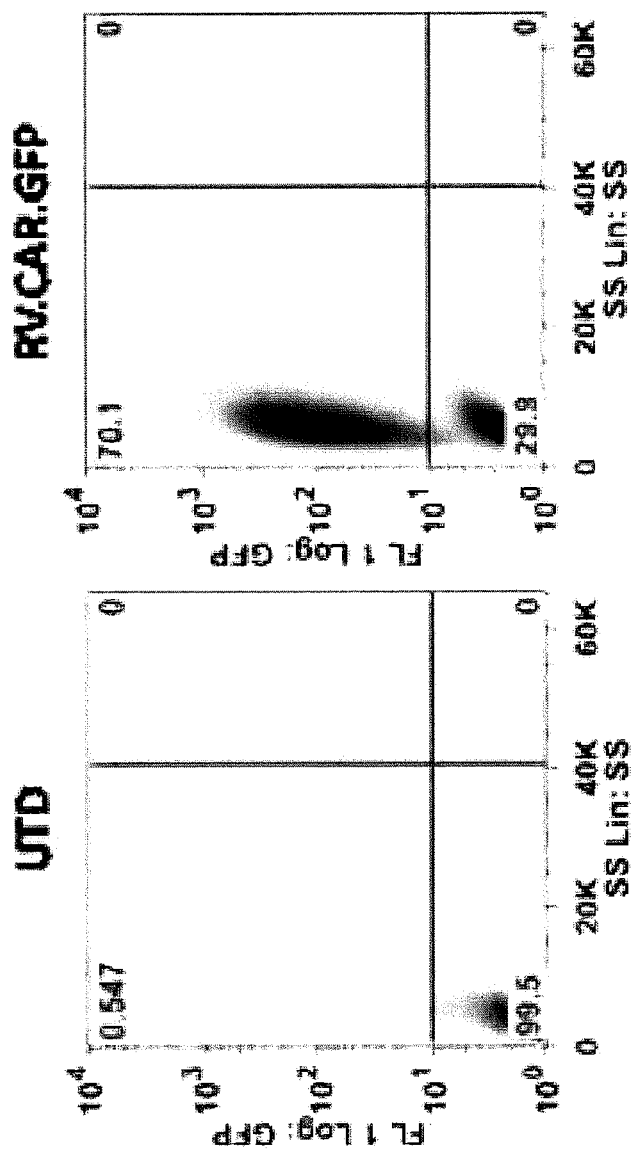
FIG. 3 is a set of graphs depicting the results of experiments demonstrating the expression of mFAP-CAR (right panel), compared to untransduced control (left panel).

As lentiviral transduction is not effective for mouse T cells, available protocols were adapted (Lee et al., 2009, Methods Mol Biol, 506: 83-96; Zhong et al., 2010, J Vis Exp, 44: 2307) to achieve high transduction rates using retroviral transduction. Accordingly, mouse T cells were transduced with the mFAP-CAR-GFP retroviral vector. As shown in FIG. 3, transgene expression was observed in more than 70% of cells three days after transduction (with no selection) based on detection of GFP+ cells by FACS of untransduced (UTD) vs. RV.CAR-GFP transduced cells (right panel). Similar results were seen when cells were stained with an antibody that recognizes the scFv portion of the CAR proving surface expression. Thirty million CAR+ T cells are routinely generated per donor spleen.

Figure 4:
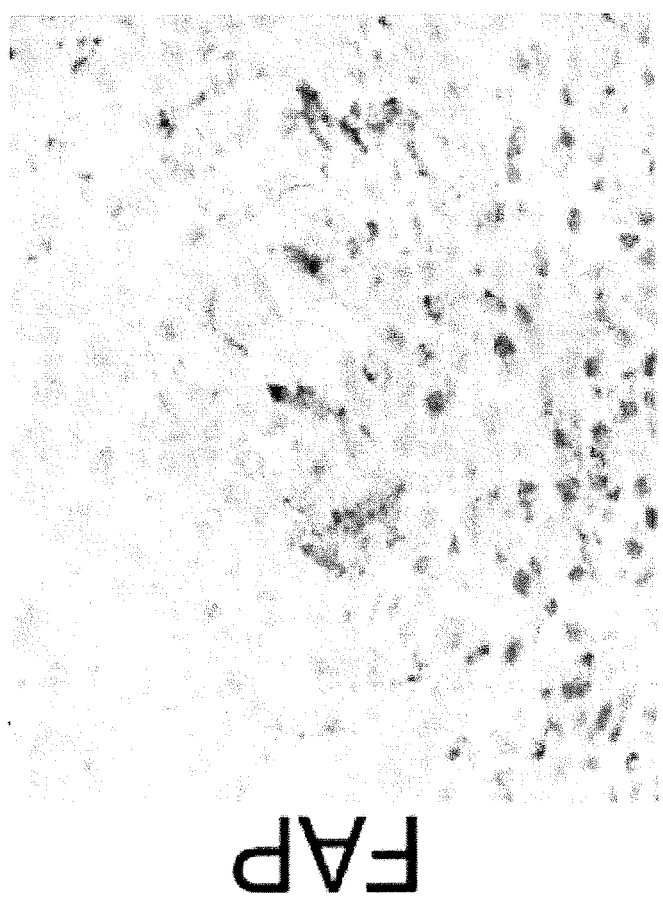
FIG. 4 is an image depicting the presence of FAP in a mouse mesothelioma (AE17) tumor.

Anti-Tumor Activity of FAP-CAR T in Mouse Models:

A syngeneic transplant model of the mesothelioma AE17 (AE17) in immunocompetent mice was used to test the anti-tumor activity of mFAP-CAR T cells in vivo. An important feature of this model is that the tumors become infiltrated with FAP+ fibroblasts. FIG. 4 shows a mouse tumor stained with anti-FAP antibody. This figure shows that host fibroblasts infiltrate the tumors and that the FAP+ cells can be easily identified by immunostaining.

Figure 5:
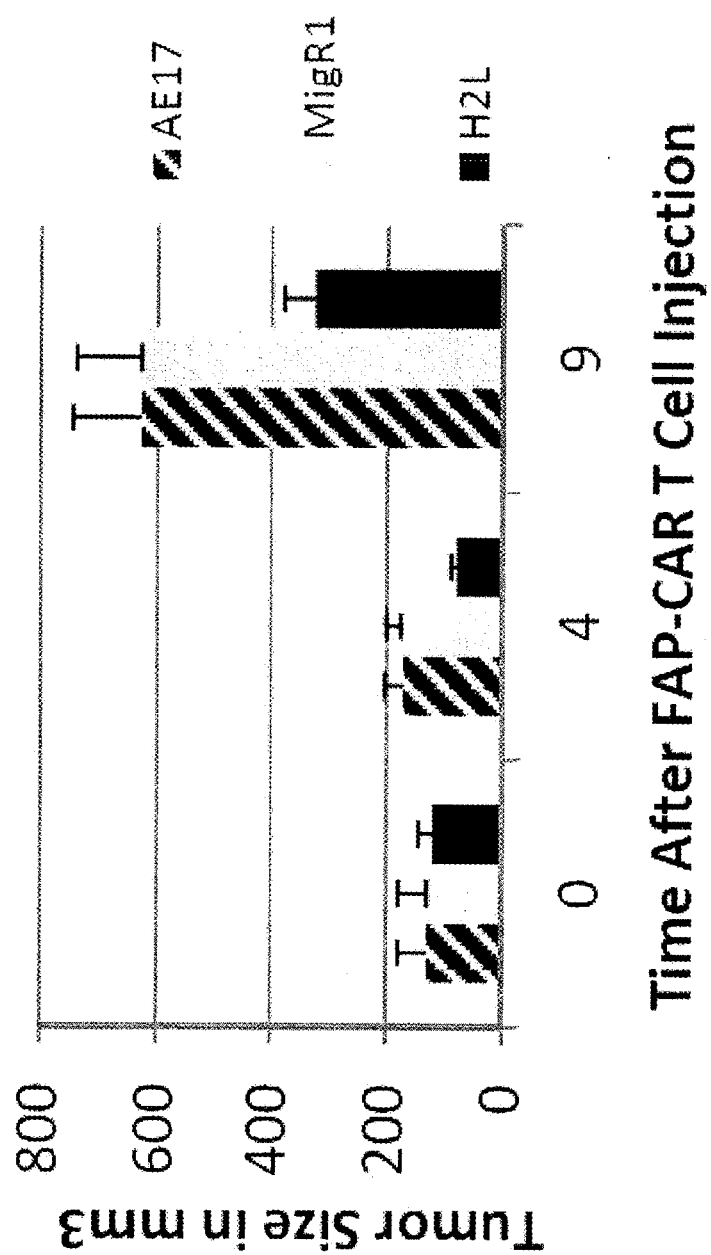
FIG. 5 is a graph depicting tumor size after 0, 4, and 9 days after intravenous injection of saline (AE17), $10^7$ mouse T cells transfected with a retrovirus encoding GFP (MigR1) or $10^7$ mouse T cells transfected with mFAP-CAR (H2L).

A study was then conducted to establish the safety and feasibility of the FAP-CAR approach. Mouse AE17 cells were injected into the flanks of B6 mice and allowed to grow to 150 mm$^3$ in size. The mice were injected intravenously with saline (AE17), with 10$^7$ mouse T cells transfected with a retrovirus encoding GFP (MigR1) or with 10$^7$ mouse T cells transfected with mFAP-CAR (H2L) (all were at 60% transfection efficiency). FIG. 5 shows the tumor sizes 9 days after injection. This single dose of mouse FAP-CAR T cells clearly inhibited tumor growth. Importantly, no toxicity in the mice was noted. These data demonstrate that mFAP-CAR T cells can inhibit tumor growth without obvious toxicity.

Figure 6:
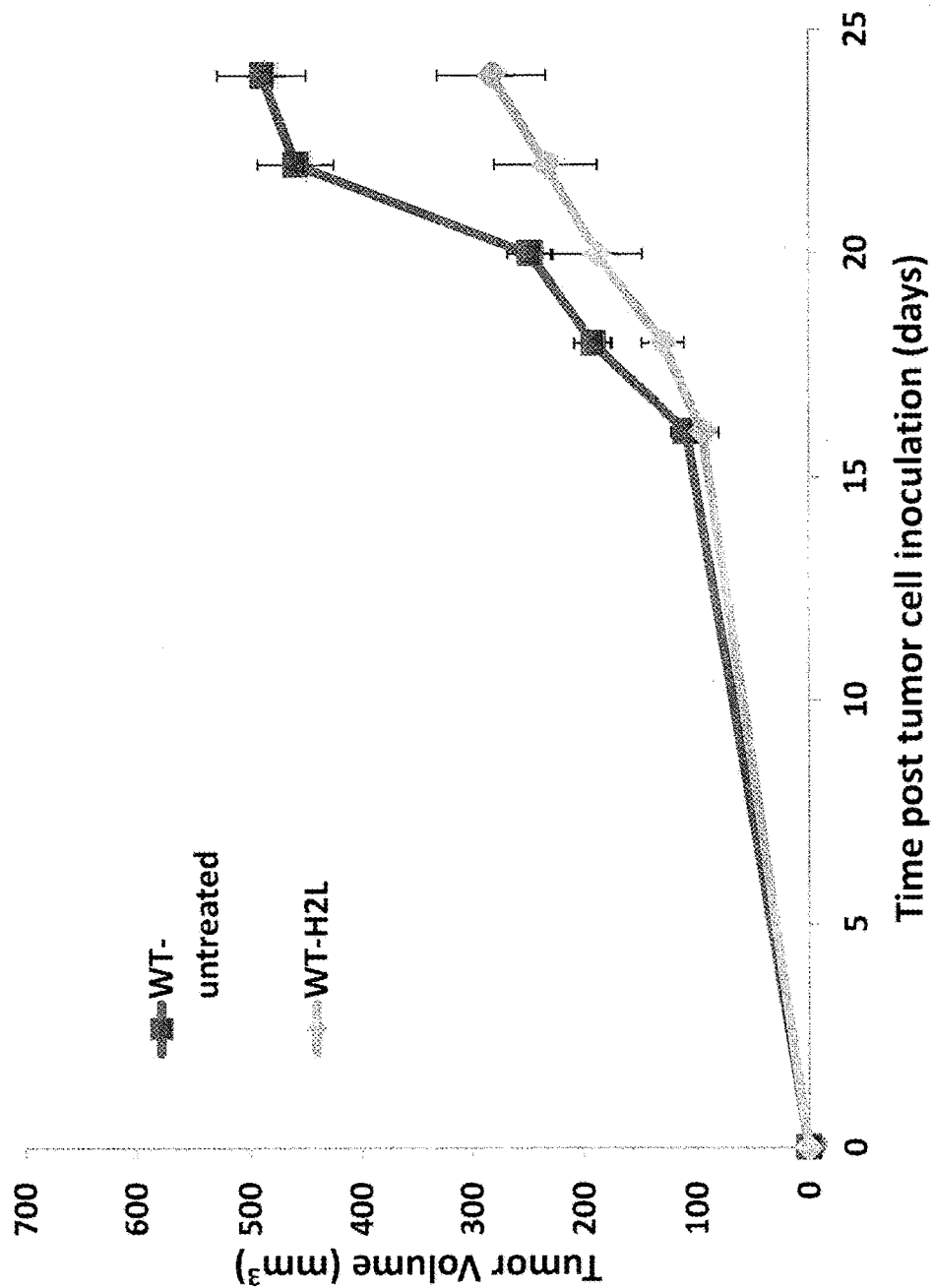
FIG. 6 is a graph depicting the results of an experiment assessing tumor size before and after intravenous injection of saline (WT-untreated) or $10^7$ human T cells transfected with a lentivirus encoding mFAP-CAR (WT-H2L).

A study was conducted to show the safety and feasibility of the FAP CAR approach using human T cells. Human lung cancer cells (A549) were injected into the flanks of immunodeficient mice and allowed to grow to 100 mm$^3$ in size. The mice were injected intravenously with saline (untreated, or with 10$^7$ human T cells transfected with a lentivirus expressing mFAP-CAR (WT-H2L). FIG. 6 shows the tumor sizes before and after injection (arrow). This single dose of human T cells expressing mouse FAP-CAR clearly inhibited tumor growth. Importantly, no toxicity in the mice was noted. These data demonstrate that mFAP-CAR in human T cells can inhibit tumor growth without obvious toxicity.

Figure 7:
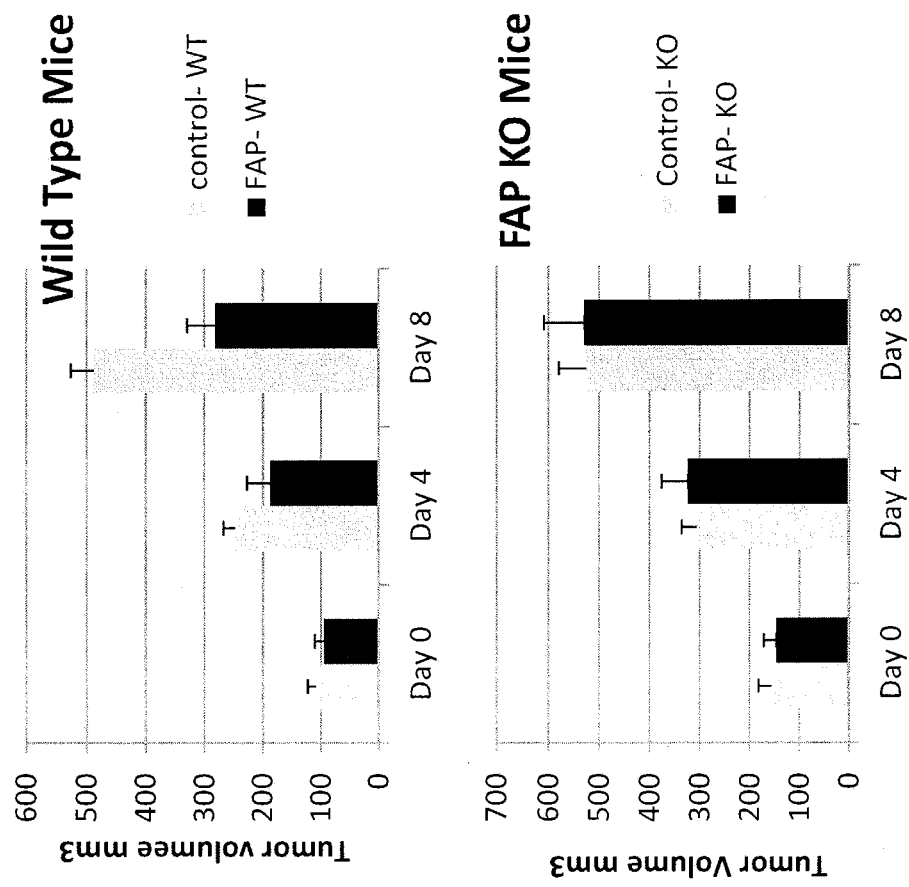
FIG. 7 is a graph depicting the results of an experiment assessing tumor size after treatment with unmodified control T cells (control) or FAP-CAR T cells (FAP). T cells were injected into WT-B6 mice (upper panel) or Knock Out Mice lacking expression of FAP (lower panel).

Another study was performed to examine FAP-CAR T cell specificity. Tumor cells were injected into wild type mice or FAP-Knockout mice as above and treated with 10$^7$ control T cells or with 10$^7$ FAP-CAR T cells. FIG. 7 shows the tumor sizes at the time of injection (Day 0) and at 4 and 8 days after injection. While FAP-CAR T cells slowed tumor growth in wild type mice (upper panel), all activity was lost in the FAP KO mice. These data show that mFAP-CAR T cells can inhibit tumor growth without obvious toxicity in mice and in a FAP-specific fashion (all activity was lost in FAP-KO mice).

As described herein, mFAP-CAR T cells have been developed that are specifically activated by FAP expressing stromal cells in vitro and exhibit anti-tumor activity in vivo. It is demonstrated that mFAP-CAR T cells are specifically activated by and kill FAP expressing stromal cells and have anti-tumor activity in a mouse model of cancer with no obvious toxicity.

Human T Cells Targeting Human-FAP have been Produced.

In a similar fashion as above, an anti-human FAP construct is optimized. The light and heavy chains of the well-characterized F19 anti-human FAP monoclonal (the same antibody used to stain human lung cancer in FIG. 2) from hybridoma cells has been sequenced and inserted into the CD3-zeta:41BB "double activation domain" construct. Human T cells are transduced with a humanFAP-CAR construct thereby allowing specific targeting of human FAP.

The FAP-CAR approach presented herein is further evaluated by way of additional experiments. The specificity and anti-tumor activity of mouse and human FAP-CAR-T cells in human tumor xenografts in immunoincompetent mice is examined. Further animal and human studies are performed to examine the ability of FAP-CAR T cells to inhibit metastasis. Additional studies are done to evaluate FAP-CAR T cells administered both as a monotherapy and also as a combined therapy along with tumor-directed CARs to observe any additive or synergistic effects. Studies presented herein provide avenues to understand the mechanisms by which deletion of FAP+ stromal cells inhibit primary tumor growth.

Example 2: Sequence of the mFAP-CAR

Figure 8:
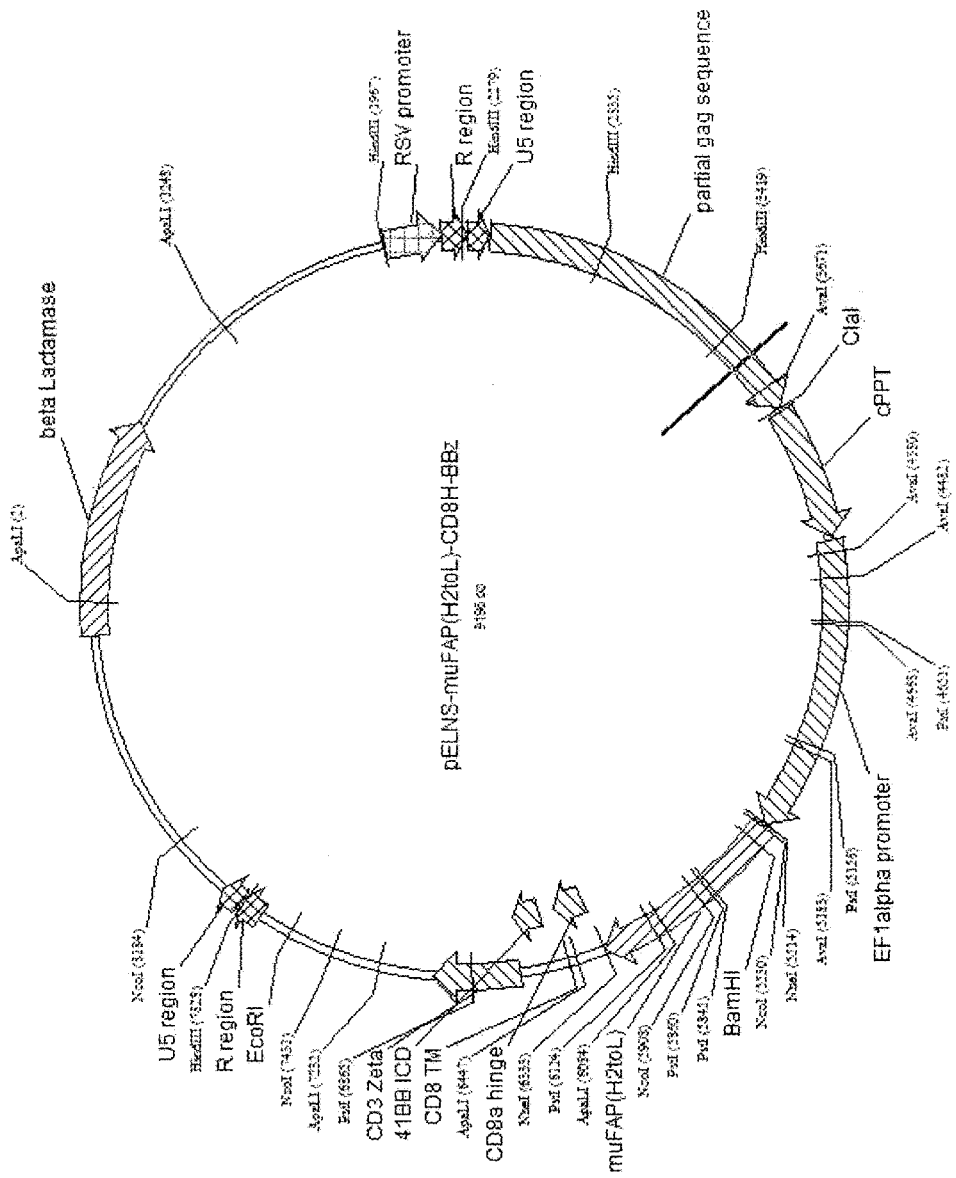
FIG. 8 is a schematic depicting an exemplary vector encoding a FAP-CAR of the invention.

A vector map of the vector, pELNS-muFAP(H2toL)-CD8H-BBz, is shown in FIG. 8. The nucleic acid sequence of the mFAP-CAR (SEQ ID NO: 1) and of individual domains within the CAR are provided.

mFAP-CAR
(SEQ ID NO: 1)
atggccctgcctgtgacagccctgctgctgcctctggctctgctgctgca tgccgctagacctggatcccaggtgcagctgaaagagtccggcggaggac tggtgcagcctggcggatctctgaagctgagctgtgctgccagcggatca ccttcagcagctacggcatgagctgggtgcgacagaccgccgacaagaga ctggaactggtggctaccaccaacaacaacggcggcgtgacctactaccc cgacagcgtgaagggcagattcaccatctccagagacaacgccaagaaca ccctgtacctgcagatgagcagcctgcagagcgaggacaccgccatgtac tactgcgccagatacggctactacgccatggattactggggccagggcat cagcgtgaccgtgtctagcggaggcggcggatctggcggaggggatcta gtggcggaggctctgacgtgctgatgacccagacacctctgagcctgcca gtgtccctgggcgaccaggccagcatcagctgtagaagcagccagagcat cgtgcacagcaacggcaacacctacctggaatggtatctgcagaagcccg gccagagccccaagctgctgatctacaaggtgtccaacagattcagcggc gtgcccgacagattctccggcagcggctctggcaccgacttcaccgtgaa gatctccagggtggaagccgaggacctgggcgtgtactactgttttcaag gcagccacgtgccctacaccttcggcggaggcaccaagctggaaatcaag gctagctccggaaccacgacgccagcgccgcgaccaccaacaccggcgcc caccatcgcgtcgcagcccctgtccctgcgcccagaggcgtgccggccag cggcggggggcgcagtgcacacgaggggctggacttcgcctgtgatatc tacatctgggcgccttggccgggacttgtgggtccttctcctgtcact ggttatcaccctttactgcaaacggggcagaaagaaactcctgtatatat tcaaacaaccatttatgagaccagtacaaactactcaagaggaagatggc tgtagctgccgatttccagaagaagaagaaggaggatgtgaactgagagt gaagttcagcaggagcgcagacgccccgcgtacaagcagggccagaacc agctctataacgagctcaatctaggacgaagagaggagtacgatgtttg gacaagagacgtggccgggaccctgagatggggggaaagccgagaaggaa gaaccctcaggaaggcctgtacaatgaactgcagaaagataagatggcgg aggcctacagtgagattgggatgaaaggcgagcgccggaggggcaaggggg cacgatggcctttaccagggtctcagtacagccaccaaggacacctacga cgccttcacatgcaggccctgcccctcgc CD8 leader sequence
(SEQ ID NO: 2)
atggccctgcctgtgacagccctgctgctgcctctggctctgctgctgca
tgccgctagacct Anti-mFAP scFv
(SEQ ID NO: 3)
caggtgcagctgaaagagtccggcggaggactggtgcagcctggcggatc tctgaagctgagctgtgctgccagcggcttcaccttcagcagctacggca tgagctgggtgcgacagaccgccgacaagagactggaactggtggctacc accaacaacaacggcggcgtgacctactacccccgacagcgtgaagggcag attcaccatctccagagacaacgccaagaacaccctgtacctgcagatga gcagcctgcagagcgaggacaccgccatgtactactgcgccagatacggc tactacgccatggattactggggccagggcatcagcgtgaccgtgtctag cggaggcggcggatctggcggaggggatctagtggcggaggctctgacg tgctgatgacccagacacctctgagcctgccagtgtccctgggcgaccag gccagcatcagctgtagaagcagccagagcatcgtgcacagcaacggcaa cacctacctggaatggtatctgcagaagcccggccagagccccaagctgc tgatctacaaggtgtccaacagattcagcggcgtgcccgacagattctcc ggcagcggctctggcaccgacttcaccgtgaagatctccagggtggaagc cgaggacctgggcgtgtactactgttttcaaggcagccacgtgccctaca ccttcggcggaggcaccaagctggaaatcaag CD8α hinge
(SEQ ID NO: 4)
accacgacgccagcgccgcgaccaccaacaccggcgccaccatcgcgtc
gcagcccctgtccctgcgcccagaggcgtgccggccagcggcggggggcg
cagtgcacacgaggggctggacttcgcctgtgat CD8α transmembrane domain
(SEQ ID NO: 5)
atctacatctgggcgccatggccgggacttgtgggtccttctcctgtca
ctggttatcacccttactgc 4-1BB intracellular domain
(SEQ ID NO: 6)
aaacggggcagaaagaaactcctgtatatattcaaacaaccatttatgag
accagtacaaactactcaagaggaagatggctgtagctgccgatttccag
aagaagaagaaggaggatgtgaactg CD3-zeta signaling domain
(SEQ ID NO: 7)
Agagtgaagttcagcaggagcgcagacgccccgcgtacaagcagggcca gaaccagctctataacgagctcaatctaggacgaagagaggagtacgatg ttttggacaagagacgtggccgggaccctgagatggggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgccttcacatgcaggccctgccccctcgc

Example 3: CAR T Cells Targeting FAP in the Tumor Stroma have Antitumor Efficacy and Augment Host Immunity Without Toxicity As described elsewhere herein and in the present Example, a single chain Fv specific for mouse FAP was expressed in a retroviral CAR construct containing a CD8α hinge and transmembrane regions and human CD3Z and 4-1BB activation domains. Retrovirally-transduced muFAP-CAR mouse T cells secreted IFNy and killed FAP-expressing 3T3 target cells, but did not react with FAP-negative parental 3T3 cells. Adoptively transferred FAP-CAR mouse T cells reduced the number of FAP+ stromal cells and inhibited growth of multiple types of subcutaneously transplanted tumors in wild-type, but not FAP-null immune-competent syngeneic mice. The anti-tumor effects could be augmented by multiple injections of T cells, by using T cells with enhanced anti-tumor activity due to the loss of diacylglycerol kinase, or by combination with a vaccine. A major mechanism of action was augmentation of endogenous CD8+ T cell anti-tumor responses. Importantly, off-tumor toxicity was minimal following muFAP-CAR T cell therapy. Therefore, inhibiting tumor growth by targeting tumor stroma with adoptively transferred CAR T cells directed to FAP has been discovered in the present invention to be a feasible, safe, and effective antitumor therapy.

The anti-FAP scFv used herein is different from that used in prior art studies in that the antibody comprises both human and murine cytoplasmic domains. The data presented herein establish clear anti-tumor efficacy in multiple tumor models, evidence of activation of endogenous immune responses, and success in combining the CAR T cells with a tumor vaccine. Importantly, using the CAR constructs of the present invention, minimal toxicity was apparent, with no accompanying anemia or weight loss.

The Materials and Methods used in the experiments described in this Example are now described.

Cell Lines

Figures 9A, 9B, 9C, 9D, 9E:
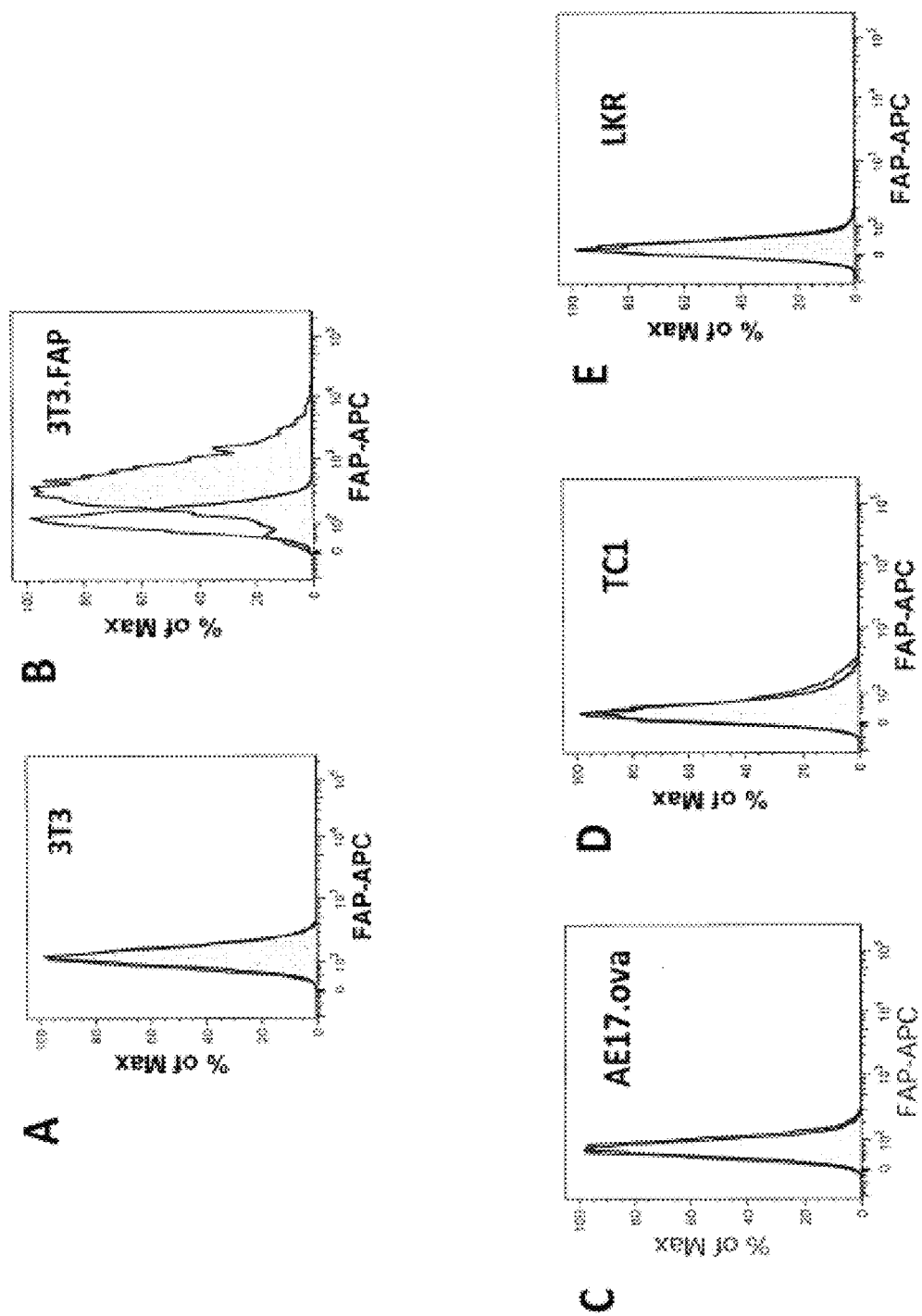
FIG. 9A depicts flow cytometric analysis of FAP expression in parental 3T3 fibroblasts.
FIG. 9B depicts flow cytometric analysis of FAP expression in 3T3.FAP fibroblasts.
FIG. 9C depicts flow cytometric analysis of FAP expression in AE17.ova mouse mesothelioma cells.
FIG. 9D depicts flow cytometric analysis of FAP expression in TC1 mouse lung cancer cells.
FIG. 9E depicts flow cytometric analysis of FAP expression in LKR mouse lung cancer cells.

Mouse AE17.ova mesothelioma cells (expressing chicken ovalbumin) were used (Jackaman et al., 2003J Immunol. 171:5051-63). TC1 lung cancer cells were derived from mouse lung epithelial cells immortalized with human papillomavirus HPV-16 E6 and E7 and transformed with the c-Ha-ras oncogene (Lin et al., 1996, Cancer Res 56:21-6). The mouse "LKR" cell line was derived from an explant of a pulmonary tumor from an activated K-ras$^{G12\sigma}$ mutant mouse generated as described in Johnson et al., 2001, Nature 410:1111-6. Mouse 4T1 mammary carcinoma, CT26 colon cancer cells and 3T3Balb/C cells, were purchased from the American Type Culture Collection. Mouse FAP expressing 3T3BALB/C (3T3.FAP) cells were created by lentiviral transduction of the FAP-3T3 parental line with murine FAP (FIGS. 9A and 9B).

Antibodies

Specific antibodies used are described elsewhere herein.

Generation of 73.3 Hybridoma

Figures 10A, 10B, 10C:
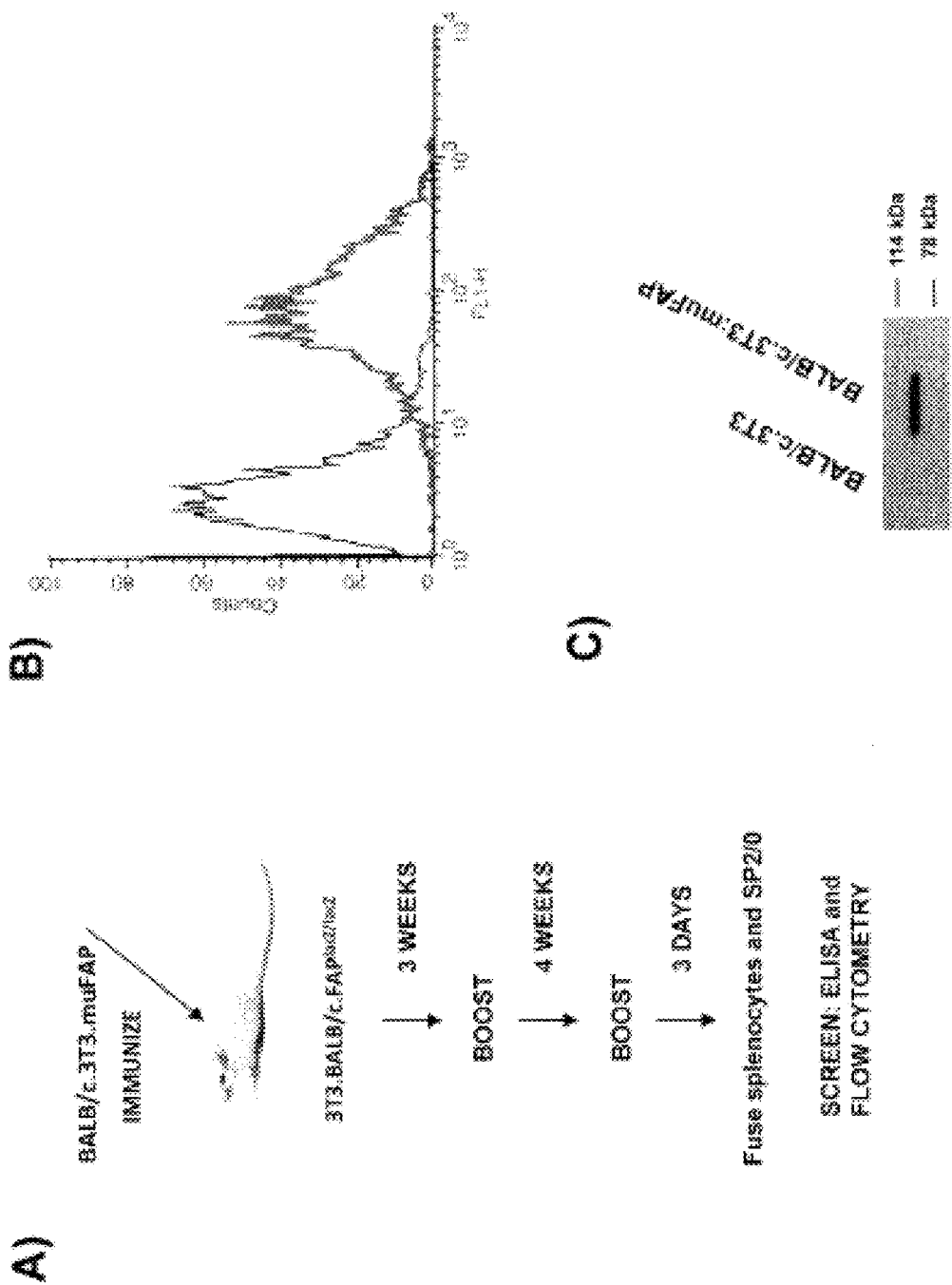
FIG. 10A depicts generation of anti-murine FAPlacZ/lacZ mABs. Mice were immunized with BALB/c3T3 cells transduced with lentivirus encoding full-length muFAP.
FIG. 10B shows FACS of hybridoma supernatants screened by ELISA (not shown) and by flow cytometry of BALB/c3T3.muFAP (right peak) and BALB/c3T3.LacZ cells (left peak), respectively. The reactivity of mAb 73.3 is depicted.
FIG. 10C shows lysates of BALB/c3T3.LacZ cells and BALB/c3T3.muFAP cells subjected to IP using mAb 73.3 followed by immunoblotting with second independent anti-FAP mAb.

FAP-null mice (Niedermeyer et al., 2000, Mol Cell Biol 2000; 20:1089-94), were immunized and twice boosted with FAP+ 3T3 cells intraperitoneally. 72 hours after the final boost, splenocytes were harvested and fused to myeloma cells. Hybridoma supernatants were screened for monoclonal antibodies that reacted specifically with 3T3.FAP and activated primary wild-type fibroblasts but not 3T3 cells or activated primary fibroblasts isolated from FAP-null mice. One mAb, 73.3, with this reactivity profile was purified and further characterized as specific for mouse FAP based on reactivity with purified recombinant mouse FAP extracellular domain (by ELISA and by immunoblotting), its reactivity with a single protein with an apparent molecular weight of approximately 95 kD in protein extracts of FAP+ but not FAP− cells and tissues, and lack of reactivity with cells expressing human FAP (human FAP transduced 3T3 and human foreskin fibroblasts) (FIGS. 10A-10C).

Synthesis of Anti-muFAP CAR Construct.

Figures 11A, 11B, 11C, 11D:
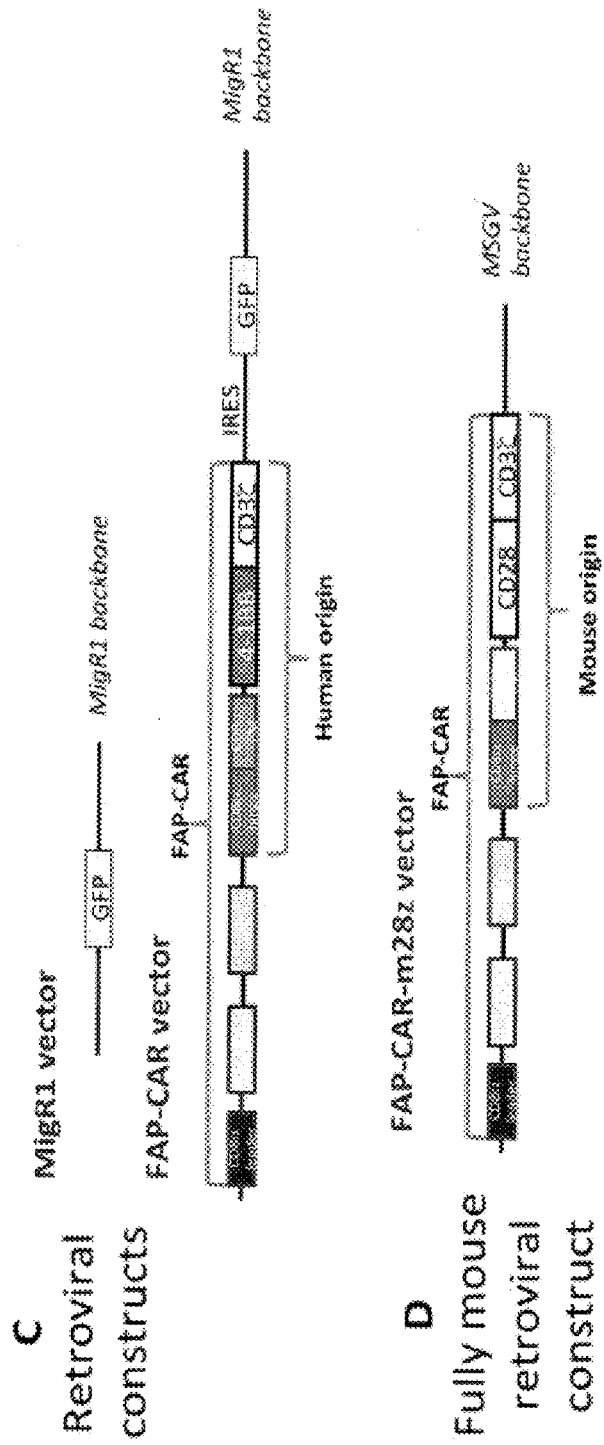
FIG. 11A depicts the structure of FAP-CAR. Total RNA of 73.3 hybridoma was extracted, reverse transcribed to cDNA, and PCR amplified and inserted into cloning vector to obtain the sequence of variable domains of IgG heavy chain (SEQ ID NO: 8)
FIG. 11B depicts the structure of FAP-CAR and light (SEQ ID NO: 9) chains.
FIG. 11C depicts anti-muFAP CAR consisting of the anti-muFAP scFv, CD8α hinge and transmembrane domain, plus 4-1BB and CD3ζ intracellular signaling domains, and was cloned into MigR1 retroviral vector in order to transduce primary mouse T cells.
FIG. 11D depicts a fully mouse FAP-CAR construct, which consists of the anti-muFAP scFv, CD8α hinge and CD28 transmembrane domain, plus CD28 and CD3ζ intracellular signaling domains of mouse origin, and was cloned into MSGV retroviral vector in order to transduce primary mouse T cells.

Total RNA from 73.3 hybridoma cells was isolated and reverse transcribed to cDNA. Variable heavy ($V_H$) and light ($V_L$) chains of 73.3 anti-muFAP antibody were PCR amplified and sequenced (FIGS. 11A and 11B). The VH and VL sequences were fused with a CAR construct comprising CD8a hinge, CD8a transmembrane domain, and two human intracellular signaling domains derived from 4-1BB and CD3Q (Milone et al., 2009, Mol Ther. 17:1453-64). This CAR was then inserted into an IRES containing retroviral MigR1 vector (FIG. 11C) that also expresses green fluorescent protein (GFP) for tracking purposes (Pear et al., 1998, Blood 92(10):3780-92. A fully mouse construct of FAP-CAR, "FAP-CAR-m28Z", was also synthesized by coupling the same 73.3 scFv with the murine CD3Z chain and murine CD28 intracellular signaling domain. This construct was then inserted into another retroviral vector MSGV (FIG. 11D) (Morgan et al., 2012, 23:1043-53). Infective particles were generated from the supernatants of 293T cells transfected with retroviral vector plasmid and helper plasmids using Lipofectamine 2000 (Invitrogen), as described (Lee et al., m, 2009, Methods Mol Biol 506:83-96).

Isolation, Transduction and Expansion of Primary Mouse T lymphocytes

Primary murine splenic T cells were isolated and transduced as described in Riese et al., 2013, Cancer Res 73:3566-77 and elsewhere herein.

Antigen or Antibody Coated Beads

Recombinant FAP-extracellular domain protein (FAP-ECD, bovine serum albumin (Fisher Scientific) or anti-CD3e/anti-CD28 antibodies (eBioscience) were chemically crosslinked to tosylactivated 4.5 ˆm Dynabeads (Invitrogen, #140-13) using the manufacturers' instructions.

Immunoblotting

To assess the function of the FAP-CAR construct, FAP-CAR transduced T cells were incubated either with BSA or FAP-ECD-coated beads (at 2:1 bead to T cell ratio), or with anti-CD3e antibody for 10 min. Lysates were then prepared and immunoblotted for phosphorylated ERK, phosphorylated AKT, phosphorylated IKKa/p, or P-actin.

Cytotoxicity and IFNy ELISA

Parental 3T3 and 3T3.FAP cells were transduced with luciferase as previously described (Moon et al., 2011, Clin. Cancer Res. 17:4719-30. Cytotoxicity assays were performed by co-culture of T cells with target 3T3 cells at the indicated ratios, in triplicate, in 96-well round bottom plates. After 18 hours, the culture supernatants were collected for IFNy analysis using an ELISA (mouse IFNy, BD OpEIA). Cytotoxicity of transduced T cells was determined by detecting the remaining luciferase activity from the cell lysate using as assay described in Riese et al., 2013, Cancer Res. 73:3566-77.

CAR-T Cell Transfer into Mice Bearing Established Tumors

Mice were injected subcutaneously with $2\times10^6$ AE17.ova (C57BL/6 mice), $1\times10^6$ TC1 (C57BL/6 mice), $2\times10^6$ LKR (C57BL/6 crossed with 129 pf/j), $0.5\times10^6$ 4T1 (BALB/c mice), or $1\times10^6$ CT26 (BALB/c mice) tumor cells into the dorsal-lateral flank. Tumor (100-150 mm$^3$)-bearing mice were randomly assigned to receive either FAP-CAR T cells or MigR1-transduced T cells or remained untreated (minimum, five mice per group, each experiment repeated at least once). $1\times10^7$ T cells were administered through the tail vein. Body weight and the tumor size were measured by electronic scales and calipers, respectively. At the end of the experiment, tumors and spleens were harvested for flow cytometric analyses.

Flow Cytometric Analyses

Tumors were harvested 3 and 8 days after adoptive transfer of FAP-CAR T cells to analyze intratumoral cells by flow cytometry (Zhao et al., 2010, Cancer Res. 70:9053-61. Cell acquisition was performed on LSR-II using FACSDiva software (BD Bioscience, USA). Data were analyzed using FlowJo (Tree Star).

Statistical Analyses

For flank tumor studies comparing two groups, the student t test was used. For comparisons of more than two groups, we used one-way ANOVA with appropriate post hoc testing. Differences were considered significant when p<0.05. Data are presented as mean+/−SEM.

The Results of the experiments disclosed in this Example are now described.

In Vitro Evaluation of Mouse FAP-CAR T Cells

Figures 12A, 12B, 12C, 12D:
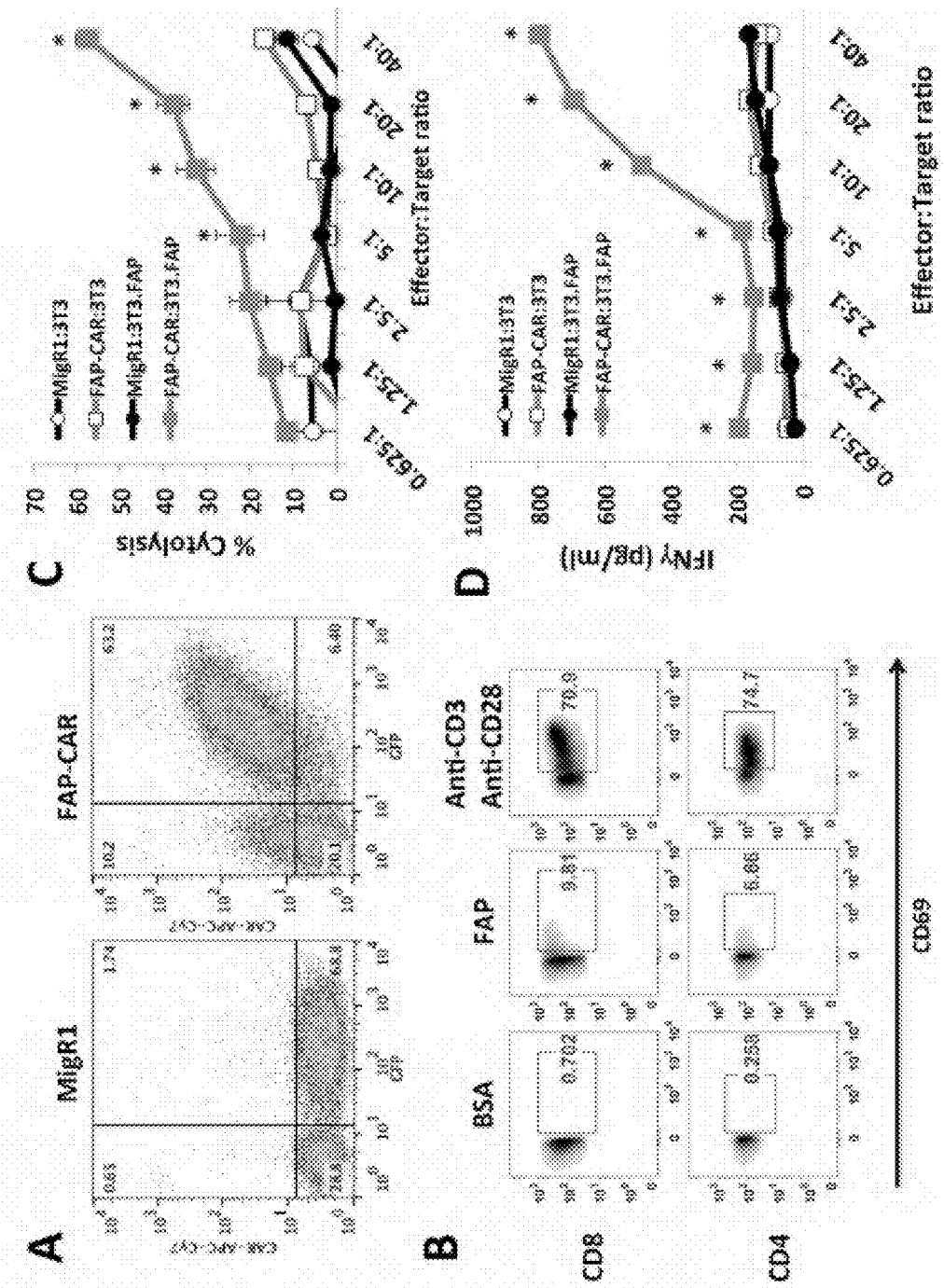
FIG. 12A depicts ex vivo assessment of mouse CART cells redirected against FAP with retroviral transduction of mouse T cells to express GFP (MigR1) or GFP and anti-mFAP-CAR.
FIG. 12B shows the up regulation of CD69 on CAR (GFP)-positive CD8 and CD4 T cells following stimulation with BSA- or FAP-coated beads for 18 hours. T cells were stimulated with anti-CD3/anti-CD28 beads as positive control.
FIG. 12C shows the target-specific cytolytic activity of FAP-CAR T cells.
FIG. 12D shows the IFNγ production of FAP-CAR T cells. Various Effector:Target ratios of MigR1 and FAP-CAR T cells were reacted with parental 3T3 or 3T3.FAP fibroblasts for 18 hours. * Denotes statistical significance between FAP-CAR-treated 3T3.FAP group versus the other 3 group, p value<0.05.

The primary retroviral CAR construct (containing the scFv from anti-murine FAP antibody 73.3 coupled to the human CD3Z and 4-1BB cytoplasmic domains and a control virus expressing only GFP (FIGS. 11A-11D) were used to transduce activated mouse T cells resulting in greater than 60% of T cells expressing GFP (MigR1) or GFP plus FAP-CAR (FIG. 12A).

To verify functionality, mouse T cells expressing FAP-CAR were stimulated for 18 hours with beads coated with either bovine serum albumin (BSA) (negative control), recombinant FAP protein, or anti-CD3/anti-CD28 antibodies (positive control). The FAP-coated beads activated FAP-CAR T cells to increase CD69 expression, however, as expected, to lower levels than that of CD3/CD28. (FIG. 12B).

Figure 13:
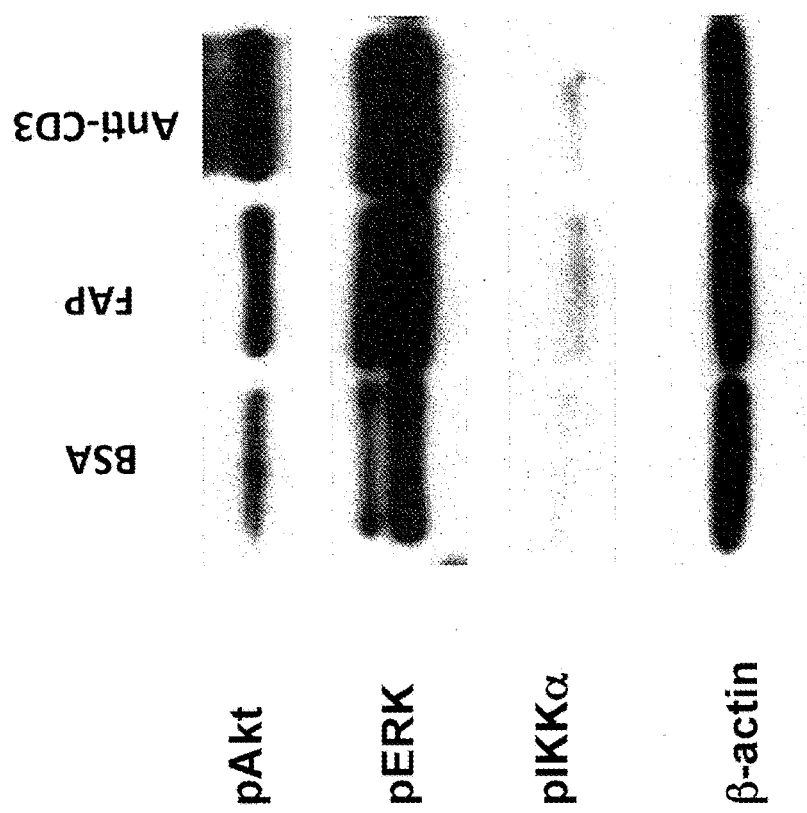
FIG. 13 depicts signaling in FAP CAR T cells. FAP-CAR T cells were exposed either BSA- or FAP-coated beads for 10 min. Cell lysates were then prepared and immunoblotted for phospho-ERK, phospho-AKT, and phospho-IKKα/β. Anti-CD3ε antibody was used as a positive control for T cell activation, and b-actin was immunoblotted to check for equal loading.

To further evaluate intracellular signaling, lysates from bead-stimulated T cells were run on gels and immunoblotted. In comparison to BSA-coated beads, FAP-coated beads induced phosphorylation of AKT, ERK, and IKKa/p in FAP-CAR T cells (FIG. 13).

To assess effector functions, transduced mouse T cells were co-cultured with 3T3 fibroblasts (which do not express FAP) or with 3T3 fibroblasts transduced to express FAP (3T3.FAP) (FIGS. 9A and 9B). After 18 hours, T cells expressing the FAP-CAR construct (but not the control GFP-expressing T cells) effectively killed 3T3.FAP fibroblasts (FIG. 12C) and secreted IFNy (FIG. 12D) in a dose-dependent manner, but had no effect on parental 3T3 cells.

Figure 14:
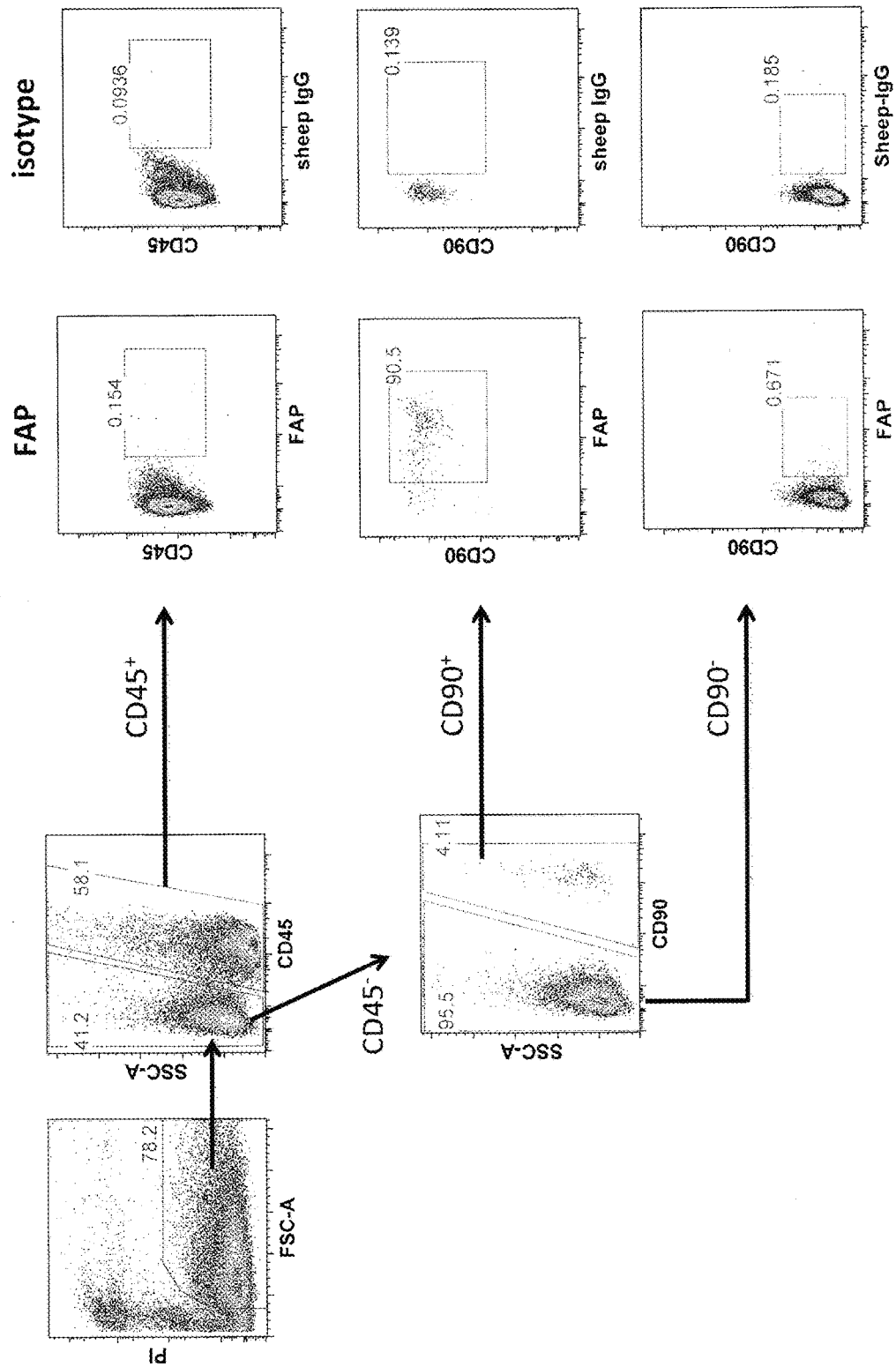
FIG. 14 depicts phenotypic analysis of FAP+ stromal cells in untreated TC1 flank tumors in C57BL/6 mice. Untreated TC1 tumors were harvested and digested with mixture of collagenases to make single cell suspension. Cells were then stained with anti-CD45, anti-CD90 and anti-FAP. Propidium iodide was used to exclude dead cells.

Injection of Mouse FAP-CAR T Cells Reduces Tumor Growth in a FAP-Specific Fashion The capability of FAP-CAR mouse T cells to inhibit growth of tumors was explored using three different tumor lines which do not express FAP (FIG. 9C-9E): AE17.ova mesothelioma cells, TC1 and LKR lung cancer cells. Cells were injected into the flanks of syngenic mice and allowed to form established tumors. The tumors had an easily detectable number of mouse FAP-expressing cells with the majority of the FAP+ cells being CD45⁻/CD90+ stromal cells (~3% of total tumor cells), and only a small minority being CD45+ hematopoietic cells (~0.2% of total tumor cells) (FIG. 20 and FIG. 14).

When tumors reached ~100-200 $mm^{3\prime}$ (10-14 days after tumor cell inoculation), $10^7$ T cells were injected intravenously and tumor measurements made serially. FAP-CAR T cells, but not MigR1 T cells, significantly ($p<0.05$) reduced the growth of TC1 tumors (FIG. 15A), LKR tumors (FIG. 15B) and AE17.ova tumors (FIG. 15C) by 35-50%.

Figures 15A, 15B, 15C, 15D:
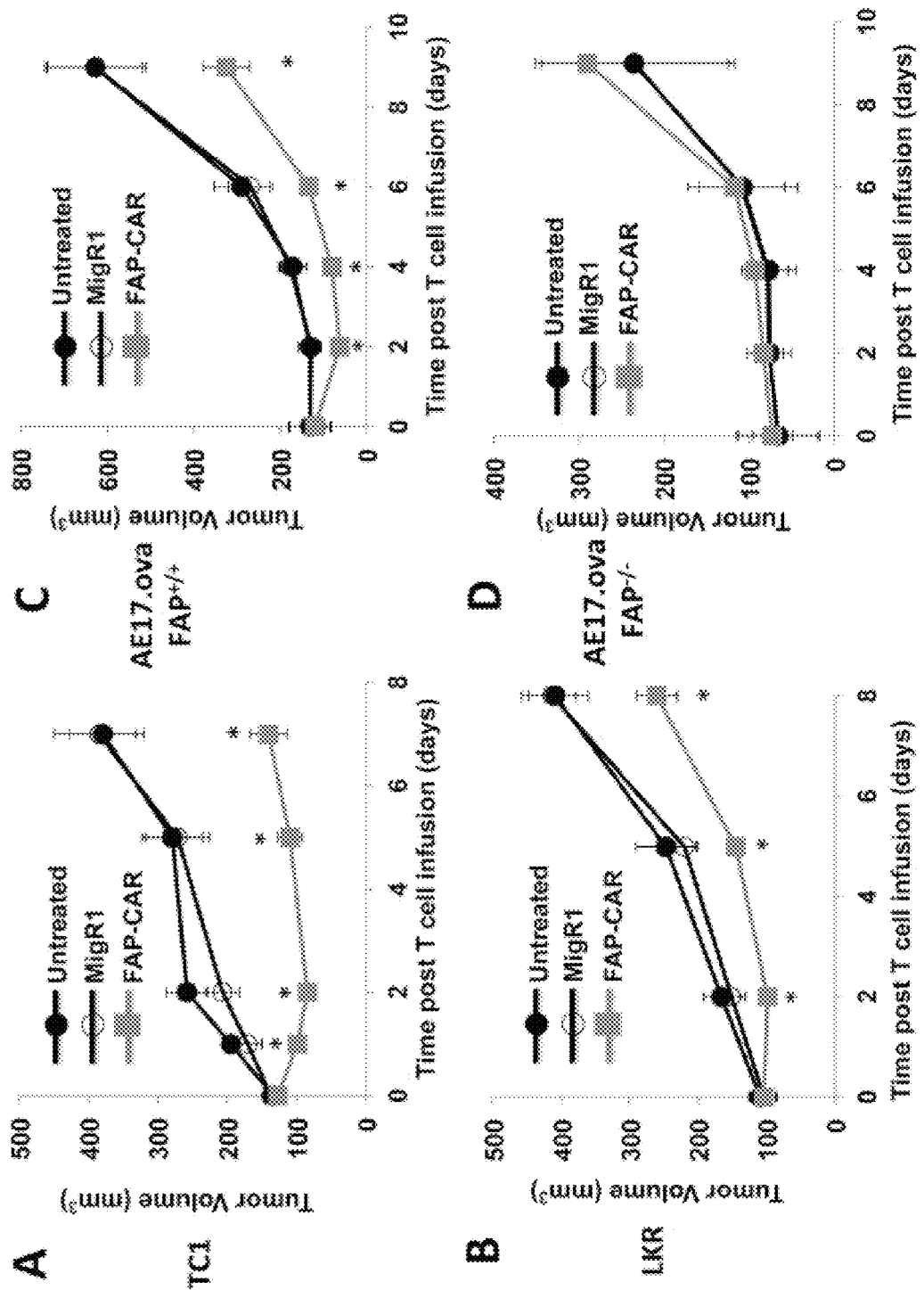
FIG. 15A depicts anti-tumor activities of FAP-CAR T cells in syngeneic mice bearing TC1.
FIG. 15B depicts anti-tumor activities of FAP-CAR T cells in LKR.
FIG. 15C depicts anti-tumor activities of FAP-CAR T cells in AE17.ova tumors injected intravenously with 10 million FAP-CAR or MigR1 T cells when tumor reached approximately 100-150 mm$^3$. Tumor measurements were then followed.
FIG. 15D shows the target-specificity of FAP-CAR T cells, AE17.ova tumor cells were also injected into FAP-null C57BL/6 mice. FAP-CAR T cells were given 7 days later. * Denotes statistical significance between untreated, MigR1 and FAP-CAR-treated samples, p value<0.05.
Figures 16A, 16B:
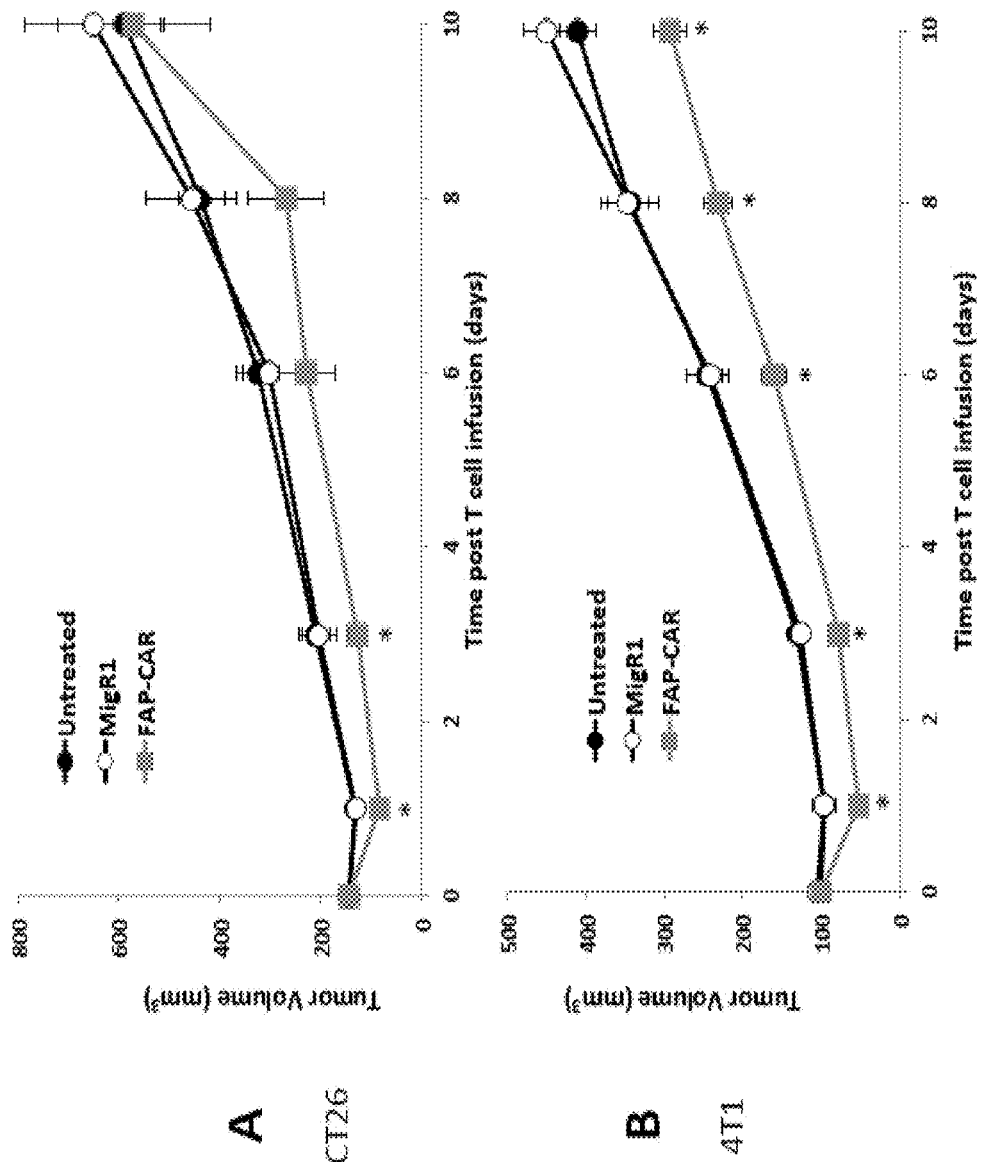
FIG. 16A depicts anti-tumor activity of FAP-CAR T cells in CT26 and 4T1 tumor models. A single dose of FAP-CAR or MigR1 T cells was injected into mice bearing CT26 colon cancer.
FIG. 16B depicts anti-tumor activity of FAP-CAR T cells in mammary cancer, when tumors reached approximately 100-150 mm3. Tumor measurements were then followed. * Denotes statistical significance between untreated, MigR1 and FAP-CAR-treated samples, p value<0.05.

To confirm specificity, AE17.ova cells were inoculated into FAP-null C57BL/6 mice and the tumors were treated as above. In contrast to the effect on AE17.ova tumors in wild-type C57BL/6 mice (FIG. 15C), FAP-CAR T cells had no effect on the growth of AE17.ova tumors in FAP-null mice (FIG. 15D). Given the differences between the efficacy data presented herein and that of Tran et al. (2013, J Exp Med 210:1125-35, two of the same tumor lines, CT26 and 4T1, that they reported were also treated. In contrast to their findings, the FAP-CAR construct of the present invention induced significant reduction in tumor size (FIGS. 16A-16B), although the changes were smaller than those seen in FIGS. 15A-15D.

Effect of the Injection of Mouse FAP-CAR T Cells on FAP+ Cells

To evaluate the effect of the T cells on the FAP+ stromal cells, tumors were harvested 7 to 9 days post-T cell infusion and the dissociated cells were analyzed by flow cytometry. As shown in FIG. 20, at this time point, the FAP+/CD45⁻/CD90+ and FAP+/CD45+ populations were decreased by about 50% in comparison with the untreated group, while the amount of FAP+ cells remaining in MigR1 group was similar to the untreated controls.

Figures 17A, 17B, 17C:
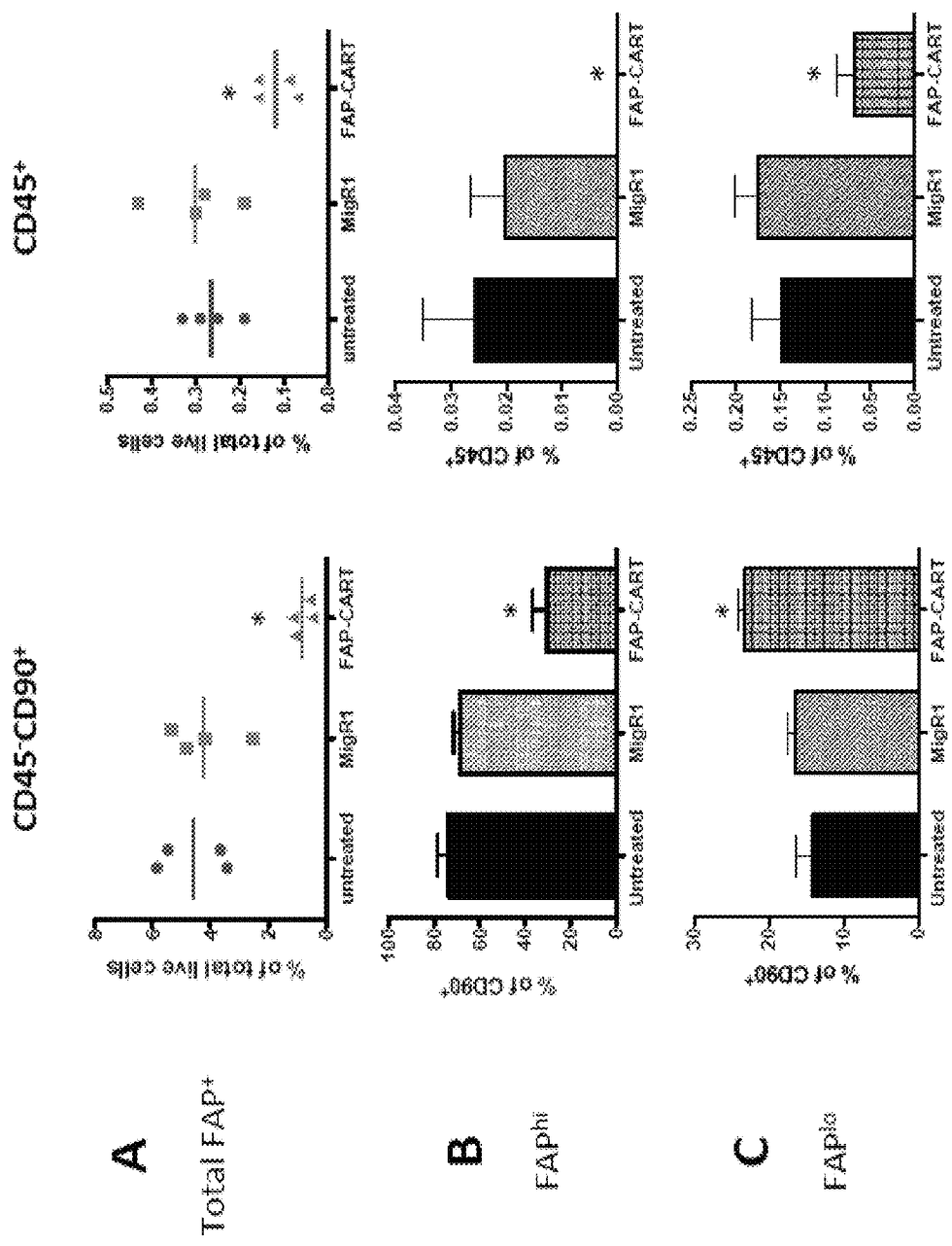
FIG. 17A depicts depletion of FAP+ cells. FAP-CAR T cells were injected intravenously into AE17.ova tumor bearing mice when tumors reached 100 mm3. At 3 days after T cell infusion, tumors were harvested and digested to determine amount of FAP+ cell depletion.
FIG. 17B shows depletion of FAPhi cells by FAP-CAR T cells.
FIG. 17C shows depletion of FAPlo cells by FAP-CAR T cells * Denotes statistical significance between untreated, MigR1 and FAP-CAR-treated samples, p value<0.05.

The AE17.ova model was chosen to characterize this depletion in more detail, and the FAP+ cells were evaluated at 3 days post-T cell transfer. At this earlier time point, larger decreases in FAP+CD90+ stromal cells (82%) and FAP+CD45+ leukocytes (56%) were observed (FIG. 17A). Moreover, both low- and high-FAP expressing cells in both the CD45⁻CD90+ and CD45+ populations could be identified (FIG. 14). When these specific populations were gated on, it was observed that FAP-CAR T cells selectively depleted the FAP-high expressing cells, with little effect on FAP-low expressing cells (FIGS. 17B and 17C).

Kinetics of FAP-CAR T Cell Persistence

The number of intratumoral FAP-CAR T cells in the AE17.ova model was assessed at 3, 7, and 10 days after adoptive transfer. It was discovered that the number peaked at day 3 after injection and diminished at the 7 and 10 day time points by ~65% (FIG. 18A).

Figures 19A, 19B, 19C:
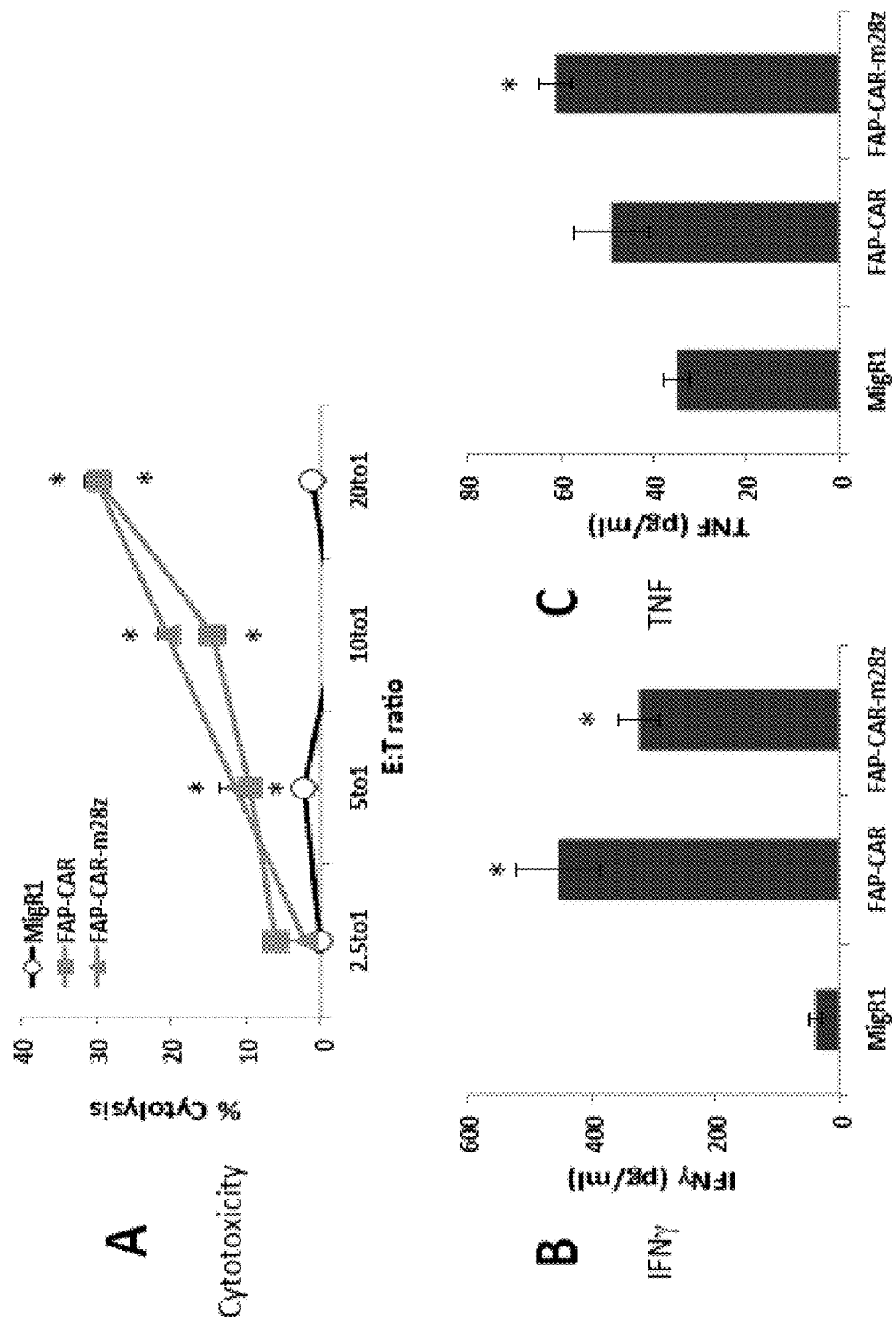
FIG. 19A depicts in vitro activity of T cells expressing fully mouse FAPCAR. To determine target-specific cytolytic activity of two FAP-CAR T cells, various Effector:Target ratio of MigR1 and FAP-CAR T cells were reacted with 3T3.FAP fibroblasts for 18 hours.
FIG. 19B shows IFNγ (FIG. 19B) production from FAP-CAR T cells reacted with 3T3.FAP at effector:target ratio of 10:1 for 18 hours. *Denotes statistical significance between MigR1 versus FAP-CAR-treated groups, p value<0.05.
FIG. 19C shows and TNF production from FAP-CAR T cells.

To determine if this rapid loss of T cells was a consequence of abnormal function of the human CD3Z and 4-1BB cytoplasmic domains within mouse T cells, a second construct was engineered by inserting the scFv anti-FAP 73.3 antibody fragment into a fully murine CAR containing the murine CD3Z chain and the murine CD28 cytoplasmic domain (73.3m28z) (FIG. 11D). In vitro, this construct exhibited similar cytotoxicity and IFN-y release when reacted with FAP-expressing fibroblasts compared to the "human" version of CAR (FIGS. 19A-19C).

Figures 18A, 18B, 18C:
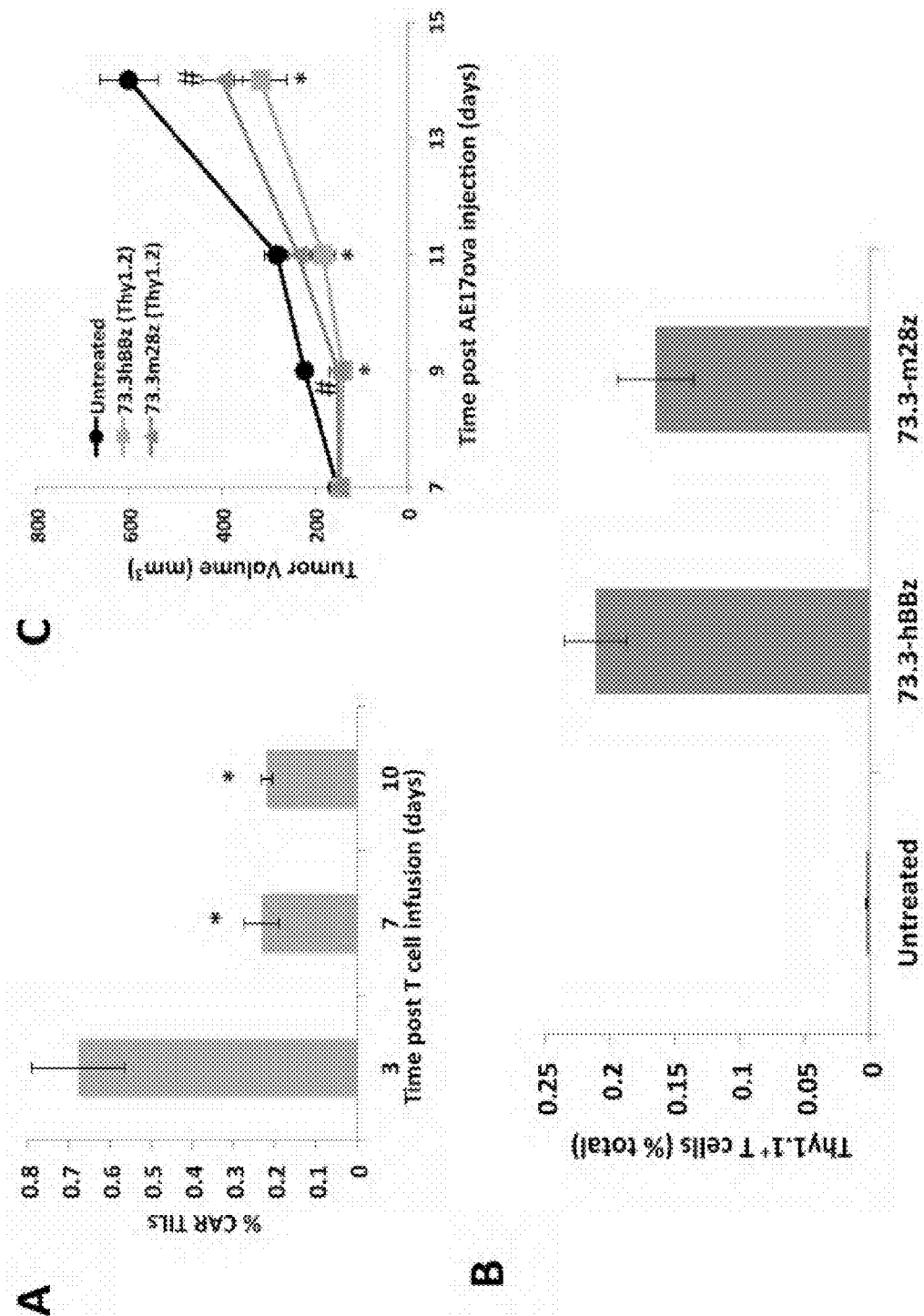
FIG. 18A depicts persistence and anti-tumor activities of two types of FAP-CAR T cells employing either human 4-1BB (73.3-hBBz) or mouse CD28 (73.3-m28z) co-stimulatory domain in mice. Persistence of FAP-CAR T cells (73.3-hBBz) over time. AE17.ova-tumor bearing mice was injected with 10 million FAP-CAR T cells through tail vein when tumor size reached approximately 100 mm$^3$. Tumors were harvested 3, 7 and 10 days after adoptive transfer, to look for GFP+CD3+ FAP-CAR T cells (n=5). * Denotes statistical significance in lower percent CAR TILs compared to the 3 day time point, p value<0.05.
FIG. 18B shows FAP-CAR T cells with different co-stimulatory domain persisted similarly in vivo. Two FAP-CAR constructs, FAP-CAR-hBBz and FAP-CAR-m28z, were transduced into congnic Thy1.1 C57BL/6 mouse T cells to determine their trafficking and persistence in tumor-bearing mice. AE17.ova tumors were injected into regular Thy1.2 C57BL/6 mice. When tumors reached approximately 100-125 mm$^3$, a single dose (10 million) of Thy1.1+ FAP-CAR T cells were then adoptively transferred through tail vein into mice. Tumors were harvested 3 days after adoptive transfer of FAP-CAR T cells in mice. Tumors and pancreas were digested and made into single cell suspension. Cells were then stained with fluorochrome-conjugated anti-Thy1.1, together with anti-CD3 antibody to determine percent FAP-CAR T cells in tumors and pancreas.
FIG. 18C shows in vivo anti-tumor activity of two FAP-CAR T cells. AE17.ova-tumor bearing mice was injected with 10 million FAP-CAR T cells through tail vein when tumor size reached approximately 150 mm$^3$. Tumor measurements were then followed. * Denotes statistical significance between untreated and FAP-CAR-treated samples, p value<0.05.

After injection into mice bearing AE17.ova tumors, the trafficking and persistence of the two types of FAP-CAR T cells were observed to be similar (FIG. 18B), as was antitumor efficacy (FIG. 18C). These data show that, compared to human CAR, mouse CAR T cells have a short persistence time, despite the additional human or mouse co-stimulatory cytoplasmic domains.

Approaches to Enhance FAP-CAR T Cell Therapy

Since the T cells persist for only short periods of time in vivo, it was hypothesized that giving a second infusion of FAP-CAR T cells would enhance therapeutic efficacy. AE17.ova tumor cells were injected into flanks of C57BL/6 mice. When tumors reached approximately 100 $mm^3$, a first dose of FAP-CAR T cells was given intravenously. One week later, we randomly divided the FAP-CAR-treated animals were randomly divided into two groups, one treated with an additional dose of MigR1 (Single dose, FIG. 21A) and one treated with a second dose of FAP-CAR T cells (Double dose, FIG. 21A). At two weeks, tumors in the mice given two doses of FAP-CAR T cells were significantly smaller ($p<0.05$) than those in mice given only one dose of FAP-CAR T cells.

Figures 21A, 21B, 21C:
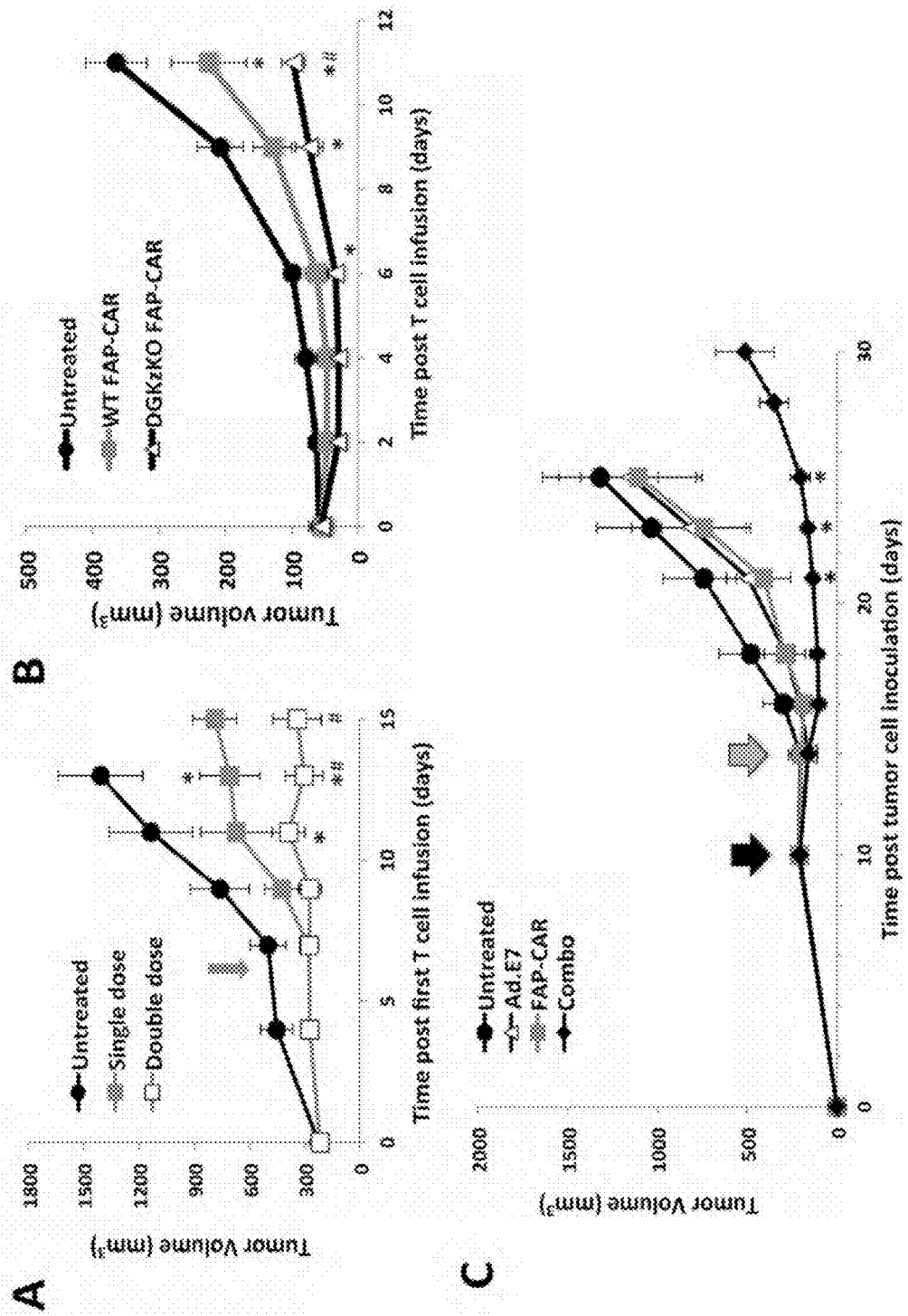
FIG. 21A depicts enhanced therapeutic response of FAP-CAR T cells by giving two doses of FAP-CAR T cells.
FIG. 21B shows the deletion of a negative T cell regulator DGKZ.
FIG. 21C shows the combination of another immunotherapy. Mice with AE17.ova flank tumors were injected intravenously with FAP-CAR T cells when tumors were approximately 100 mm$^3$. The overall efficacy of FAP-CAR T cells was enhanced when a second dose of FAP-CAR T cells was given a week after the first dose. Grey arrow indicates the injection time of the second dose of FAP-CAR T cells. Alternatively, efficacy of FAP-CAR T cells could be enhanced when a negative intracellular regulator DGKZ was deleted in those T cells. * Denotes statistical significance between untreated and FAP-CAR-treated samples, p value<0.05. # Denotes statistical significance between single dose FAP-CAR treated group versus double dose group or DGKZ KO FAP-CAR treated group.
Figures 22A, 22B:
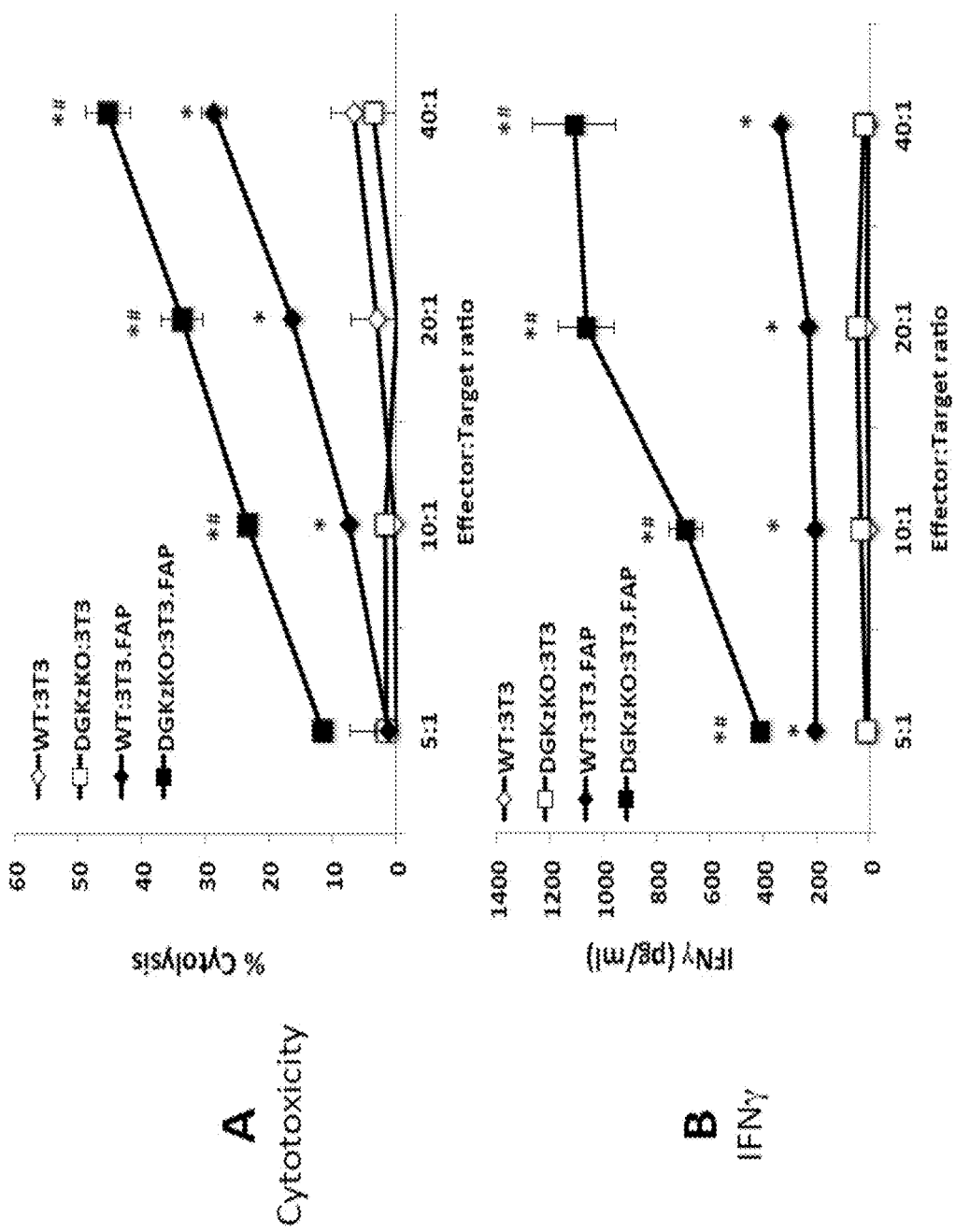
FIG. 22A depicts deletion of DGKζ enhanced cytotoxicity of FAPCAR T cells. Splenic T cells were isolated from intact C57BL/6 mice, as well as DGKζ knockout mice. Isolated T cells were then activated, transduced with FAP-CAR and expanded. A week later, FAP-CAR T cells with or without DGKζ deletion were reacted with 3T3 or 3T3.FAP fibroblasts for 18 hours to determine cytotoxicity. * Denotes statistical significance between untreated and two FAP-CARtreated samples, p value<0.05. # Denotes statistical significance between WT and DGKζ KO FAP-CAR-treated samples, p value<0.05.
FIG. 22B depicts deletion of DGKζ enhanced IFNγ production of FAPCAR T cells. Splenic T cells were isolated from intact C57BL/6 mice, as well as DGKζ knockout mice. Isolated T cells were then activated, transduced with FAP-CAR and expanded. A week later, FAP-CAR T cells with or without DGKζ deletion were reacted with 3T3 or 3T3.FAP fibroblasts for 18 hours to determine IFNγ production. * Denotes statistical significance between untreated and two FAP-CARtreated samples, p value<0.05. # Denotes statistical significance between WT and DGKζ KO FAP-CAR-treated samples, p value<0.05.
Figure 23:
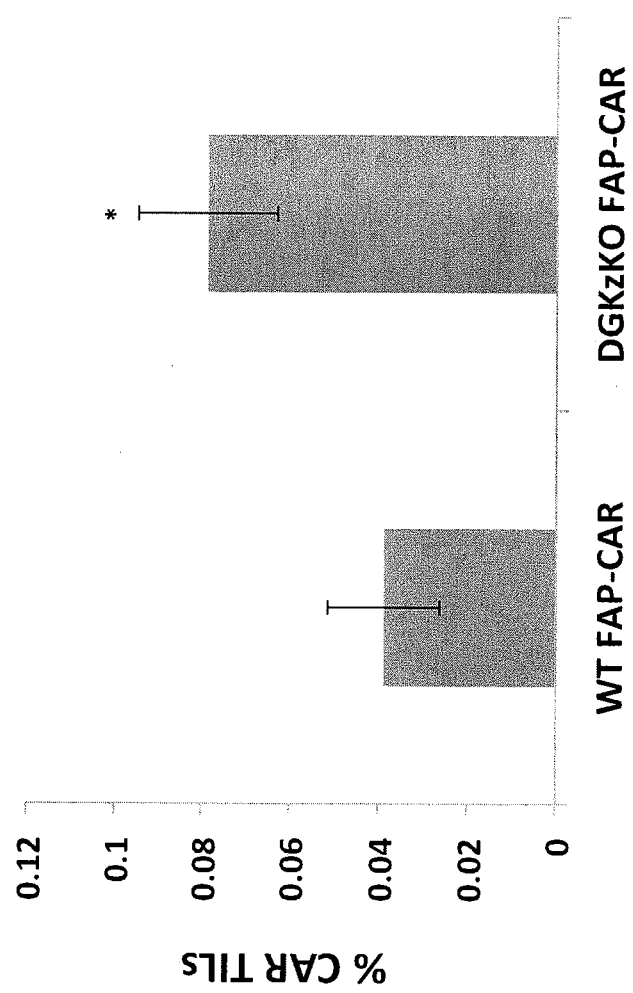
FIG. 23 depicts that DGKζ knockout FAP-T cells persisted longer than wildtype FAP-CAR T cells. AE17.ova tumor mice were adoptively transferred with 10 million wild-type or DGKζ knockout FAP-CAR T cells when tumors reached 100 mm3. Tumors were harvested 11 days post-injection to determine persistence of T cells. Percent FAP-CAR T cells were determined using flow cytometry. * Denotes statistical significance between WT and DGKζ KO FAP-CAR-treated samples, p value<0.05.

The efficacy of comparably transduced FAP-CAR splenic T cells isolated from WT C57BL/6 versus DGKˆ-null mice was compared. DGKZ knockout FAP-CAR T cells were more efficient in lysing 3T3.FAP cells (FIG. 22A) and in secreting IFNy (FIG. 22B) with retention of specificity in vitro. The DGKˆ-deficient FAP-CAR T cells were also more efficient ($p<0.05$ on day 11) after being injected into AE17.ova bearing mice (FIG. 21B). The increased efficacy was associated with greater persistence of the DGKˆ-knockout compared to WT FAP-CAR T cells (GFP+ cells) (FIG. 23). Thus, the enhanced anti-tumor efficacy was likely due to both increased T cell activity and to increased persistence.

Role of the Acquired Immune System in the Efficacy of FAP-CAR T Cells

Figures 24A, 24B, 24C, 24D, 24E, 24F:
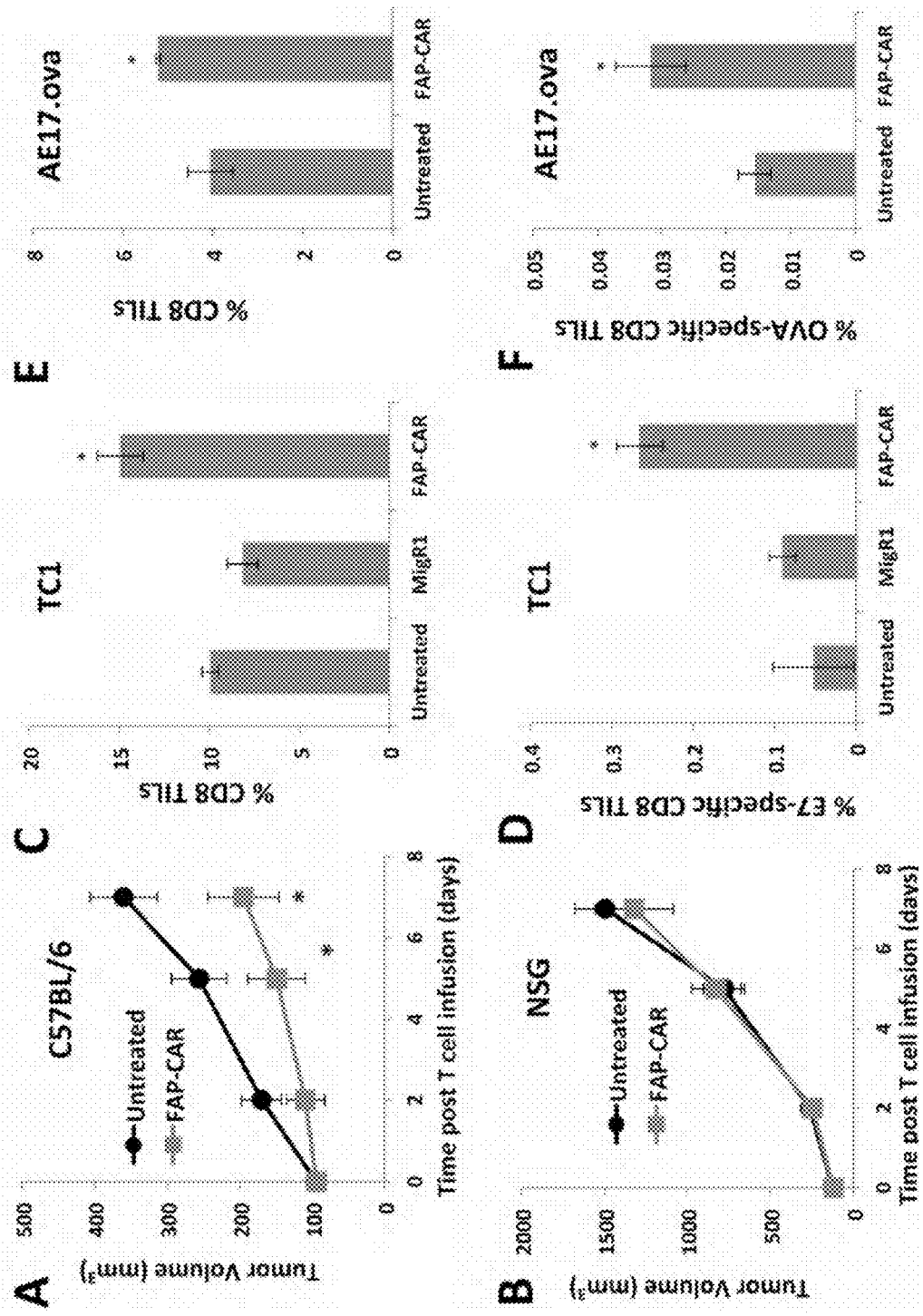
FIG. 24A depicts adaptive immune response plays a key role in FAP-CAR T cells-induced antitumor response. AE17.ova tumors were injected into both C57BL/6.
FIG. 24B shows AE17.ova tumors injected into NSG mice. When tumors reached approximately 100-125 mm$^3$, a single dose (10 million) of FAP-CAR T cells were then adoptively transferred through tail vein into mice. Tumor measurements were then followed. * Denotes statistical significance between untreated and FAP-CAR-treated samples, p value<0.05. FAP-CAR induced infiltration of antigen-specific CD8 T cells into tumors.
FIG. 24C shows TC1 tumors harvested 8 days after adoptive transfer of FAP-CAR T cells in mice.
FIG. 24D shows AE17.ova tumors were harvested 8 days after adoptive transfer of FAP-CAR T cells in mice. Tumors were digested and made into single cell suspension. Cells were then stained with fluorochrome-conjugated tetramer loaded with E7- or SIINFEKEL(ova)-peptide, together with anti-CD8 antibody to determine percent tumor-specific CD8 T cells in tumors. * Denotes statistical significance between untreated, FAP-CAR-treated samples, p value<0.05. significance between WT and DGKζ KO FAP-CAR-treated samples, p value<0.05.
FIG. 24E shows TC1 tumors harvested 8 days after adoptive transfer of MigR1 T cells in mice.
FIG. 24F shows AE17.ova tumors were harvested 8 days after adoptive transfer of FAP-CAR T cells in mice. Tumors were digested and made into single cell suspension. Cells were then stained with fluorochrome-conjugated tetramer loaded with E7- or SIINFEKEL(ova)-peptide, together with anti-CD8 antibody to determine percent tumor-specific CD8 T cells in tumors. * Denotes statistical significance between untreated, MigR1-treated samples, p value<0.05. significance between WT and DGKζ KO FAP-CAR-treated samples, p value<0.05.

The role of the acquired immune system in the FAP-CAR T cell-mediated anti-tumor response was evaluated by injecting AE17.ova tumors into the flanks of wild-type C57BL/6 mice or in immunodeficient NSG mice and treating with one injection of $10^7$ FAP-CAR T cells. AE17.ova tumors grew more rapidly in NSG than wild-type mice (FIG. 24A vs 24B) reflecting the endogenous anti-tumor activity in wild-type mice that was lost in the NSG mice. In contrast to the efficacy of the mouse FAP-CAR T cells in wild-type mice (FIG. 24A), the mouse FAP-CAR T cells had no anti-tumor effects on the AE17.ova tumors in the immunodeficient NSG mice, (FIG. 24B). This loss in activity was not due to loss of FAP expression in the NSG tumor microenvironment, as we confirmed that AE17.ova tumor in NSG mice develop a similar level of FAP expression as in immune-competent C57BL/6 mice.

To further explore this issue, taking advantage of the fact that TC1 tumor cells express the viral oncogenic protein HPV-E7 and that AE17.ova cells express chicken ovalbumin, the impact of $FAP^+$ cell depletion on endogenous anti-tumor immunity using E7- or ova-specific tetramer staining of the infiltrating lymphocytes 8 days after adoptive transfer was evaluated. A significantly (p=0.02) increased percentage of total $CD8^+$ T cells within the tumors of FAP-CAR-treated mice compared to control or MigR1-T cell-treated mice was observed (FIGS. 24C and 24E). In addition, tumors from FAP-CAR-treated mice had significantly (p=0.015) increased numbers of E7-specific T cells (FIG. 24D) or ova-specific T cells within the TC-1 and AE17.ova tumors respectively (FIG. 24F).

Figures 25A, 25B:
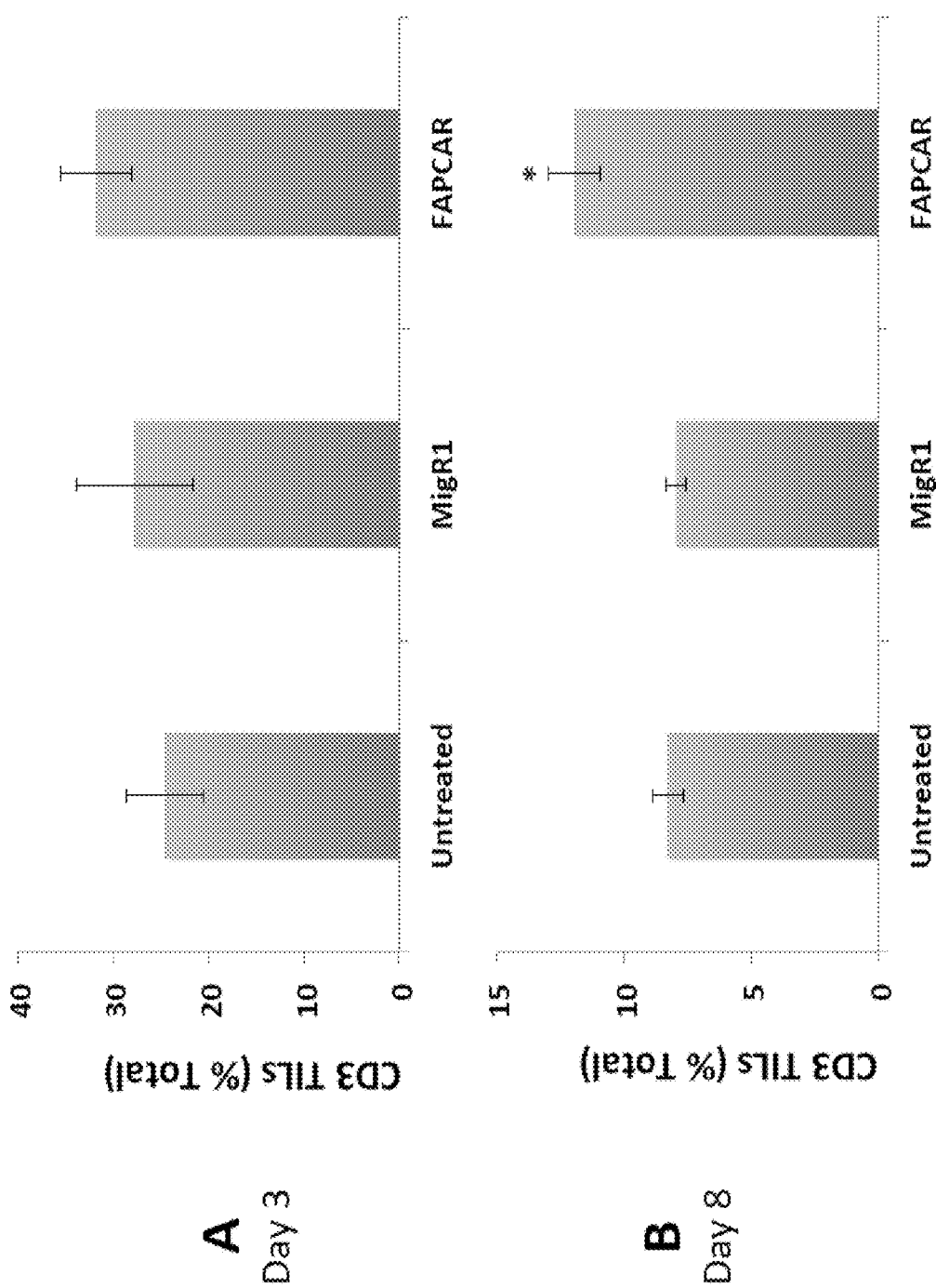
FIG. 25A depicts infiltration of endogenous TILs following treatment of FAP-CAR T cells. AE17.ova tumor bearing mice were given FAP-CAR or MigR1 T cells when tumors reached approximately 100 mm3. Tumors were harvested 3 days later to determine percent T cells infiltrating AE17.ova tumors following treatment of FAP-CAR T cells.
FIG. 25B depicts infiltration of endogenous TILs following treatment of FAP-CAR T cells harvested 8 days later to determine percent T cells infiltrating AE17.ova tumors following treatment of FAP-CAR T cells. * Denotes statistical significance between untreated, MigR1 and FAP-CAR-treated groups, p value<0.05.
Figures 26A, 26B, 26C, 26D:
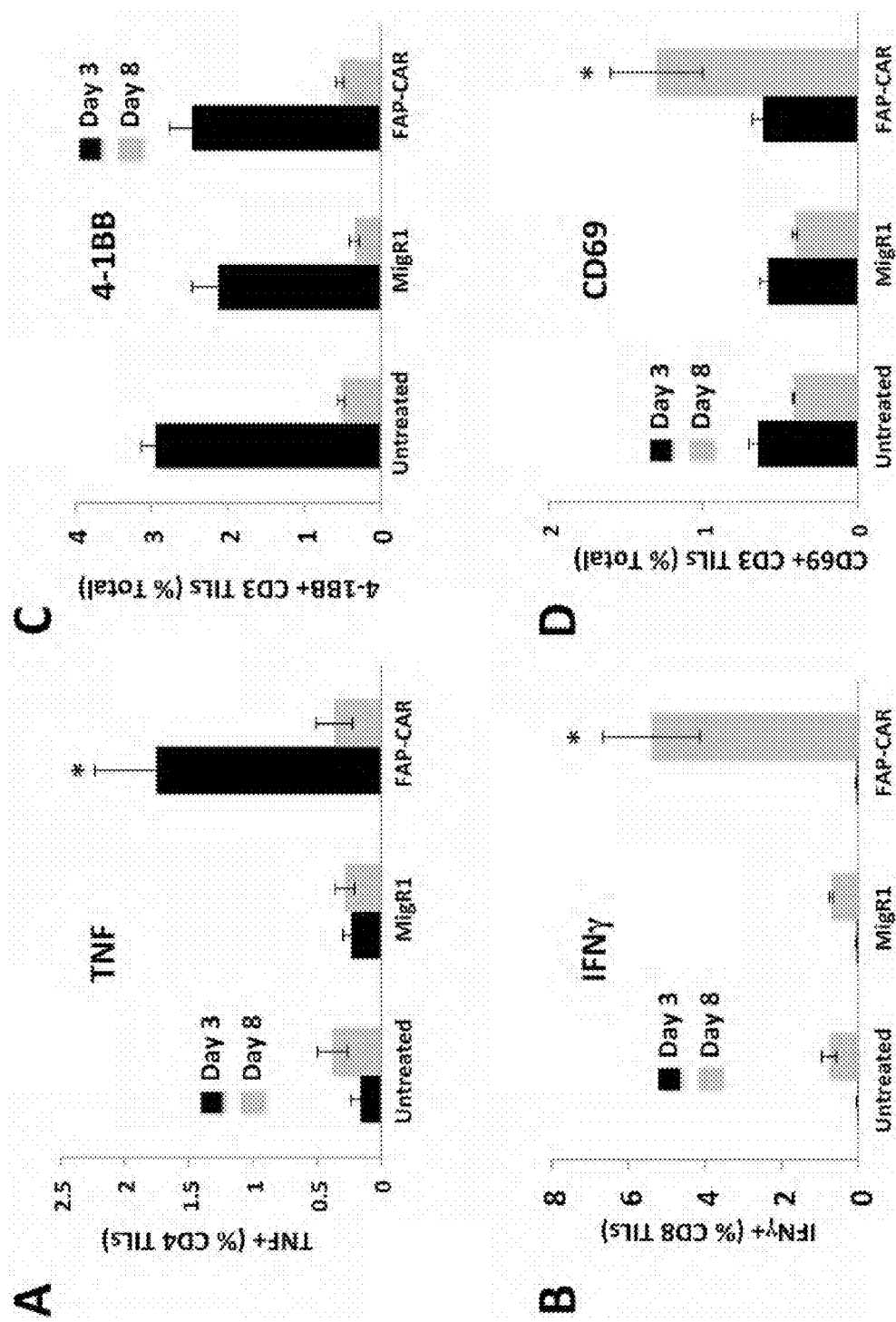
FIG. 26A depicts FAP-CAR T cells activate endogenous T cells. AE17.ova tumors were injected intravenously with 10 million FAP-CAR or MigR1 T cells when tumor reached approximately 100 mm$^3$. At 3 and 8 days following adoptive transfer, tumors were harvested and digested to check for number of TNF producing cells.
FIG. 26B shows IFNγ-producing cells.
FIG. 26C shows the number of 4-1BB+ TILs.
FIG. 26D shows the number of CD69+ TILs. * Denotes statistical significance between untreated, MigR1 and FAP-CAR-treated samples, p value<0.05.
Figures 27A, 27B, 27C, 27D, 27E, 27F:
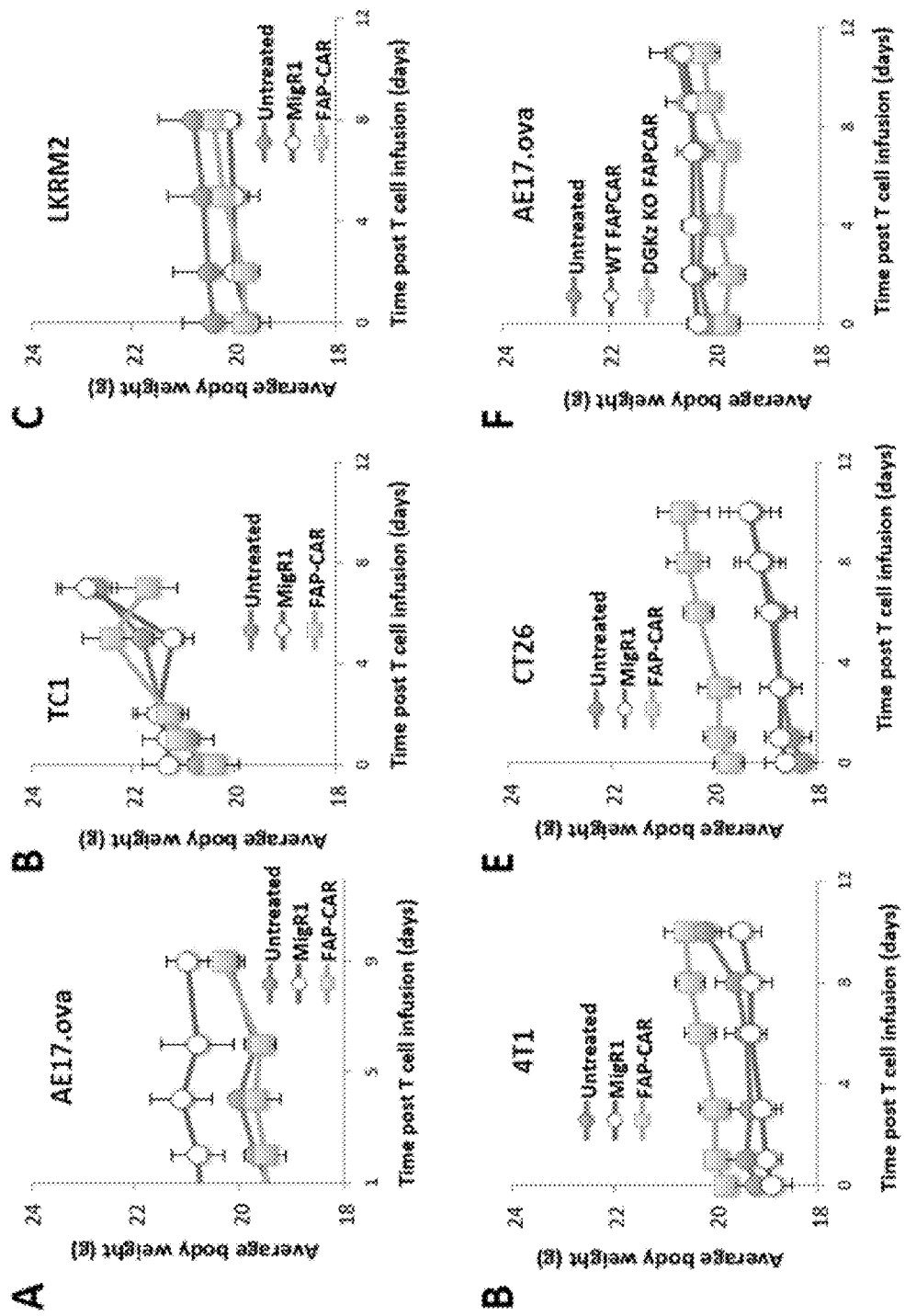
FIGS. 27A-27F show the body weights of FAP-CAR T cell-treated mice remained unchanged or increased. Body weight of tumor bearing mice receiving a single dose of FAP-CAR T cells were monitored over time.

To better understand the mechanisms of this immune response, the above experiment was repeated with AE17.ova tumor-bearing mice, but the endogenous (non-GFP-expressing) T cells were analyzed at 3 and 8 days after T cell injection. Consistent with previous findings by Kraman et al. (2010, Science 330:827-30) who used a genetic approach to ablate FAP+ cells, the number of intratumoral T cells was similar between all three groups at 3 days post adoptive transfer (FIG. 25A). However, at this time point, the number of CD4+ T cells producing TNFa was significantly higher in FAP-CAR T cell group compared to untreated and control T cell groups (FIG. 26A; black bars), while there was no difference in the numbers of CD69+ and 4-1BB+ T cells, nor in IFN-y-producing CD8 T cells (FIGS. 26B-26D; black bars). At 8 days following treatment of FAP-CAR T cells, the number of T cells was higher in tumors treated with FAP-CAR T cells (as above) compared to the two control groups (FIG. 25B). At this time point, however, the number of CD69+ and IFNy+ CD8+ T cells was increased (FIGS. 26B and 26D; gray bars), while TNF producing T cells and 4-1BB+ expressing T cells were similar among the groups (FIGS. 26A and 26C; gray bars). Together, these results establish that depletion of FAP+ cells in tumors enhances enhance anti-tumor immunity by initially activating endogenous T cells, followed by increasing intra-tumor T cell infiltration at a later timepoint.

Augmentation of the Efficacy of FAP-CAR T Cells by Combination with an Anti-Tumor Vaccine Given the effects of FAP+ tumor cell depletion on anti-tumor immunity, it was hypothesized that combining a tumor vaccine with FAP-CAR T cell administration would enhance anti-tumor efficacy compared to either approach alone. The HPV-E7-expressing TC1 tumor cells were injected subcutaneously into C57BL/6 mice, when tumors reached approximately 200 mm³ saline or one subcutaneous dose of a vaccine consisting of $10^9$ pfu of an adenovirus expressing HPV-E7 (Ad.E7) (black arrow) was administered to boost the endogenous T cell response against E7-expressing cells. Four days after saline injection or vaccination, FAP-CAR T cells ($10^7$ cells; gray arrow) were given intravenously. Both the Ad.E7 cancer vaccine and the FAP-CAR T cells, had only modest effects on these large established tumors by themselves (FIG. 21C). However, the combination was able to induce tumor regression and inhibit tumor growth up to two weeks before tumors started progressing.

Toxicity

Since FAP is an endogenous protein and toxicity (especially weight loss and anemia) was recently reported after depletion of FAP+ cells either by genetic ablation or FAP-CAR T cell administration, possible off-tumor/on-target adverse effects after administration of our FAP-CAR T cells were assessed. No clinical toxicity or anemia in any of the FAP-CAR T cell studies described herein was observed. The body weight of tumor-bearing mice remained the same or increased throughout each experiment (FIGS. 27A-27F).

To further evaluate toxicity, necropsies were performed and visceral organs (heart, lungs, pancreas, liver, spleen, kidneys, skeletal muscle, and bone marrow) were harvested, sectioned, stained and analyzed in a blinded fashion eight days after T cell injection in mice treated with one dose of WT FAP-CAR T cells and eight days after a second dose of WT-FAP CAR T cells from the mice from the experiment shown in FIG. 21A. When compared to control tumor-bearing mice, no abnormalities were observed in the mice given WT FAP-CAR T cells. This specifically included lack of bone marrow hypoplasia (FIGS. 28A-28C) or any change in skeletal muscle.

Necropsies on the mice 8 days after injection of the hyperactive DGK^-deficient FAP-CAR T cells from the experiment depicted in FIG. 21B. No abnormalities were noted, except in the pancreatic sections that exhibited some mild focal peri-vascular and peri-islet lymphocytic infiltration (FIG. 29C). These changes were not seen in mice injected with wild-type FAP-CAR T cells (FIG. 29B).

The anti-tumor efficacy and safety of chimeric antigen receptor-transduced T cells targeted to cells expressing FAP, a target that is highly up regulated in tumor stroma has been investigated herein. Given that cancer-associated stromal cells appear to have a major immune modulating effect on both innate and acquired immunity, it was important to use fully immune-competent mice, without ablation of bone marrow cells, so that the role of the acquired immune system in FAP-CAR T cell-mediated anti-tumor response could be evaluated.

The data presented herein establish that mouse FAP-CAR T cells exhibit antigen-specific cytotoxicity against FAP+ stromal cells and markedly reduce the rare subset of FAP+/CD45+/F4/80+ myeloid cells and the more prevalent FAP+/CD90+ stromal cells detected in multiple mouse models of established mesothelioma and lung cancer (FIG. 20). A single treatment with FAP-CAR T cells resulted in ~80% depletion of the $FAP^{hi}$ stromal cells at 3 days following treatment of FAP-CAR T cells (FIG. 17A), leaving white blood cells and $FAP^{lo}$ cells relatively unaffected (FIGS. 17B and 17C). The depletion of FAP+ cells was associated with a significant inhibition (35-50%) of tumor growth compared to untreated and vector control-transduced CAR T cell (MigR1) treated tumors (FIG. 15A-15C, FIGS. 16A-16B). Importantly, the anti-tumor activity of FAP-CAR T cells was lost in FAP-null mice (FIG. 15D) indicating that the anti-tumor activity of FAP-CAR T cells is dependent on expression of FAP on host-derived cells.

It has also been discovered in the present invention that the anti-tumor efficacy of FAP-CAR T cells was lost in immunodeficient mice (FIG. 24B) emphasizing the importance of the acquired immune system at least in the tumor models employed in this study. To more completely understand this effect, the endogenous T cells within the tumors were evaluated at 3 and 8 days after CAR-T cell infusion. At the earlier time-point, no increase in T cell infiltration or CD8 T cell activation was observed. However, an increase in the number of CD4+ T cells producing TNF-α was evident (FIG. 26A). At the later time-point, an increase in infiltration of total CD8+ T cells within the tumors was observed, as well as antigen-specific CD8+ T cells in both the AE17.ova and E7-positive TC1 tumors. More IFNγ producing CD8+ T cells and more CD69+ T cells were also found at this time (FIGS. 26B and 26D). These data suggest that FAP-CAR T cells enter the tumors and deplete FAP+ cells, which through an unknown mechanism activates endogenous CD4+ T cells to produce TNF. The high levels of TNF may induce tumor cell apoptosis, as well as induce a temporary tumor vasculature shut down which may limit early infiltration by endogenous T cells. It appears that by 8 days after FAP-CAR T cell treatment, activated CD8+ cells enter the tumor and function to further limit tumor growth. However, it should be noted that in mouse tumors, which are relatively immunogenic tumors and have relatively few fibroblasts, the contribution of the immune-mediated mechanisms may be relatively prominent compared to the potential contribution of non-immune mediated mechanisms (i.e. alterations in matrix and/or angiogenesis) that might be seen in non-immunogenic, more fibroblast-rich tumors. Preliminary studies using more desmoplastic, non-immunogenic mouse tumor models and human xenografts support this idea.

Figures 30A, 30B:
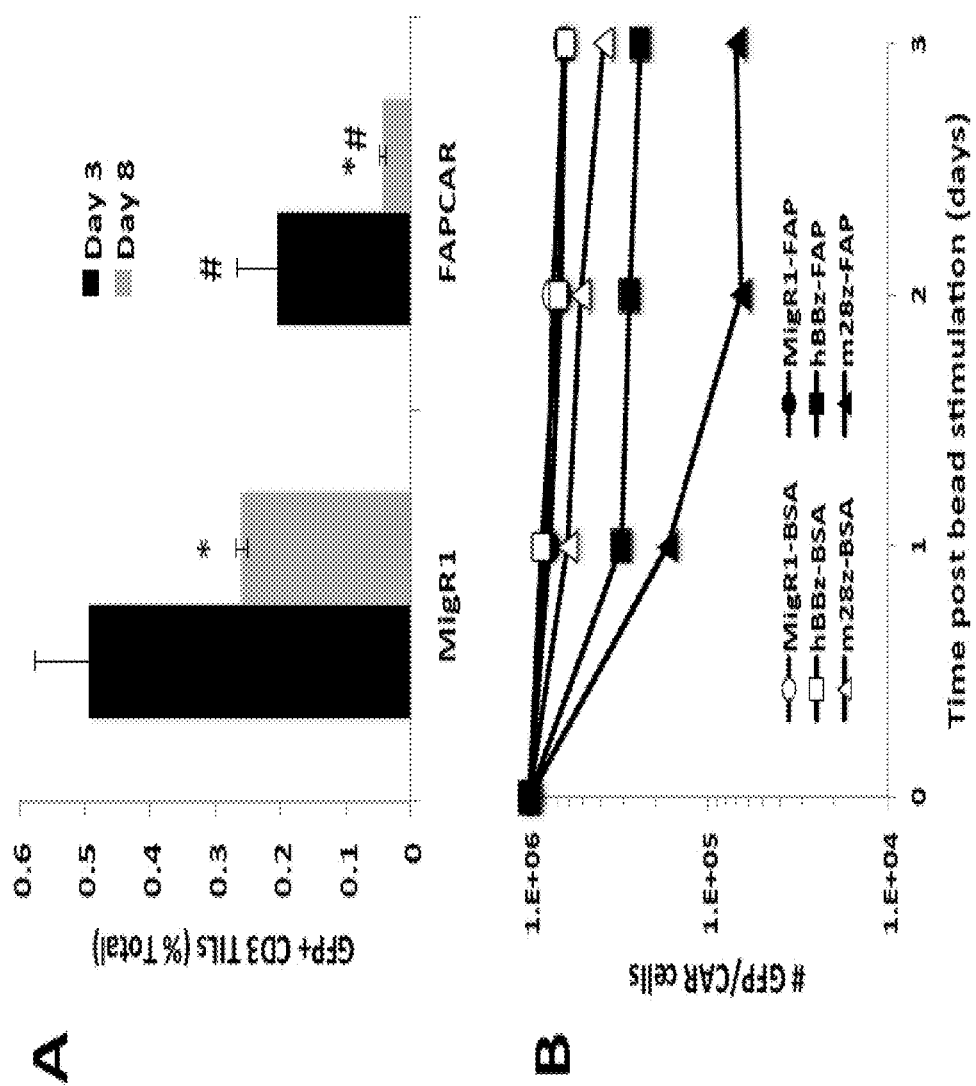
FIG. 30A depicts activation-induced cell death of FAP-CAR T cells. Comparison of in vivo persistence between MigR1 and FAP-CAR T cells. Tumors were harvested 3 and 8 days following adoptive transfer of 10 million FAP-CAR T cells in AE17.ova tumor bearing mice. * Denotes statistical significance in lower percent TILs compared to the 3 day time point, p value<0.05. # Denotes statistical significance in lower percent FAP-CAR TILs compared to MigR1 TILs at the same time point, p value<0.05.
FIG. 30B shows that the FAP-CAR T cells died soon after antigen stimulation. MigR1 and FAP-CAR T cells with either human or mouse intracellular domains were exposed to either BSA- or FAP-coated beads. Amount of live cells were counted every day for 3 days, by trypan blue staining.
Figures 31A, 31B, 31C, 31D:
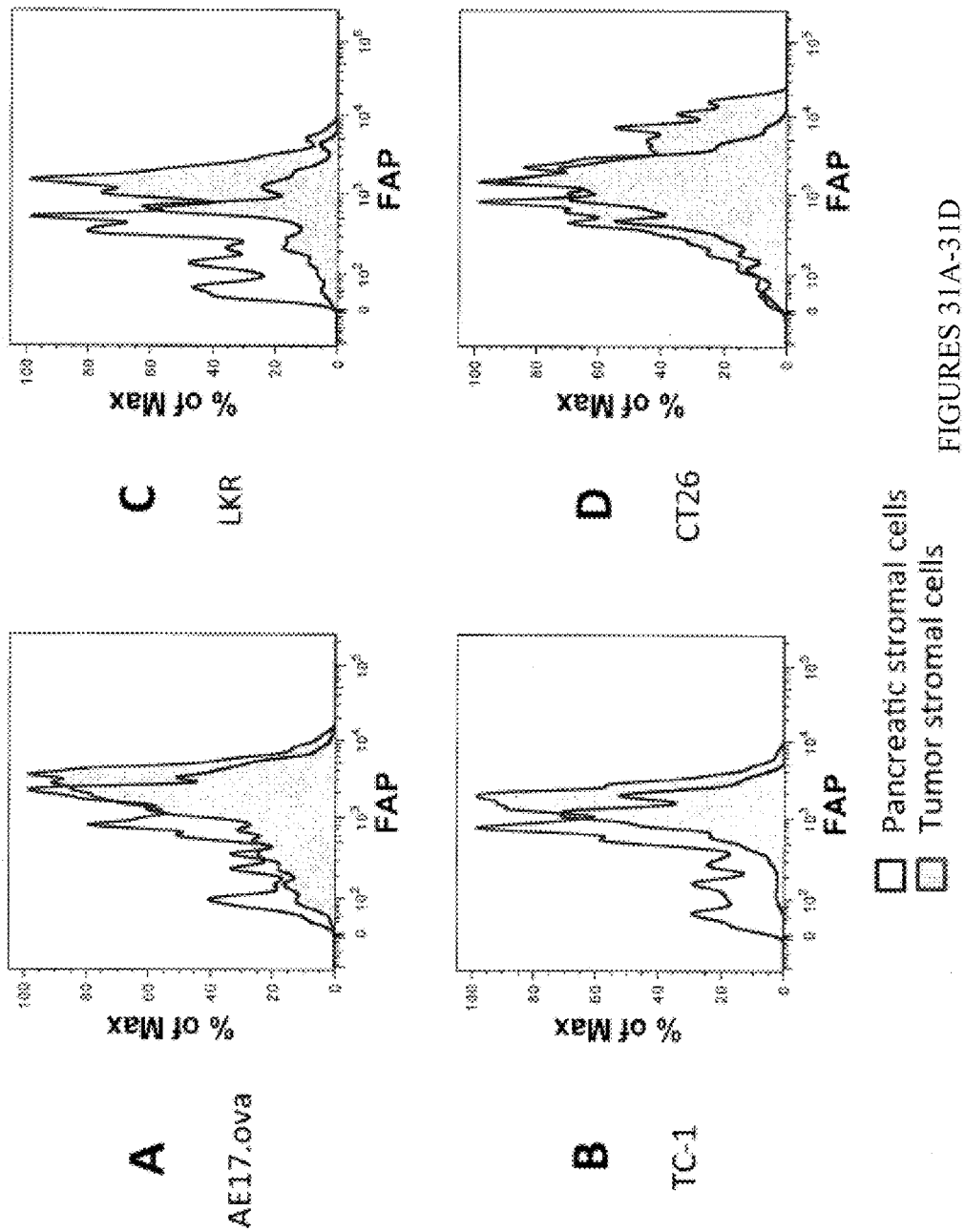
FIGS. 31A-31D depict differential FAP expression on tumor and pancreatic FAP+ stromal cells. Tumors and pancreas from different tumor bearing mice were harvested and digested to form single cell suspension. Cells were then stained with biotin-conjugated anti-FAP antibody and streptavidin-conjugated fluorochrome, together with anti-CD90 and anti-CD45 antibodies. The mean fluorescence intensity of FAP expression on CD90+CD45-cells in tumors and pancreas were compared.

In the models presented herein, the use of FAP-CAR T cells led to a significant, but only temporary inhibition of tumor growth. One reason for the transience of the effect is likely the relatively short persistence of the murine CAR T cells; the number of intra-tumoral murine FAP-CAR T cells rapidly decreased with time (FIG. 18A). This is likely due to a number of well-known intrinsic differences between mouse and human T cells. After expanding human CAR T cells, the lymphocytes can be "rested down" before injection and are less sensitive to immediate activation-induced cell death (AICD). In the mouse system, the cells are highly activated (needed for retroviral transduction) when injected. Whereas the human T cells persist and proliferate in tumors for weeks, many of the transduced mouse T cells undergo AICD (FIGS. 30A-30B) and have a relatively short lifespan compared to human cells. To ensure this short lifespan was not due to the fact that the construct used herein incorporated human CD3Z and human 4-1BB activation domains, a fully mouse FAP-CAR construct was made that had the 73.3 scFv coupled with the mouse CD3Z chain and mouse CD28 domain (FIG. 11D). Virtually equal efficacy in killing, cytokine production, persistence, as well as anti-tumor activity between T cells expressing the two constructs was observed (FIGS. 19A-19C, FIG. 18D). In addition, both types of CARs were equally susceptible to ACID (FIG. 30B). FAP-CAR mouse T cells were examined to see if they would be enhanced if they were "preconditioned" in the host by inducing lymphodepletion or IL-2 administration, but no increase in efficacy in mice irradiated prior to injection of our FAP-CAR T cells was observed.

Given the lack of persistence of the FAP-CAR T cells (FIG. 18A), it was not surprising that efficacy could be enhanced by giving a second dose of T cells one week after the first (FIG. 21A), clearly demonstrating that enhanced persistence could augment efficacy. Also, by blocking a T cell-intrinsic negative regulatory mechanism (up-regulation of the enzyme DGK), the killing ability and persistence of murine CAR T cells could be augmented. In addition, FAP-CAR T cells deficient in DGKZ showed enhanced ability to kill FAP expressing cells in vitro and were clearly more efficacious in vivo (FIG. 21B). These data thus suggest that it will be advantageous to optimize both the persistence and potency of the T cells.

Despite using different mouse strains in each mouse tumor model, less than 0.1% of FAP+ stromal cells in the lungs and bone marrows were observed. In contrast, 3-5% of dissociated cells from the pancreas expressed FAP. However, when FAP expression on those pancreatic stromal cells was compared with the tumor-associated stromal cells isolated from the same hosts, cancer associated stromal cells expressed higher levels of FAP (FIGS. 31A-31D).

Figures 28A, 28B, 28C:
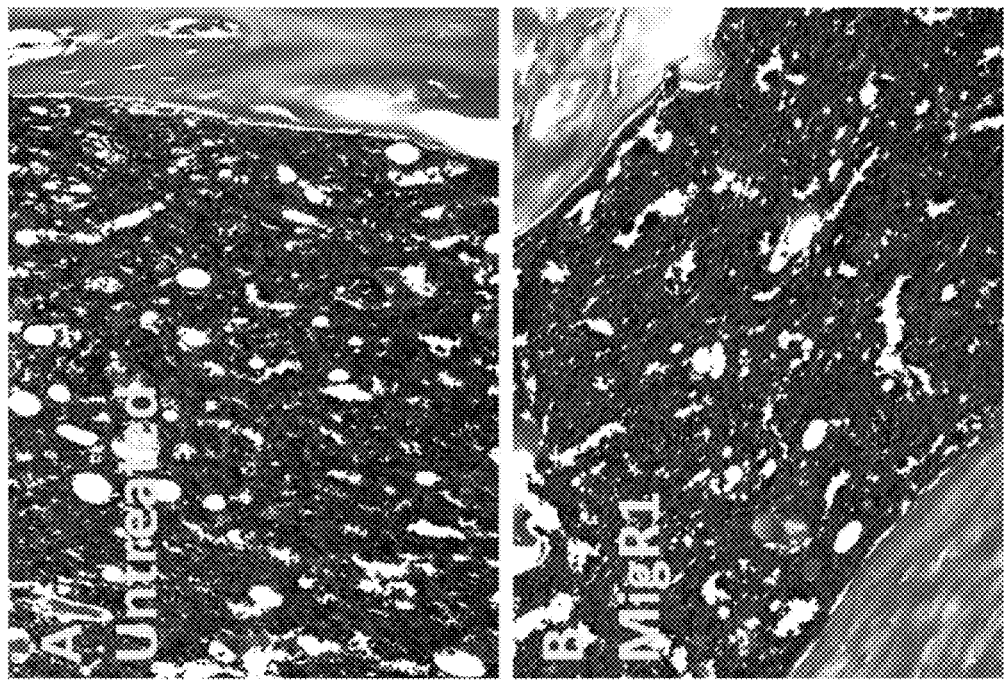
FIG. 28A depicts that bone marrows showed normal histology following treatment with FAP-CAR T cells. Representative H&E sections of femur bones are shown from control untreated tumor-bearing mice.
FIG. 28B shows representative H&E sections of femur bones from tumor-bearing mice treated with MigR1 T cells.
FIG. 28C shows representative H&E sections of femur bones from tumor-bearing mice treated with FAP-CAR T cells. Femurs were harvested one week after T cell infusion.

Administration of one dose or even two doses of the FAP-CAR T cells did not cause any weight loss (FIGS. 27A-27F), nor did they cause any decrease in hematocrit or increase in serum amylase. Furthermore, detailed histologic analyses of necropsy samples showed no microscopic abnormalities, and specifically no damage to muscle, pancreas (FIGS. 29A-29C), or bone marrow (FIGS. 28A-28C).

Thus, the data establish that it is possible to partially deplete tumor-associated FAP+ cells while retaining anti-tumor efficacy, but without eliciting severe side effects. This may be related to the fact that our FAP-CAR T cells were able to efficiently eliminate the FAP while sparing the cells expressing lower levels of FAP (FIGS. 17A-17C), like those in the pancreas, and presumably like those in the bone marrow and muscle. The only instance in which any histologic abnormalitites were observed was in the pancreas (FIG. 29C), but only when hyperactive DGKˆ-deleted cells were used.

Anti-tumor activity with CARs containing either human and mouse cytoplasmic domains was observed (FIG. 18C). The data suggest that endogenous immune effects may be important for the efficacy of the CARs.

The data also establish that FAP-CAR T cells may be used in combination with other therapies. This can include combination with chemotherapy where stromal disruption could enhance drug delivery and combinations with immunotherapy. In the present invention, FAP-CAR T cells were combined with an Ad.E7 cancer vaccine which generates E7-specific adaptive immune response against TC1 cells. As expected, neither the cancer vaccine nor FAP-CAR T cells worked well on large, established tumors (FIG. 21C). However, in combination, there was an additive, and perhaps synergistic effect against TC1 tumors.

In summary, the data establish that FAP-CAR T cells recognize target cells in an antigen-specific manner and reduce tumor growth in vivo. Targeting tumor stromal cells with CAR T cells augmented anti-tumor immunity. It is likely that he efficacy of FAP-CAR T cells can be enhanced by improving persistence of T cells, producing more highly active T cells, administering multiple doses of FAP-CAR-T cells, and by combining with other types of immunotherapy or chemotherapy. Toxicity was not observed, at least under dosing conditions tested herein in otherwise healthy tumor-bearing animals.

Additional Data

Figure 32:
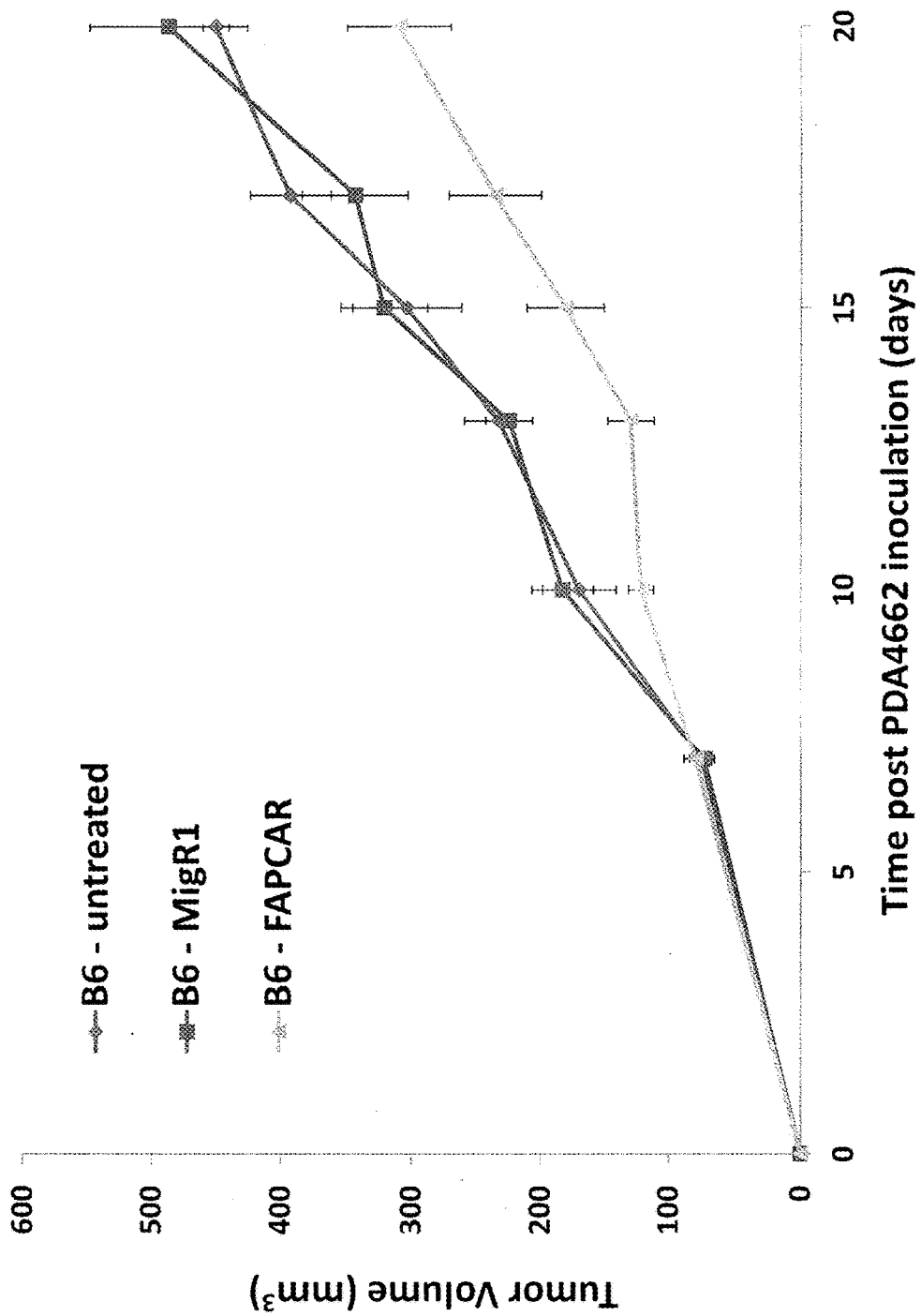
FIG. 32 is a graph depicting in vivo efficacy of FAP-CAR T cells in mouse pancreatic cancer model.

FAP-CAR T Cells are Efficacious in A Mouse Pancreatic Cancer Model and in an Autochthonous Mouse Lung Cancer Model The efficacy of the FAP-CAR T cells in a pancreatic cancer model called PDA4662 was tested. In comparison to other flank tumor models, this particular tumor model shows more desmoplastic characteristic, and is non-immunogenic. $10^7$ anti-mouse FAP-CAR T cells or control T cells (MigR1)

were injected into mice when PDA4662 tumors reached 100 mm³ in size. Tumor measurements were then followed. FAP-CAR T cells induced significant inhibition in tumor growth, while the control T cells did not have any effect on tumor growth (FIG. 32).

Figure 33:
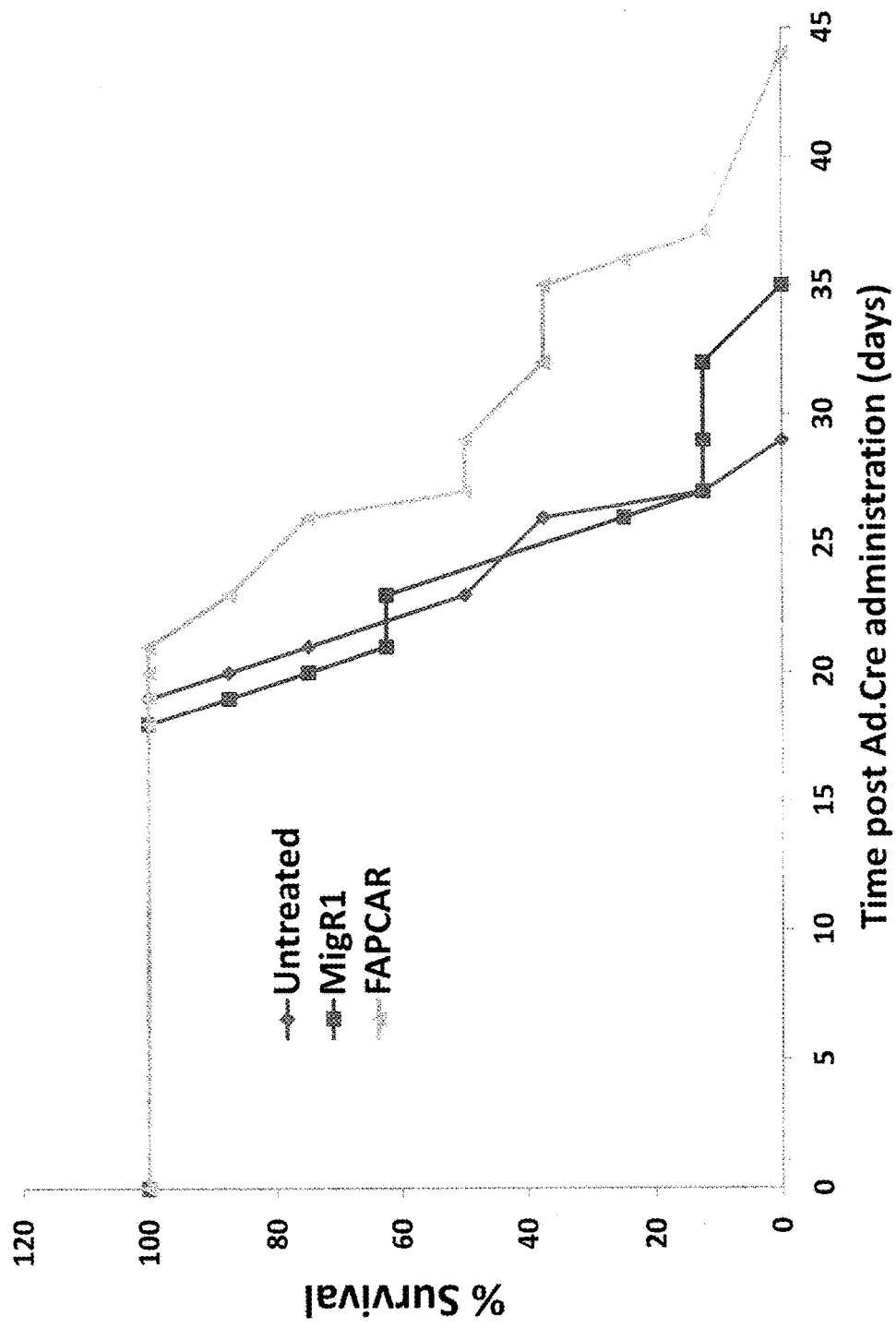
FIG. 33 is a graph depicting in vivo efficacy of FAP-CAR T cells in an autochthonous lung cancer model.

An autochthonous lung cancer mouse model was generated by crossing LSL-KrasG12D mice that carry an inducible constitutively active mutant allele of Kras, with conditional TGFBRIIflox/flox knock-out mice. The oncogenic Kras mutation is relevant to human disease as Kras mutation and/or over expression is the most common oncogenic event associated with human lung cancer. The Kras/TGFBRII KO model, with simultaneous induction of Kras and deletion of TGFβRII, leads to the development of tumors that more closely resemble primary human lung cancer with regard to invasion and collagen deposition. These animals die with large invasive lung tumors (and mediastinal metastases) within 4 weeks. Briefly, mice that were heterozygous for the LSL mutant KrasG12D gene and homozygous for a floxed TGBβRII gene were anesthetized and given $10^9$ pfu of an adenovirus expressing Cre via the intranasal route to both induce tumors and inactivate the TGF-β receptor in the same epithelial cells. Two weeks after Ad.Cre injection, $10^7$ anti-mouse FAP-CAR murine T cells or control murine T cells (MigR1) were administered intravenously. In total, three weekly doses of T cells were given to the mice. In FIG. 33 the overall survival of those Kras/TGFbRII mice after adoptive transfer of FAP-CAR T cells can be seen. FAP-CAR T cells, but not control T cells, prolonged the lifespan of those mice with inducible lung cancer.

Evaluation of the Use of mRNA-Transduced CARs to Provide Short Term Persistence

No toxicity was noted in mice treated with virally-transduced FAP-CAR T cells. However, it is important to provide a potential alternative, namely mRNA electroporation, for transient CAR expression. It was hypothesized that delivery of T cells that have been electroporated with FAP-CAR mRNA would be efficacious and safe. To accomplish this, vectors and electroporation techniques were developed that facilitate transfection of human T cells with CAR mRNA and that achieve high-level surface expression for 3-5 days. The main rationale for this strategy was to have T cells that only transiently express the CAR as a key safety feature. Any off-target effects mediated by CAR should be limited.

Figure 34:
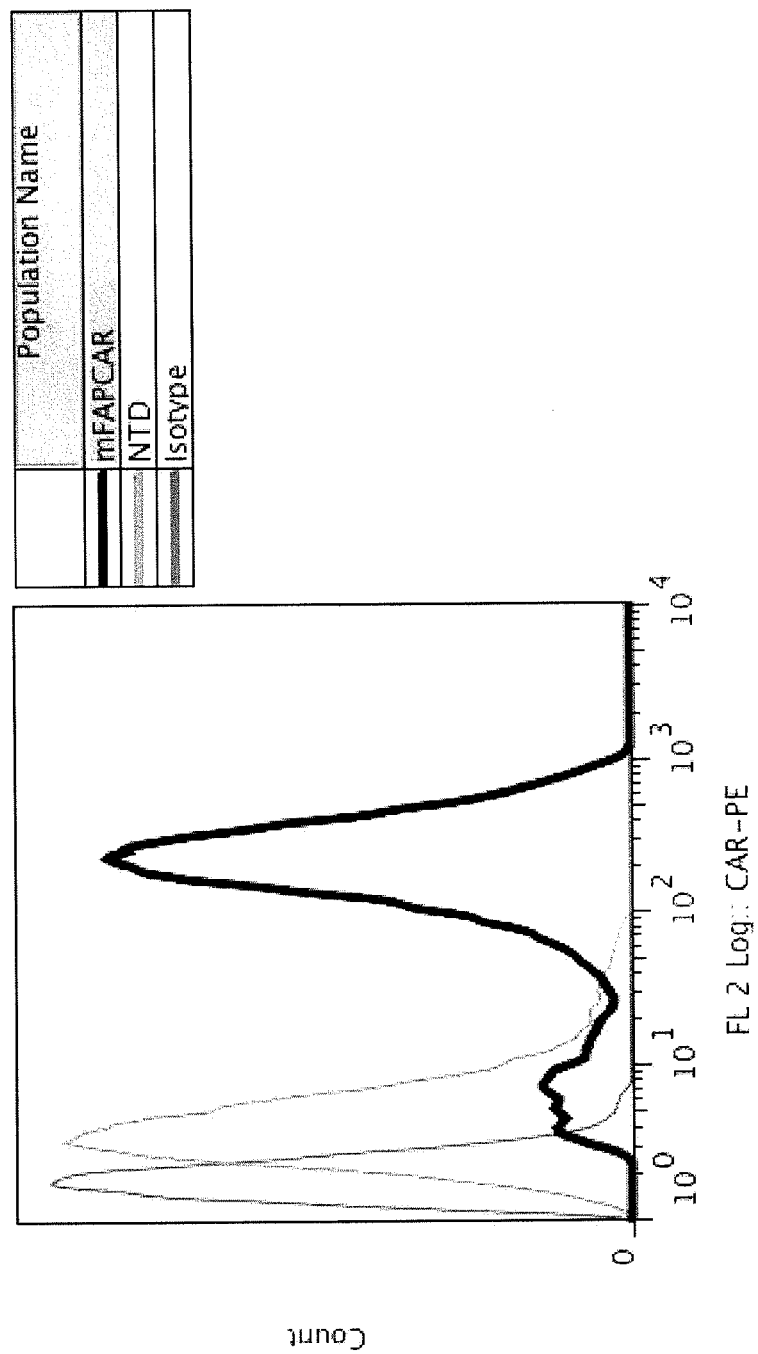
FIG. 34 is a graph depicting CAR expression in human T cells after electroporation with anti-mouse FAP CAR mRNA.
Figure 35:
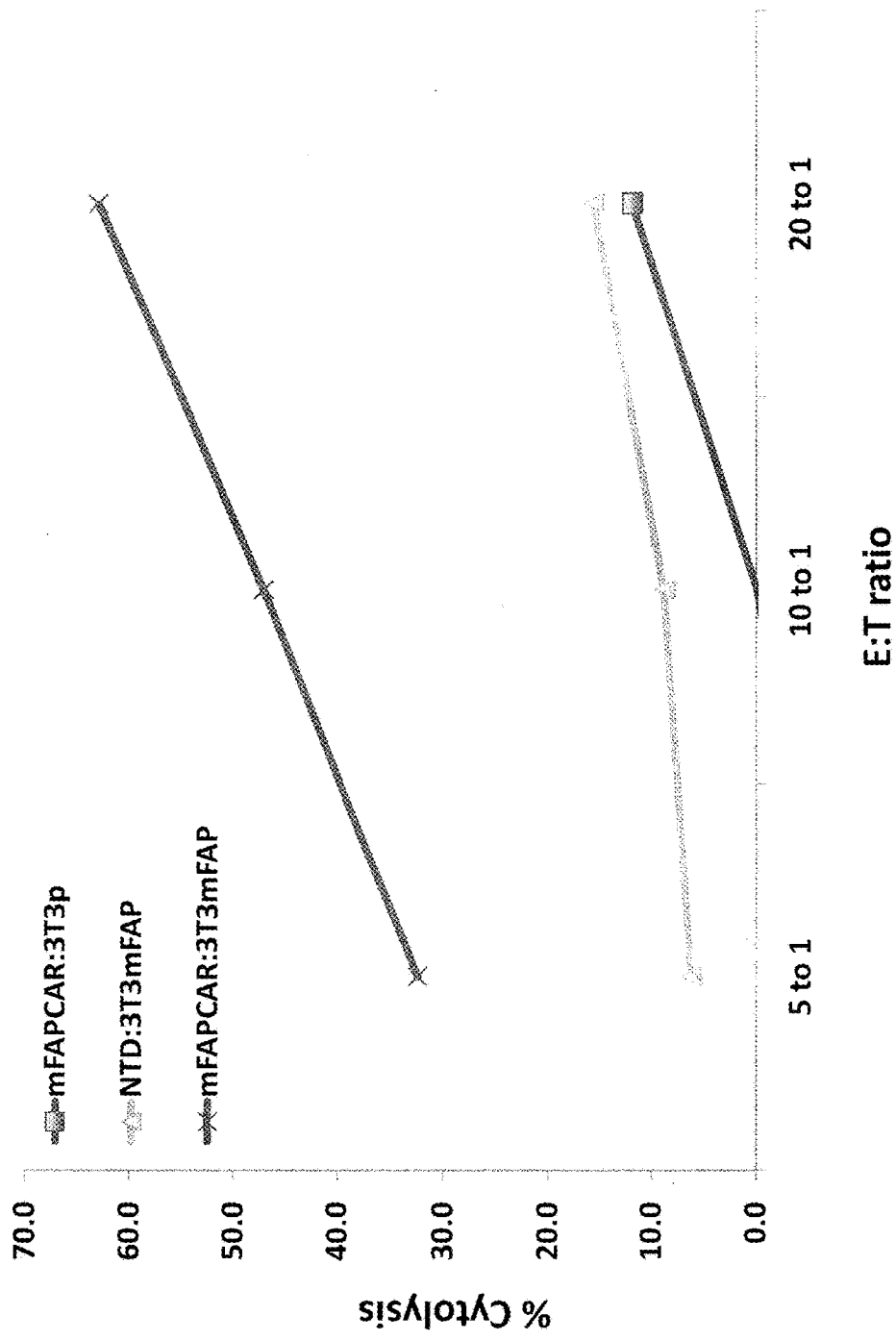
FIG. 35 is a graph depicting killing of FAP-expressing cells by mRNA-transfected T cells.
Figure 36:
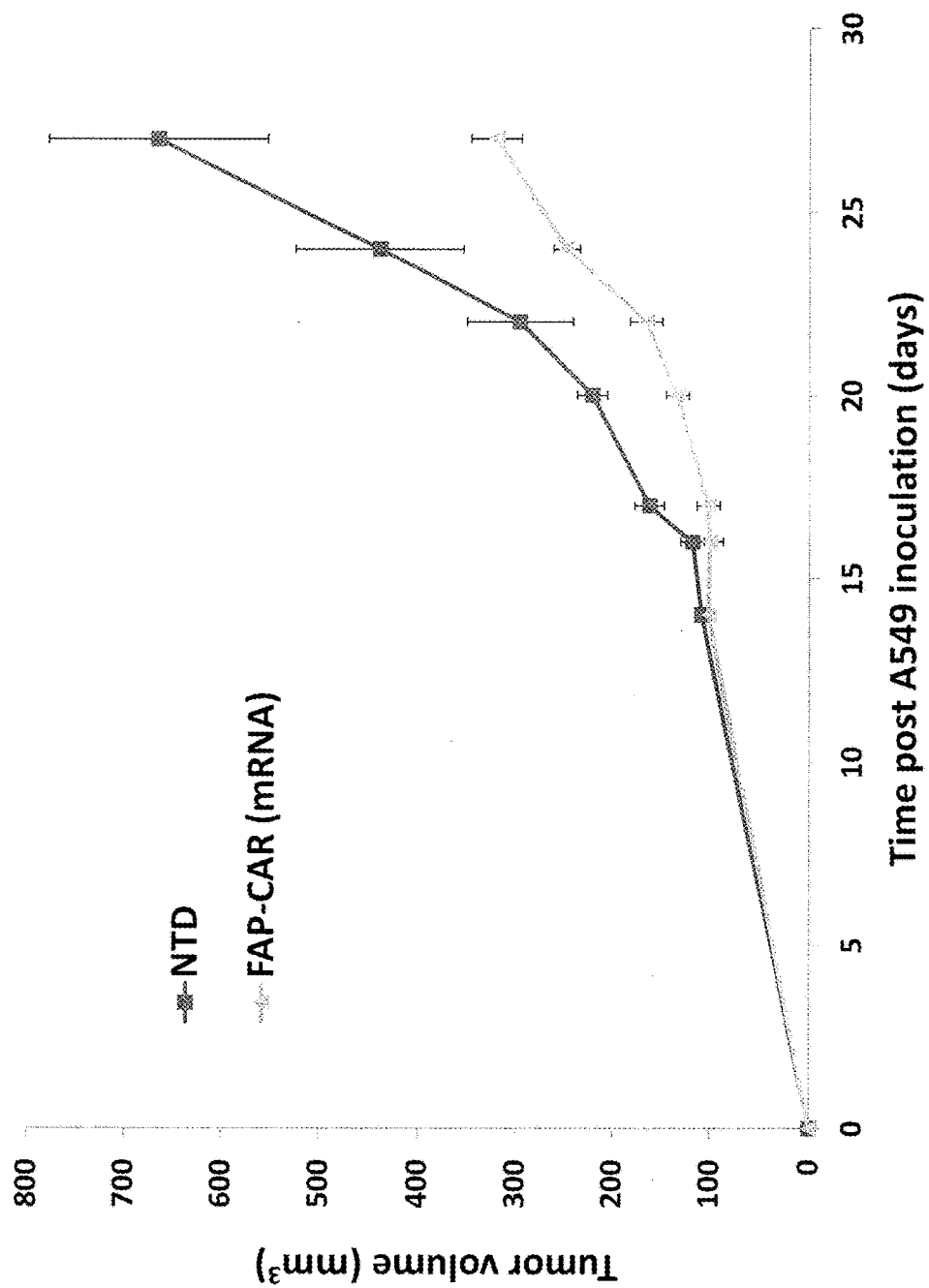
FIG. 36 is a graph depicting mRNA CAR T cells in A549 xenograft model.

FIG. 34 illustrates high surface FAP-CAR expression in human T cells that were electroporated 48 hours earlier with anti-mouse FAP-CAR mRNA. The black line shows high level CAR expression in the electroporated cells versus non-transfected and isotype control. These mRNA transfected T cells can effectively and selectively kill the 3T3 cell line transduced with mouse FAP in vitro (FIG. 35—see purple line). To demonstrate that the mRNA T cells have in vivo efficacy, on Day 14, $10^7$ mRNA-transduced human T cells (FAP-CAR) or non-transduced T cells (NTD) were injected every week for two doses into immunodeficient mice bearing established human A549 tumors (which induce large amounts of FAP⁺ CAFs). FIG. 36 illustrates that these cells have clear anti-tumor efficacy. This new data establish that mRNA-transfected CAR T cells can function efficiently in T cells and direct killing of tumor cells both in vitro and in an animal tumor model. There was no change in body weight and there was no sign of anemia in those mRNA CAT T cells-treated mice.

Evaluation of Anti-Human FAP CAR T Cells

The sequence of the light and heavy chains of the well-characterized F19 anti-human FAP monoclonal antibody was obtained from the Ludwig Institute.

Figure 37:
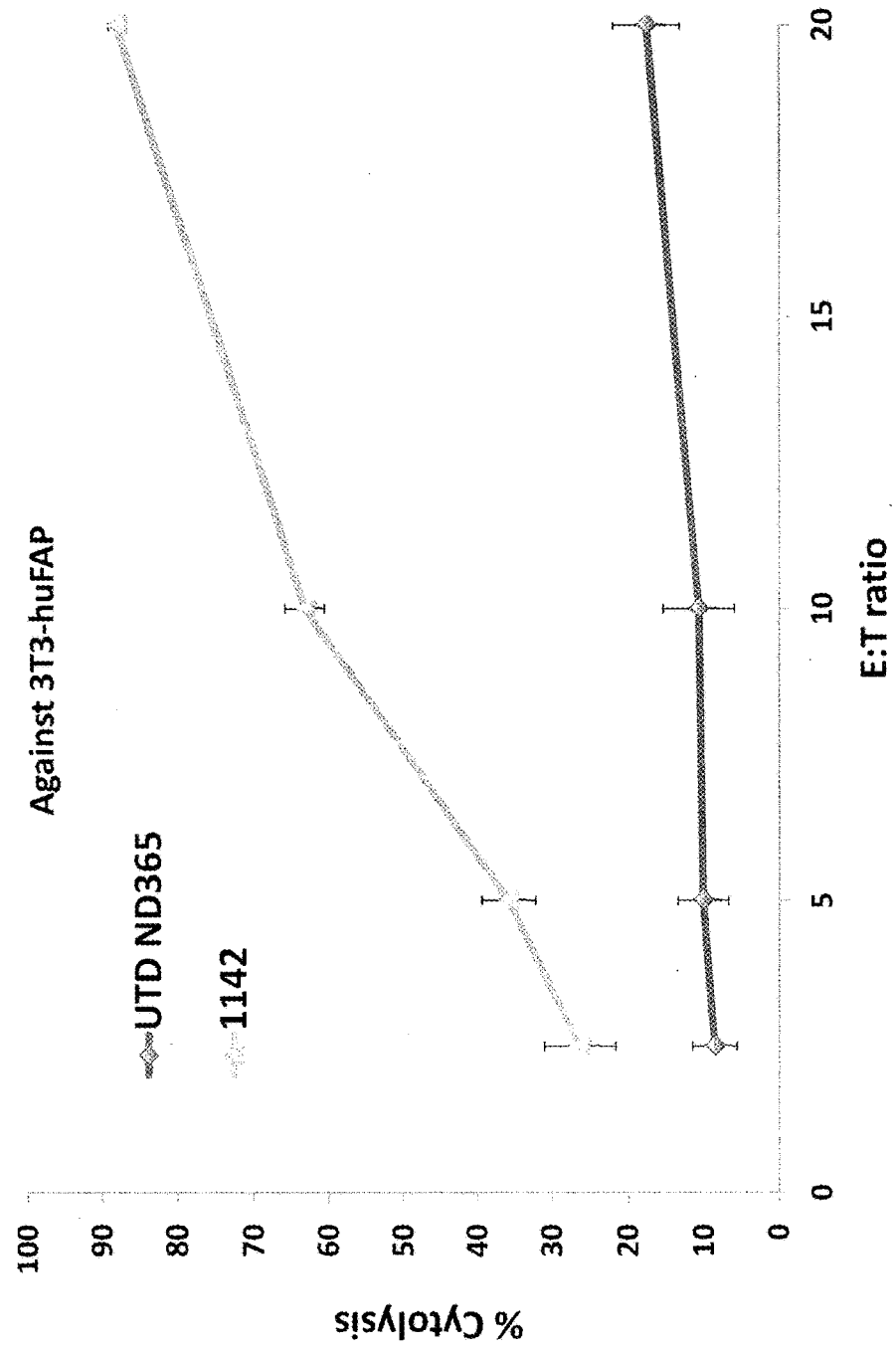
FIG. 37 is a graph depicting cytolytic activity of anti-huFAP CAR T cells against 3T3 expressing human FAP.
Figure 38:
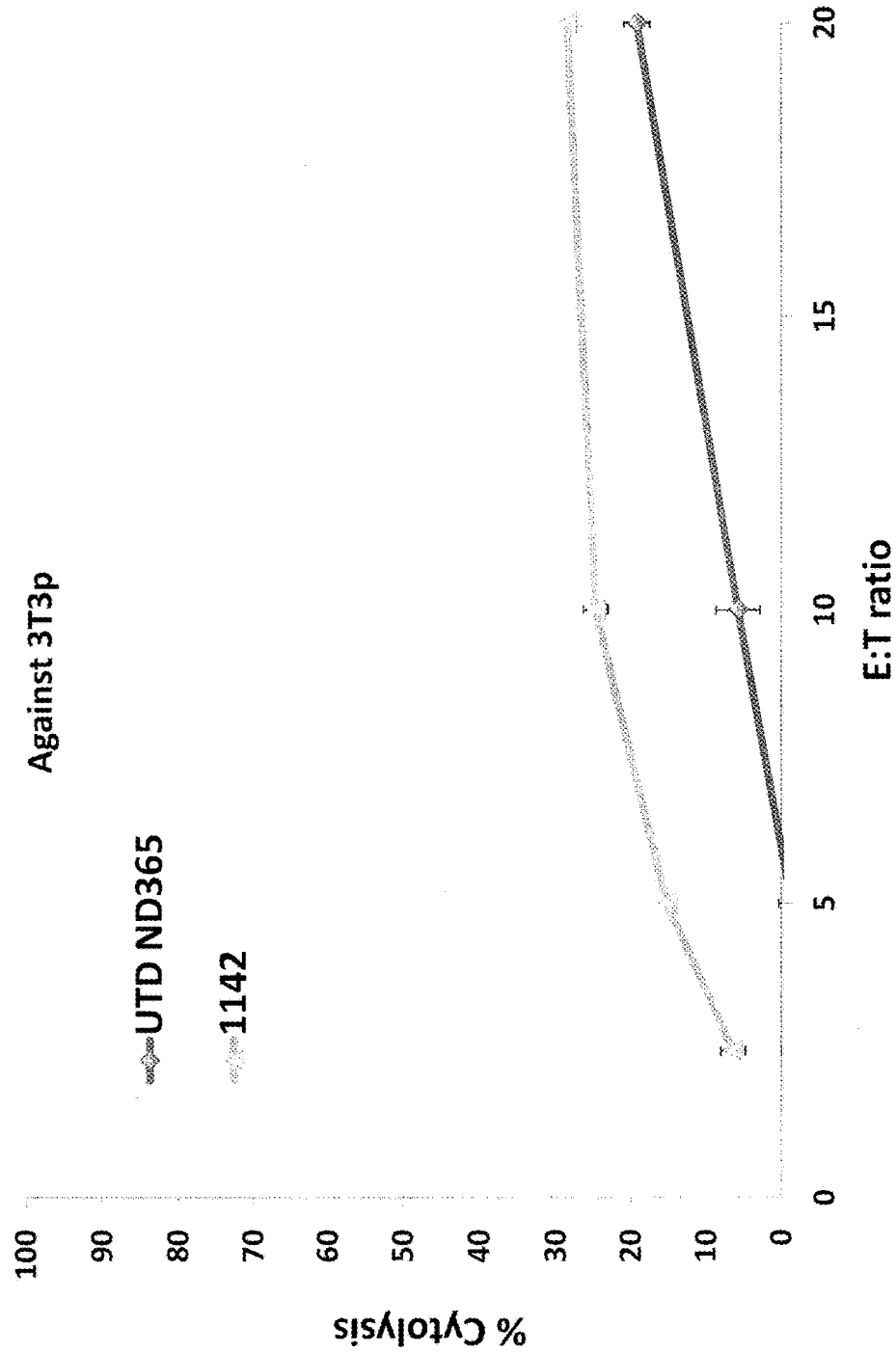
FIG. 38 is a graph depicting cytolytic activity of anti-huFAP CAR T cells against FAP-null 3T3 cells.
Figure 39:
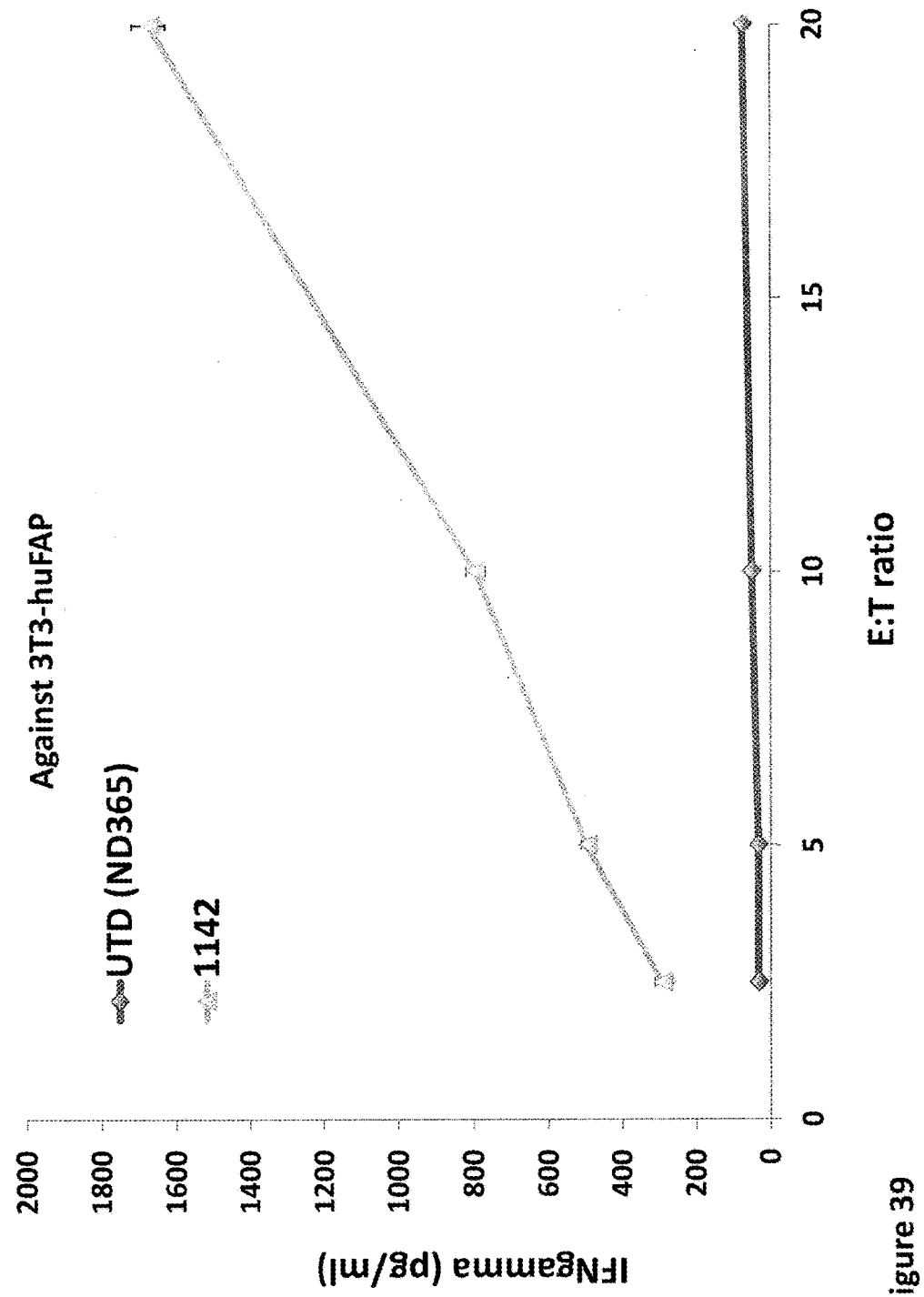
FIG. 39 is a graph depicting IFNg production of anti-huFAP CAR T cells against 3T3 expressing human FAP.
Figure 40:
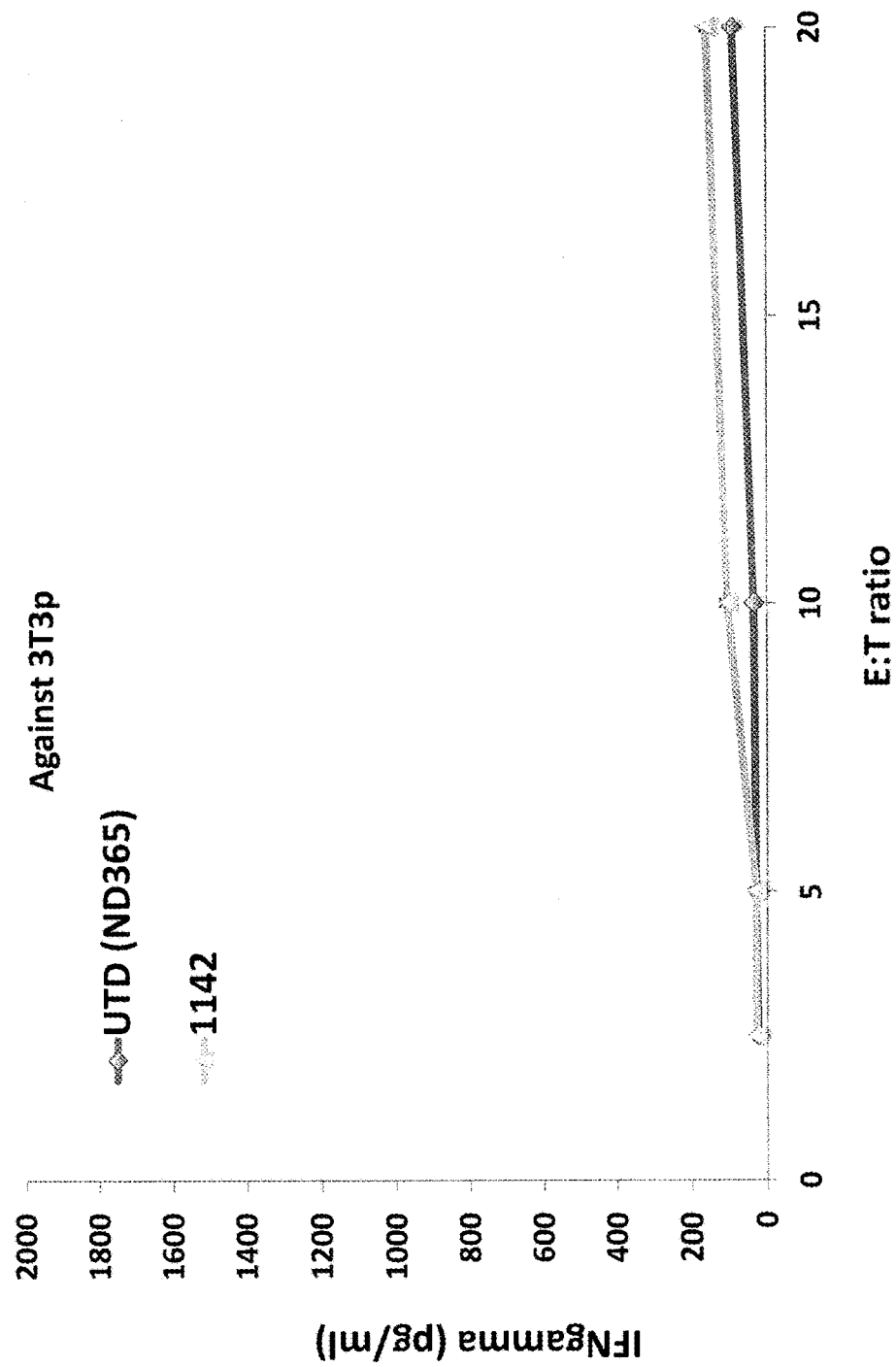
FIG. 40 is a graph depicting IFNg of anti-huFAP CAR T cells against FAP-null 3T3 cells.

These chains were inserted into the 4-1BB:CD3ζ "double activation domain" construct and a lentivirus was produced. Human T cells were transduced and evaluated with regard to expression level, and the ability to secrete cytokines and kill human FAP-expressing cells. Untransduced T cells or the anti-huFAP-CAR T cells (labeled 1142 on the figures) were reacted for 18 hours with either wild type (parental) 3T3p cells (mouse fibroblasts that do not express FAP) or 3T3 cells transduced to express human FAP (3T3huFAP) at different T cell to fibroblast ratio. FIGS. 37 and 38 illustrate that huFAP T cells selectively and effectively kill 3T3 cells expressing human FAP with no effect of control T cells. FIGS. 39 and 40 illustrate that only huFAP T cells selectively release IFNγ after exposure of 3T3 cells expressing human FAP. These data establish that the humanFAP-CAR T cells selectively and efficiently release IFNγ and kill fibroblast cells expressing human FAP.

Safety of FAP-CAR T Cells in Wound Healing

Figure 41:
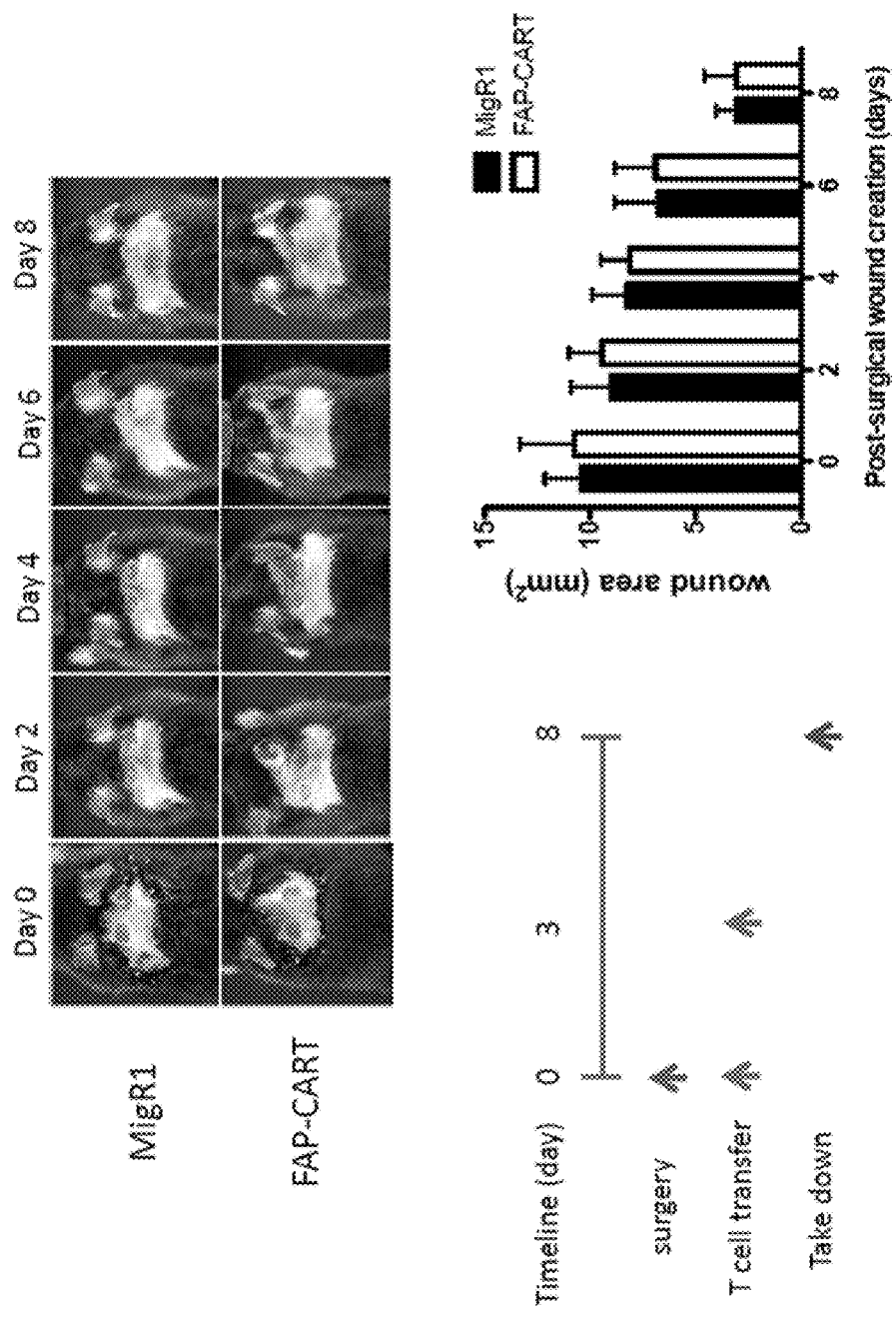
FIG. 41 is series of images and a graph depicting that administration of FAP-CAR T cells did not interfere with host wound healing response.
Figure 42:
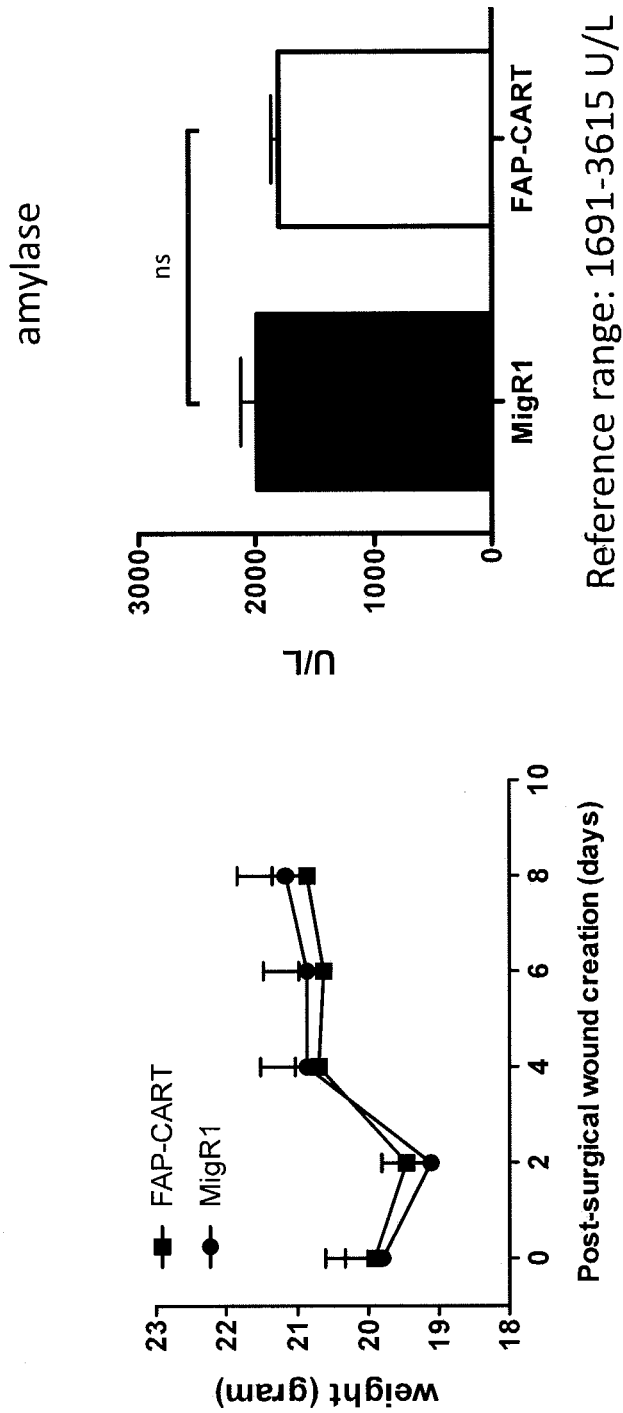
FIG. 42 is a series of graphs depicting that administration of FAP-CAR T cells did not cause weight loss or toxicity in pancreas.

Mice were given a calibrated skin wound on their backs using a dermal biopsy punch using techniques described in the art. Four hours post wound induction, mice received either $10^7$ muFAP-CAR murine T cells or $10^7$ retrovirally murine T cells transduced with the control CAR to rule out non-specific effects. Another dose of T cells was adoptively transferred 3 days later. In single-blinded fashion, the wound size was measured daily in each mouse and the groups compared. FIG. 41 illustrates that FAP-CAR T cells did not affect the closure of wounds. In addition, FAP-CAR T cells did not cause weight loss or toxicity in pancreas, which was determined by measuring plasma amylase level (FIG. 42).

Safety of FAP-CAR T Cells in Lung Fibrosis

FAP is expressed in the lungs of patients with pulmonary fibrosis. Although the "standard" model to study pulmonary fibrosis is instillation of bleomycin, this model is actually highly inflammatory and results in only transient fibrosis. A much better model of the human disease is fibrosis secondary to lung irradiation.

Figure 43:
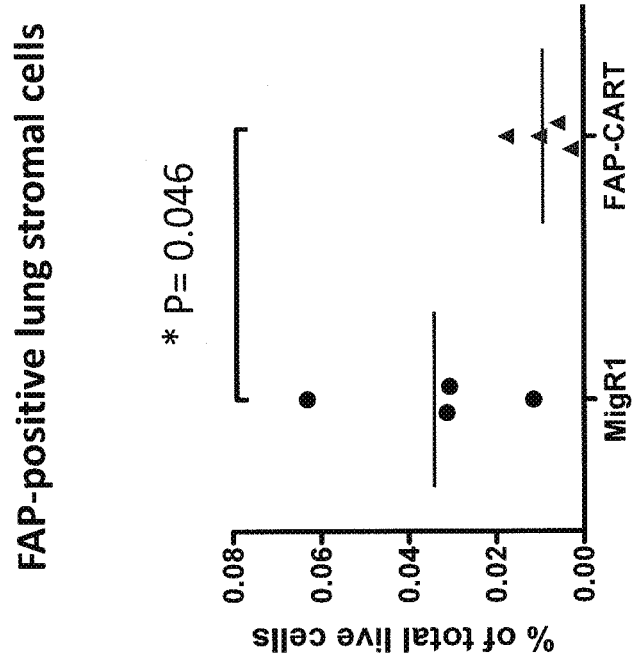
FIG. 43 is a graph depicting decrease in FAP-positive lung stromal cells following treatment of FAPCAR T cells in mice with pulmonary fibrosis.

C57/B16 mice (n=20 per group) received 13.5 Gy of chest irradiation. At four months post-irradiation, at a time when pulmonary fibrosis is known to exist, mice were randomized to receive $10^7$ control CAR T cells or $10^7$ anti-mouse FAP-CAR T cells. After one week, one set of mice were sacrificed. The remainder were given saline or a second dose of control or FAP-CAR T cells and sacrificed after an additional week. Using FACS analysis, increased FAP⁺ cells were seen in the lungs of control irradiated mice (compared to non-radiated mice). These cells were significantly decreased after CAR treatment showing the T cells had activity (FIG. 43). Importantly, no toxicity was observed after either the first or second infusion of FAP CAR T cells (specifically, no increased deaths, nor changes in weight, oxygenation, or respiration rate was observed). Staining of the lungs and FACS analysis showed no evidence of increased inflammation in the lungs of FAP-CAR T cell group. These preliminary data support the safety of FAP-CAR T cells, even in the presence of lung fibrosis.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated chimeric antigen receptor (CAR) comprising an antigen binding domain encoded by a nucleic acid sequence comprising SEQ ID NO: 3, a transmembrane domain, a costimulatory signaling region, and a CD3 zeta signaling domain, wherein the antigen binding domain binds to a stromal cell antigen.

2. The isolated CAR of claim 1, wherein the stromal cell antigen is expressed on a stromal cell present in a tumor microenvironment.

3. The isolated CAR of claim 2, wherein the tumor is a carcinoma.

4. The isolated CAR of claim 1, wherein the stromal cell antigen is fibroblast activation protein (FAP).

5. The isolated CAR of claim 1, wherein the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

6. The isolated CAR of claim 1, wherein the CAR is encoded by a nucleic acid sequence comprising SEQ ID NO: 1.

7. The isolated CAR of claim 1, wherein the transmembrane domain is encoded by a nucleic acid sequence comprising SEQ ID NO: 5.

8. The isolated CAR of claim 1, wherein the costimulatory signaling region is encoded by a nucleic acid sequence comprising SEQ ID NO: 6.

9. The isolated CAR of claim 1, wherein the CD3 zeta signaling domain is encoded by a nucleic acid sequence comprising SEQ ID NO: 7.

* * * * *

UNITED STATES PATENT AND TRADEMARK OFFICE
CERTIFICATE OF CORRECTION

| | |
|---|---|
| PATENT NO. | : 10,329,355 B2 |
| APPLICATION NO. | : 15/158727 |
| DATED | : June 25, 2019 |
| INVENTOR(S) | : Carl H. June et al. |

It is certified that error appears in the above-identified patent and that said Letters Patent is hereby corrected as shown below:

In the Specification

In Column 1, Line 1 after the heading "STATEMENT REGARDING FEDERALLY SPONSORED RESEARCH OR DEVELOPMENT", replace the paragraph at Lines 17-20 with the following paragraph:
--This invention was made with government support under CA141144, CA172921 and CA066726 awarded by the National Institutes of Health. The government has certain rights in the invention.--

Signed and Sealed this
Nineteenth Day of September, 2023

Katherine Kelly Vidal
*Director of the United States Patent and Trademark Office*